US011071727B2

(12) United States Patent
Shilatifard et al.

(10) Patent No.: US 11,071,727 B2
(45) Date of Patent: Jul. 27, 2021

(54) THERAPEUTIC TARGETING OF PROTEOLYTIC CLEAVAGE OF THE MIXED LINEAGE LEUKEMIA GENE PRODUCT (MLL1) BY TASPASE1 USING KINASE INHIBITORS

(71) Applicant: Northwestern University, Evanston, IL (US)

(72) Inventors: Ali Shilatifard, Chicago, IL (US); Zibo Zhao, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/257,581

(22) Filed: Jan. 25, 2019

(65) Prior Publication Data

US 2019/0231759 A1    Aug. 1, 2019

Related U.S. Application Data

(60) Provisional application No. 62/622,376, filed on Jan. 26, 2018.

(51) Int. Cl.
*A61K 31/4375* (2006.01)
*A61P 35/02* (2006.01)

(52) U.S. Cl.
CPC .......... *A61K 31/4375* (2013.01); *A61P 35/02* (2018.01)

(58) Field of Classification Search
CPC ................................................. A61K 31/4375
USPC ........................................................ 514/293
See application file for complete search history.

(56) References Cited

U.S. PATENT DOCUMENTS

| | | | |
|---|---|---|---|
| 7,956,064 B2 * | 6/2011 | Chua .................... | C07D 221/12 514/292 |
| 7,964,700 B2 | 6/2011 | Hsieh | |
| 8,168,651 B2 | 5/2012 | Chua | |
| 8,367,681 B2 | 2/2013 | Haddach | |
| 8,501,811 B2 | 8/2013 | Hsieh | |
| 8,575,177 B2 | 11/2013 | Haddach | |
| 8,853,234 B2 | 10/2014 | Nagasawa | |
| 8,853,235 B2 | 10/2014 | Ryckman | |
| 9,062,043 B2 | 6/2015 | Chua | |
| 2009/0093465 A1 | 4/2009 | Pierre | |
| 2009/0215761 A1 | 8/2009 | Whitten | |
| 2009/0264423 A2 | 10/2009 | Chua | |
| 2011/0065698 A1 | 3/2011 | Pierre | |
| 2011/0065712 A1 | 3/2011 | Haddach | |
| 2011/0071115 A1 | 3/2011 | Haddach | |
| 2011/0071136 A1 | 3/2011 | Haddach | |
| 2011/0112086 A1 | 5/2011 | Pierre | |
| 2011/0152240 A1 | 6/2011 | Haddach | |
| 2011/0160240 A1 | 6/2011 | Ryckman | |
| 2011/0218184 A1 | 9/2011 | Nagasawa | |
| 2011/0263581 A1 | 10/2011 | Chua | |
| 2012/0122804 A1 | 5/2012 | Whitten | |
| 2012/0129849 A1 | 5/2012 | Haddach | |
| 2012/0190669 A1 | 7/2012 | Haddach | |
| 2012/0208792 A1 | 8/2012 | Chua | |
| 2014/0094448 A1 | 4/2014 | Haddach | |

OTHER PUBLICATIONS

Tubi et al., J. Hemat. Oncology (2013), vol. 6:78, pp. 1-15.*
Lian et al., Haematologica (2017) 102: e17-e21.*
Anders S, et al. 2015. HTSeq—a Python framework to work with high-throughput sequencing data. Bioinformatics 31: 166-169.
Andrews S. 2010. FastQC: a quality control tool for high throughput sequence data. Available online at the following website: http://www.bioinformatics.babraham.ac.uk/projects/fastqc.
Armstrong SA, et al. 2002. MLL translocations specify a distinct gene expression profile that distinguishes a unique leukemia. Nat Genet 30: 41-47.
Ayton PM, et al. 2003. Transformation of myeloid progenitors by MLL oncoproteins is dependent on Hoxa7 and Hoxa9. Genes & development 17: 2298-2307.
Bier C, et al. 2012. Overexpression of the catalytically impaired Taspase1 T234V or Taspase1 D233A variants does not have a dominant negative effect in T(4;11) leukemia cells. PloS one 7: e34142.
Bier C, et al. 2011a. The importin-alpha/nucleophosmin switch controls taspase1 protease function. Traffic 12: 703-714.
Bier C, et al. 2011b. Cell-based analysis of structure-function activity of threonine aspartase 1. The Journal of biological chemistry 286: 3007-3017.
Blom N, et al. 2004. Prediction of post-translational glycosylation and phosphorylation of proteins from the amino acid sequence. Proteomics 4: 1633-1649.
Bursen A, et al. 2010. The AF4.MLL fusion protein is capable of inducing ALL in mice without requirement of MLL. AF4. Blood 115: 3570-3579.
Capotosti F, et al. 2011. O-GlcNAc transferase catalyzes site-specific proteolysis of HCF-1. Cell 144: 376-388.
Capotosti F, et al. 2007. Species selectivity of mixed-lineage leukemia/trithorax and HCF proteolytic maturation pathways. Mol Cell Biol 27: 7063-7072.
Chen DY, et al. 2012. A pharmacologic inhibitor of the protease Taspase1 effectively inhibits breast and brain tumor growth. Cancer research 72: 736-746.

(Continued)

*Primary Examiner* — Taofiq A Solola
(74) *Attorney, Agent, or Firm* — Quarles & Brady LLP; M. McBride

(57) ABSTRACT

Disclosed are methods and pharmaceutical compositions for treating a cancer in a subject in need thereof, the cancer characterized by proteolytic cleavage by taspase1 of the mixed-lineage leukemia 1 gene product (MLL1), the method comprising administering to the subject a therapeutic agent that inhibits cleavage by taspase1 of MLL1. Suitable therapeutic agents may include agents that inhibit the kinase activity of casein kinase II (CKII). Cancer treated by the disclosed methods and pharmaceutical compositions may include leukemia such as Acute Lymphoblastic Leukemia (ALL) and/or Acute Myeloid Leukemia (AML) and in particular, leukemia characterized by rearrangements in MLL1.

2 Claims, 57 Drawing Sheets

Specification includes a Sequence Listing.

(56) References Cited

OTHER PUBLICATIONS

Chen DY, et al. 2010. Taspase1 functions as a non-oncogene addiction protease that coordinates cancer cell proliferation and apoptosis. Cancer research 70: 5358-5367.

Chen FX, et al. 2015. PAF1, a Molecular Regulator of Promoter-Proximal Pausing by RNA Polymerase II. Cell 162: 1003-1015.

Cong L, et al. 2015. Genome Engineering Using CRISPR-Cas9 System. Methods Mol Biol 1239: 197-217.

Cozza, G. "The development of CK2 inhibitors: From traditional pharmacology to in silico rational drug design." Pharmaceuticals 10.1 (2017): 26.

Daou S, et al. 2011. Crosstalk between O-GlcNAcylation and proteolytic cleavage regulates the host cell factor-1 maturation pathway. Proc Natl Acad Sci U S A 108: 2747-2752.

Dong Y, et al. 2014. Taspase1 cleaves MLL1 to activate cyclin E for HER2/neu breast tumorigenesis. Cell research 24:1354-1366.

Fair K, et al. 2001. Protein interactions of the MLL PHD fingers modulate MLL target gene regulation in human cells. Mol Cell Biol 21: 3589-3597.

Heinz S, et al. 2010. Simple combinations of lineage-determining transcription factors prime cis-regulatory elements required for macrophage and B cell identities. Mol Cell 38: 576-589.

Hess JL. 2004. Mechanisms of transformation by MLL. Crit Rev Eukaryot Gene Expr 14: 235-254.

Hoiby T, et al. 2004. Cleavage and proteasome-mediated degradation of the basal transcription factor TFIIA. Embo J 23:3083-3091.

Hornbeck PV, et al. 2015. PhosphoSitePlus, 2014: mutations, PTMs and recalibrations. Nucleic acids research 43: D512-520.

Hsieh JJ, et al. 2003a. Taspase1: a threonine aspartase required for cleavage of MLL and proper HOX gene expression. Cell 115: 293-303.

Hsieh JJ, et al. 2003b. Proteolytic cleavage of MLL generates a complex of N- and C-terminal fragments that confers protein stability and subnuclear localization. Mol Cell Biol 23: 186-194.

Hu D, et al. 2013. The Mll2 branch of the COMPASS family regulates bivalent promoters in mouse embryonic stem cells. Nature structural & molecular biology 20: 1093-1097.

Khan JA, et al. 2005. Crystal structure of human Taspase1, a crucial protease regulating the function of MLL. Structure 13: 1443-1452.

Kim D, et al. 2013. TopHat2: accurate alignment of transcriptomes in the presence of insertions, deletions and gene fusions. Genome biology 14: R36.

Kowarz E, et al. 2007. Complex MLL rearrangements in t(4;11) leukemia patients with absent AF4.MLL fusion allele. Leukemia 21: 1232-1238.

Langmead B, et al. 2009. Ultrafast and memory-efficient alignment of short DNA sequences to the human genome. Genome biology 10: R25.

Lawrence M, et al. 2013. Software for computing and annotating genomic ranges. PLoS computational biology 9: e1003118.

Liang K, et al. 2017. Therapeutic Targeting of MLL Degradation Pathways in MLL-Rearranged Leukemia. Cell 168: 59-72 e13.

Luo Z, et al. 2012. The super elongation complex (SEC) family in transcriptional control. Nat Rev Mol Cell Biol 13: 543-547.

Meggio F, et al. 1994. Substrate specificity of protein kinase CK2. Cellular & molecular biology research 40: 401-409.

Miller T, et al. 2001. COMPASS: a complex of proteins associated with a trithorax-related SET domain protein. Proc Natl Acad Sci U S A 98: 12902-12907.

Milne TA, et al. 2002. MLL targets SET domain methyltransferase activity to Hox gene promoters. Mol Cell 10: 1107-1117.

Nakamura T, et al. 2002. ALL-1 is a histone methyltransferase that assembles a supercomplex of proteins involved in transcriptional regulation. Mol Cell 10: 1119-1128.

Natarajan TG, et al. 2010. Epigenetic regulator MLL2 shows altered expression in cancer cell lines and tumors from human breast and colon. Cancer cell international 10: 13.

Niizuma, H. et al. "Taspase 1: A protease with many biological surprises." Molecular & cellular oncology 2.4 (2015): e999513.

Noetzel E, et al. 2012. Nuclear transport receptor karyopherin-alpha2 promotes malignant breast cancer phenotypes in vitro. Oncogene 31: 2101-2114.

Pagano, "The selectivity of inhibitor of protein kinase CK2: an update," Biochem. J. Nov. 1, 2008;415(3):353-65.

Pierre et al., "Discovery and SAR of 5-(3-chlorophenylamino) benzo[c][2,6]naphthyridine-8-carboxylic acid (CX-4945), the first clinical stage inhibitor of protein kinase CK2 for the treatment of cancer," J. Med. Chem. Jan. 27, 2011; 54(2):635-54.

Piunti A, et al. 2016. Epigenetic balance of gene expression by Polycomb and COMPASS families. Science 352: aad9780.

Pless B, et al. 2011. The heterodimerization domains of MLL-FYRN and FYRC—are potential target structures in t(4;11) leukemia. Leukemia 25: 663-670.

Quinlan AR, et al. 2010. BEDTools: a flexible suite of utilities for comparing genomic features. Bioinformatics 26: 841-842.

Rickels R, et al. 2016. An Evolutionary Conserved Epigenetic Mark of Polycomb Response Elements Implemented by Trx/MLL/COMPASS. Mol Cell 63: 318-328.

Robinson MD, et al. 2010. edgeR: a Bioconductor package for differential expression analysis of digital gene expression data. Bioinformatics 26: 139-140.

Rush J, et al. 2005. Immunoaffinity profiling of tyrosine phosphorylation in cancer cells. Nature biotechnology 23: 94-101.

Sabiani S, et al. 2015. Unraveling the Activation Mechanism of Taspase1 which Controls the Oncogenic AF4-MLL Fusion Protein. EBioMedicine 2: 386-395.

Sarno S, et al. 1996. Protein kinase CK2 mutants defective in substrate recognition. Purification and kinetic analysis. The Journal of biological chemistry 271: 10595-10601.

Schuettengruber B, et al. 2017. Genome Regulation by Polycomb and Trithorax: 70 Years and Counting. Cell 171: 34-57.

Shen L, et al. 2014. ngs.plot: Quick mining and visualization of next-generation sequencing data by integrating genomic databases. BMC genomics 15: 284.

Shilatifard A, et al. 1997. ELL2, a new member of an ELL family of RNA polymerase II elongation factors. Proc Natl Acad Sci U S A 94: 3639-3643.

Smith E, et al. 2011. The super elongation complex (SEC) and MLL in development and disease. Genes & development 25: 661-672.

Stauber RH, et al. 2012. Targeting Taspase1 for cancer therapy—letter. Cancer research 72: 2912; author reply 2913.

Takeda S, et al. 2006. Proteolysis of MLL family proteins is essential for taspase1-orchestrated cell cycle progression. Genes & development 20: 2397-2409.

Tripathi S, et al. 2015. Meta- and Orthogonal Integration of Influenza "OMICs" Data Defines a Role for UBR4 in Virus Budding. Cell host & microbe 18: 723-735.

Van Den Boom et al., "Peptidyl Succinimidyl Peptides as Taspase 1 Inhibitors," ChemBioChem, 2014, 15, 2233-2237.

Van Den Boom, J. Novel inhibitors for the protease Taspase1" Inaugural-Dissertation zur Erlangung des Doktorgrades Dr. rer. nat. Fakultät für Biologie der Universität Duisburg-Essen Campus Essen, Jun. 2014. 158 pages.

Von Mikecz A. 2006. The nuclear ubiquitin-proteasome system. J Cell Sci 119: 1977-1984.

Wang J, et al. 2012a. ECSASB2 mediates MLL degradation during hematopoietic differentiation. Blood 119: 1151-1161.

Wang J, et al. 2012b. A subset of mixed lineage leukemia proteins has plant homeodomain (PHD)-mediated E3 ligase activity. The Journal of biological chemistry 287: 43410-43416.

Wang L, et al. 2017. A cytoplasmic COMPASS is necessary for cell survival and triple-negative breast cancer pathogenesis by regulating metabolism. Genes & development 31: 2056-2066.

Wang L, et al. 2014. CARM1 methylates chromatin remodeling factor BAF155 to enhance tumor progression and metastasis. Cancer cell 25: 21-36.

Wang P, et al. 2009. Global analysis of H3K4 methylation defines MLL family member targets and points to a role for MLL1-mediated H3K4 methylation in the regulation of transcriptional initiation by RNA polymerase II. Mol Cell Biol 29: 6074-6085.

(56) References Cited

OTHER PUBLICATIONS

Wang Q, et al. 2016. Reprogramming of the Epigenome by MLL1 Links Early-Life Environmental Exposures to Prostate Cancer Risk. Molecular endocrinology 30: 856-871.
Wong P, et al. 2007. Meis1 is an essential and rate-limiting regulator of MLL leukemia stem cell potential. Genes & development 21: 2762-2774.
Wunsch D, et al. 2012. Chemico-genetic strategies to inhibit the leukemic potential of threonine aspartase-1. Blood cancer journal 2: e77.
Wunsch D, et al. 2015. Fly versus man: evolutionary impairment of nucleolar targeting affects the degradome of *Drosophila*'s Taspase1. FASEB journal : official publication of the Federation of American Societies for Experimental Biology 29: 1973-1985.
Wunsch D, et al. 2016. Taspase1: a 'misunderstood' protease with translational cancer relevance. Oncogene 35: 3351-3364.
Yokoyama A, et al. 2013. MLL becomes functional through intramolecular interaction not by proteolytic processing. PloS one 8: e73649.
Yokoyama A, et al. 2011. Proteolytically cleaved MLL subunits are susceptible to distinct degradation pathways. J Cell Sci 124: 2208-2219.
Yokoyama A, et al. 2002. Leukemia proto-oncoprotein MLL is proteolytically processed into 2 fragments with opposite transcriptional properties. Blood 100: 3710-3718.
Zeleznik-LE NJ, et al. 1994. 11q23 translocations split the "AT-hook" cruciform DNA-binding region and the transcriptional repression domain from the activation domain of the mixed-lineage leukemia (MLL) gene. Proc Natl Acad Sci U S A 91: 10610-10614.
Zhang P, et al. 2013. The many facets of MLL1 regulation. Biopolymers 99: 136-145.
Zhang Y, et al. 2008. Model-based analysis of ChIP-Seq (MACS). Genome biology 9: R137.
Zhao et al., "Therapeutic targeting of childhood leukemia by pharmacological inhibition of proteolytic cleavage of MLL1," submitted for review.
Zhao Z, et al. 2013. Systematic analyses of the cytotoxic effects of compound 11a, a putative synthetic agonist of photoreceptor-specific nuclear receptor (PNR), in cancer cell lines. PloS one 8: e75198.
Zhao Z, et al. 2014. IL-13Ralpha2 mediates PNR-induced migration and metastasis in ERalpha-negative breast cancer. Oncogene.
Zhou HQ, et al. 2006. Uncleaved TFIIA is a substrate for taspase 1 and active in transcription. Mol Cell Biol 26: 2728-2735.
Winters AC, et al. 2017. MLL-Rearranged Leukemias—An Update on Science and Clinical Approaches. Front. Pediatr. 5:4.
Steinhilber D., et al. 2018. How to effectively treat acute leukemia patients bearing MLL-rearrangements?. Biochemical Pharmacology, 147: 183-190.
De Boer J., et al. Leukemia (2013) 27, 1224-1228.
Loyola University Health System. "Possible new approach to treating deadly leukemia in babies." ScienceDaily. ScienceDaily, Apr. 14, 2011.
Perron, M. Oncology Times: Nov. 20, 2019-13 vol. 41—Issue S22—p. 17.

* cited by examiner

A

Figure 3 (cont.)
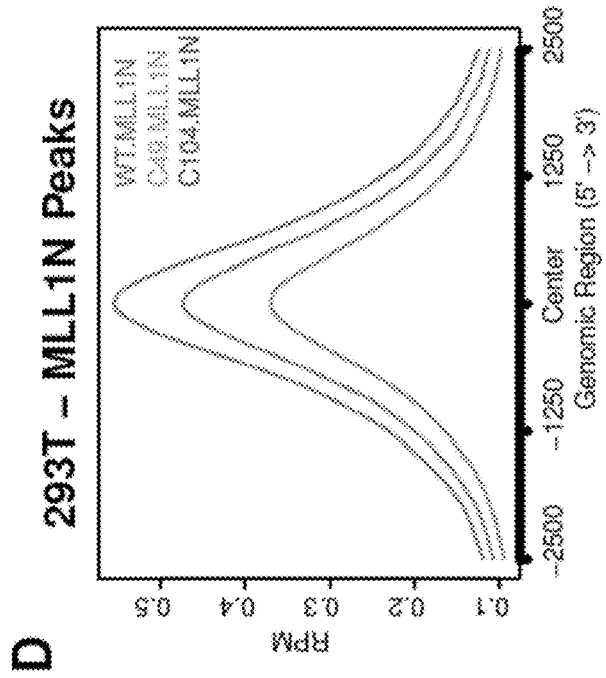
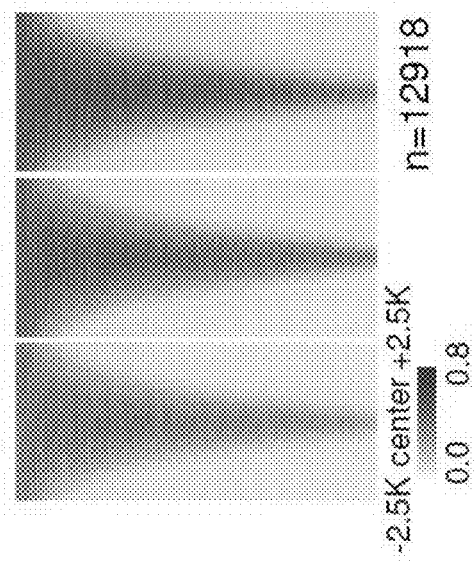
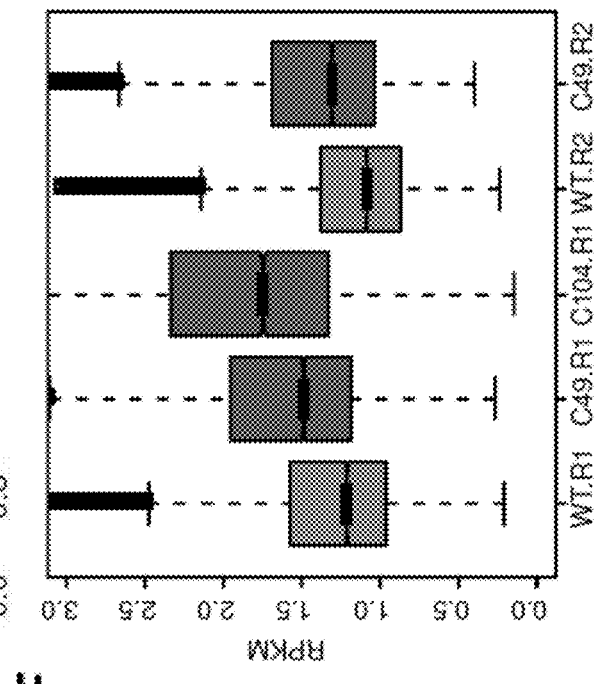

Figure 3
(cont.)
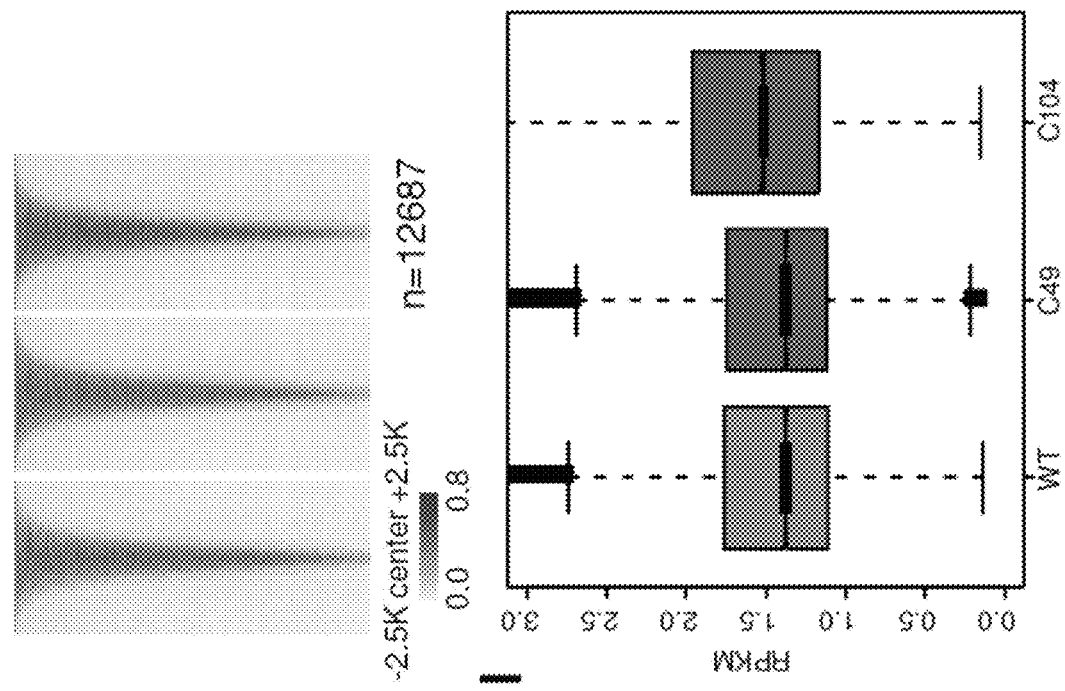
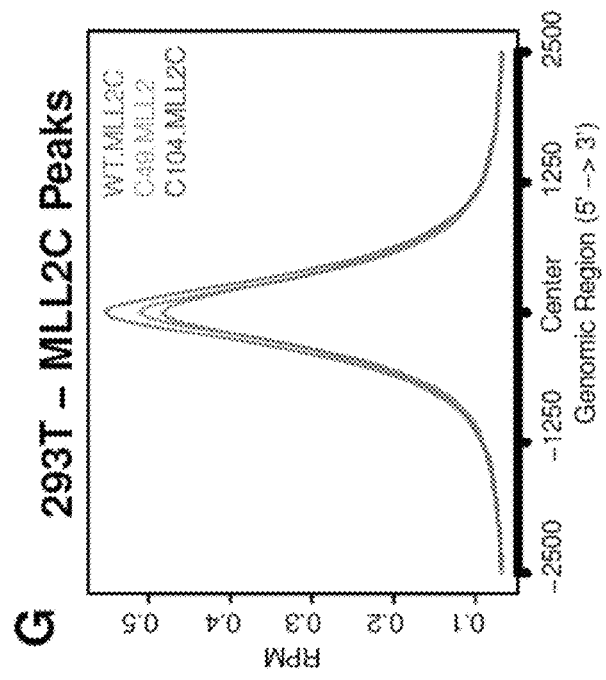

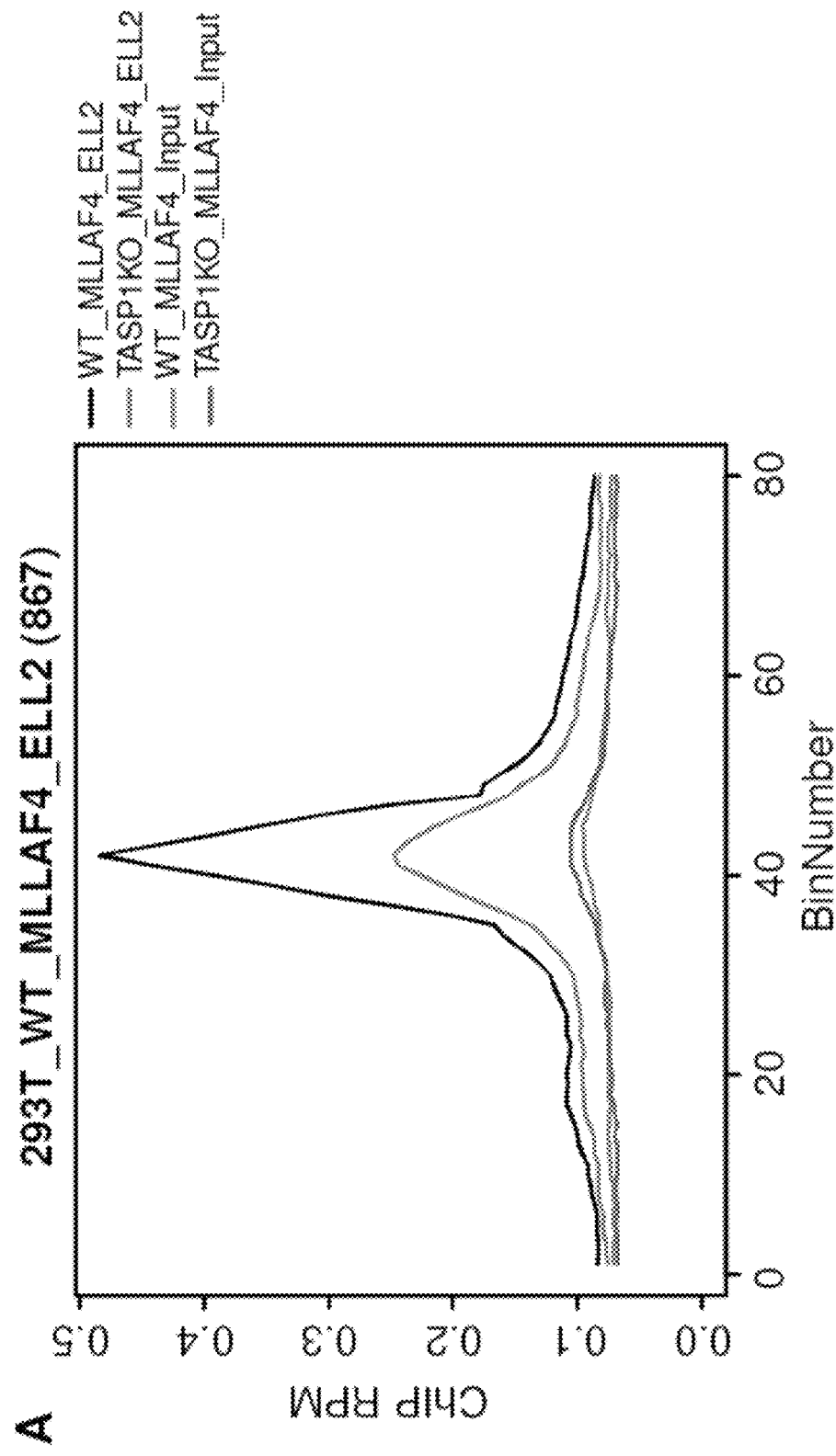

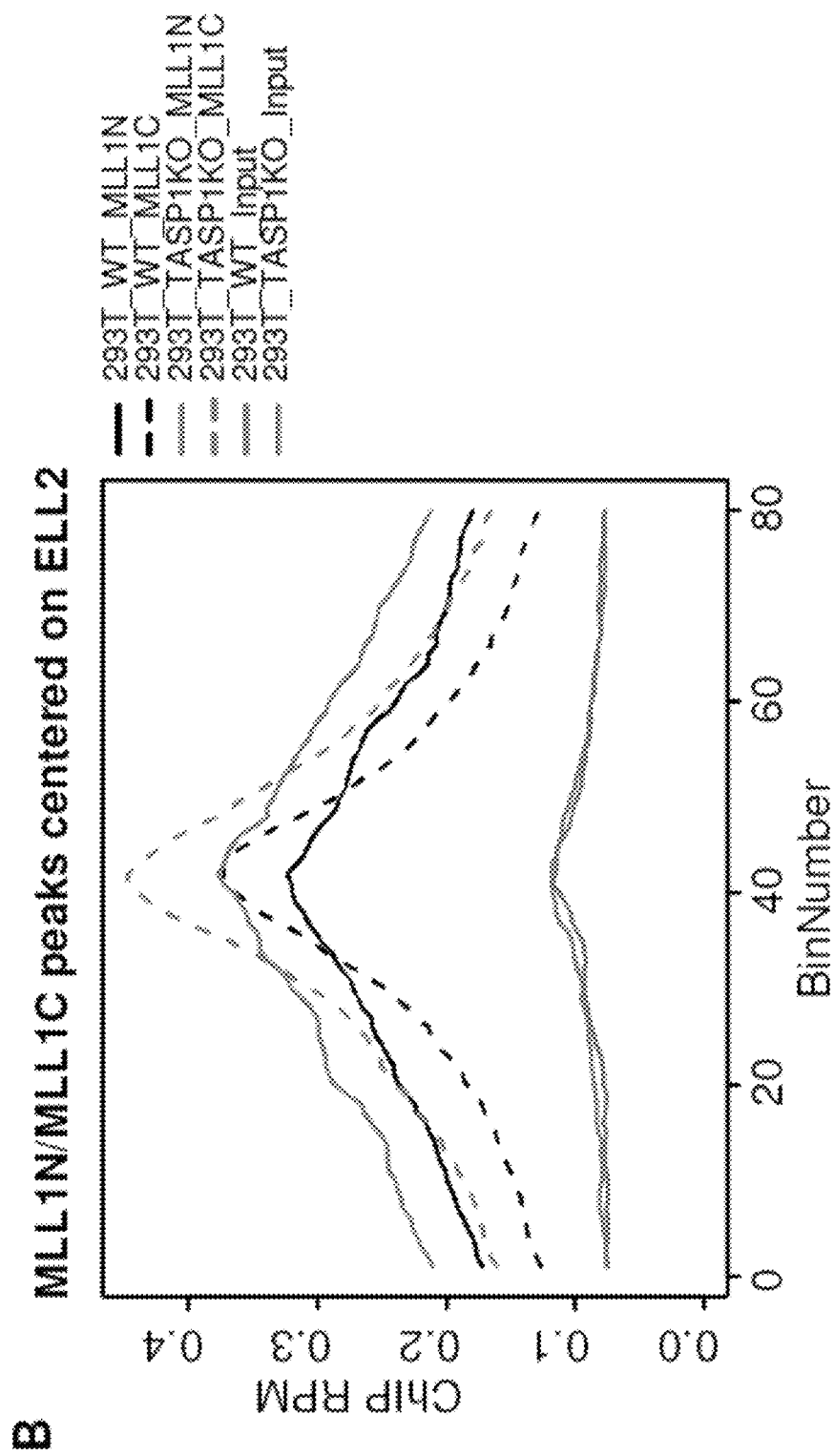

(SEQ ID NO:6) MLL1: KISQLD/GVDDGTESDTSVt (CS2)
(SEQ ID NO:7) MLL2: RIEQLD/GVDDGTDSEAEAV
(SEQ ID NO:8) TFIIA: LVLQVD/GTGDTSSEEDEDE

B 3xFlag-MLL1-p75

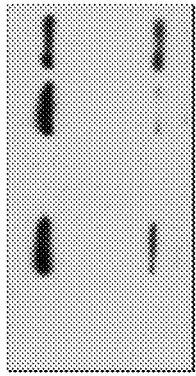

VT WT AA DD
→ p75
→ p47

```
              D2718  T2724S2726
MLL1:
WT  -  KISQLD/GVDDGTESDtSVt (CS2)
SA  -  KISQLD/GVDDGAEADtSVt (CS2)
SD  -  KISQLD/GVDDGDEDDtSVt (CS2)
```
(SEQ ID NO:6)
(SEQ ID NO:9)
(SEQ ID NO:10)

C 3xFlag-TFIIA

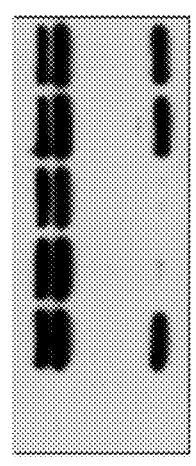

VT WT AA AA DD DD
→ p54
→ p35

```
              D274   S280S281
TFIIA:
WT  -  LVLQVD/GTGDTSSEEDEDE
SA  -  LVLQVD/GTGDTAAEEDEDE
SD  -  LVLQVD/GTGDTDDEEDEDE
```
(SEQ ID NO:8)
(SEQ ID NO:11)
(SEQ ID NO:12)

Figure 7
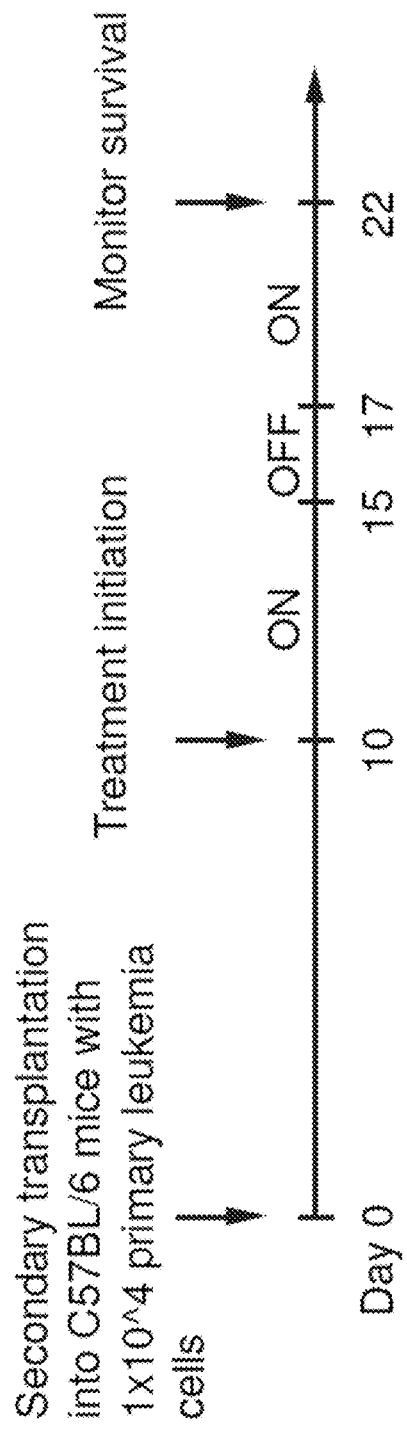
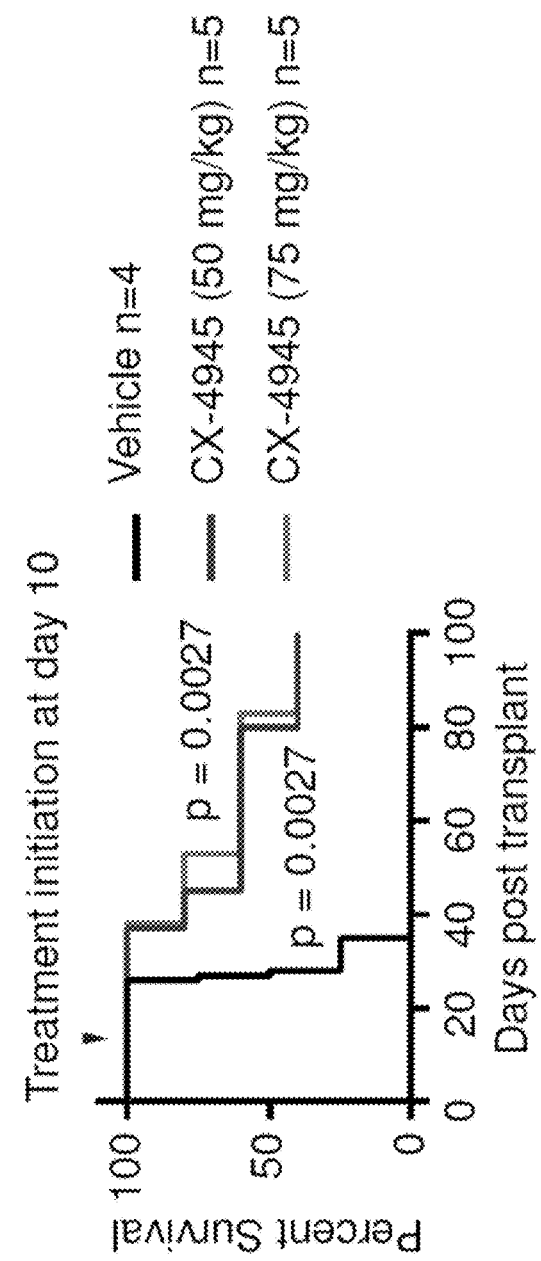

Figure 10

| Peak Number | MLL1N | MLL1C |
|---|---|---|
| 293T-WT-shCtrl | 12460 | 10337 |
| 293T-TASP1KO-shCtrl | 16105 | 11080 |
| 293T-WT-shMLL1 | 2474 | 858 |
| 293T-TASP1KO-shMLL1 | 1711 | 707 |

Figure 12
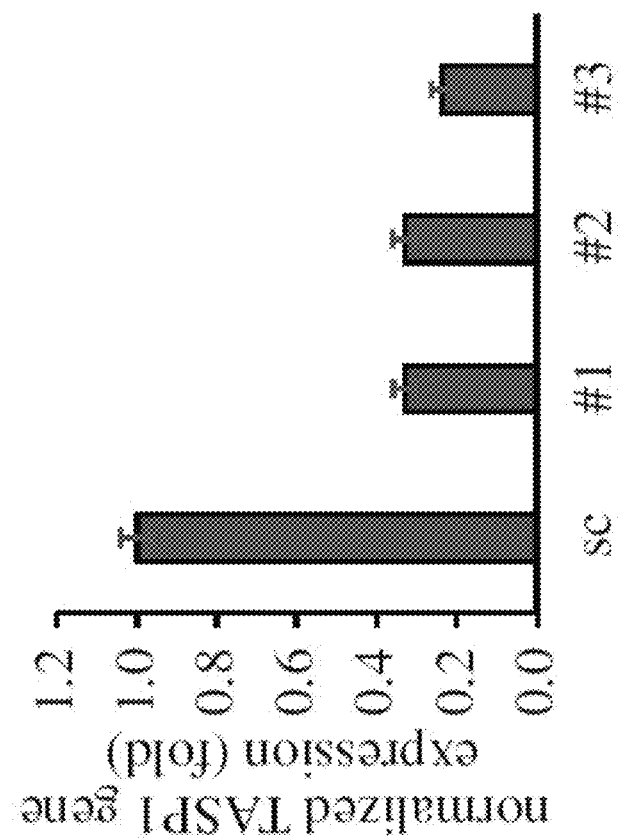
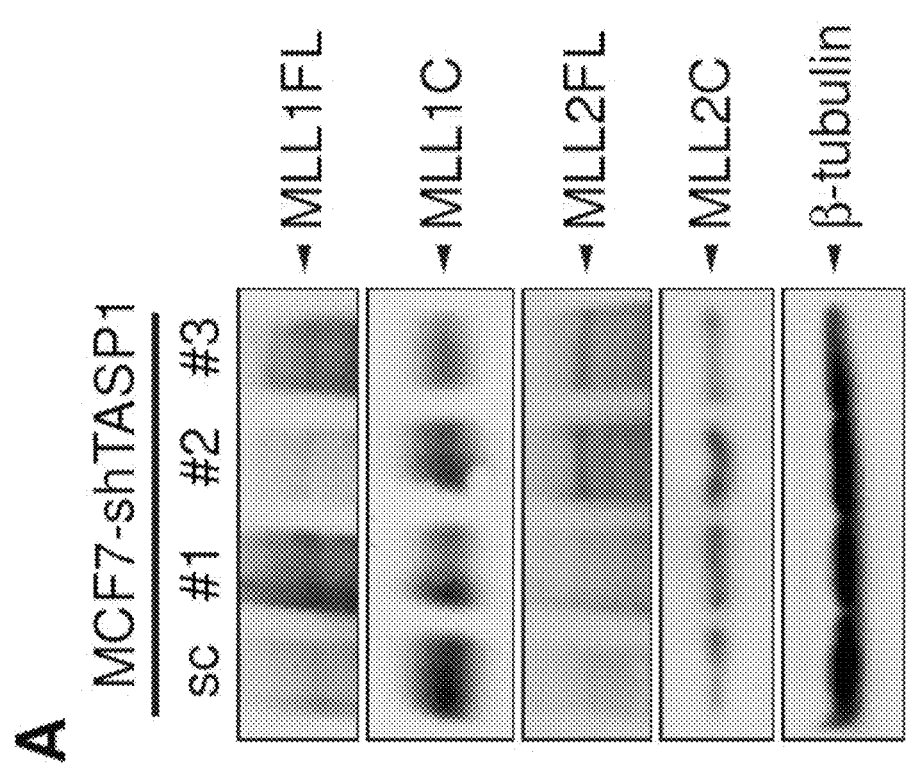

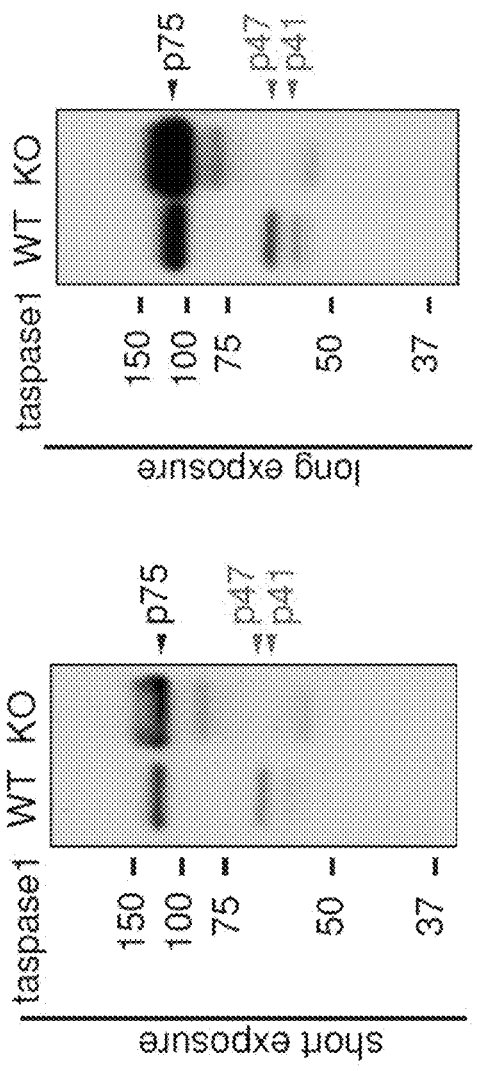
Figure 12 (cont.)

| MLL1 cleavage by taspase1: K¦SQLD/GVDDGt EsDtSVt | | | |
|---|---|---|---|
| t | s | t | t |
| 0.569 CKII | 0.544 CKII | 0.541 CKII | 0.441 CaM-II |
| 0.472 cdc2 | 0.452 CaM-II | 0.485 cdc2 | 0.425 cdc2 |
| 0.435 GSK3 | 0.441 GSK3 | 0.430 GSK3 | 0.412 GSK3 |
| 0.422 CKI | 0.429 cdc2 | 0.419 CaM-II | 0.388 CKI |
| 0.403 CaM-II | 0.392 p38MAPK | 0.405 CKI | 0.341 DNAPK |
| 0.379 DNAPK | 0.386 CKI | 0.338 DNAPK | 0.329 p38MAPK |
| | 0.377 DNAPK | | 0.319 PKG |
| | 0.334 PKA | | |

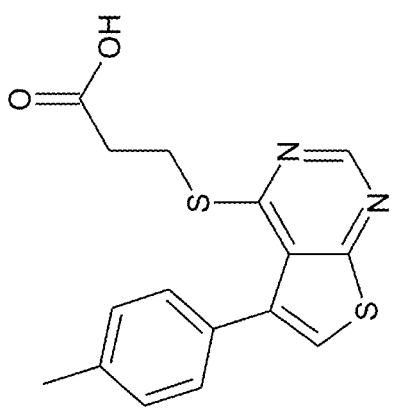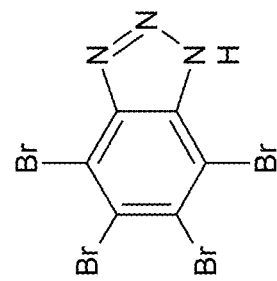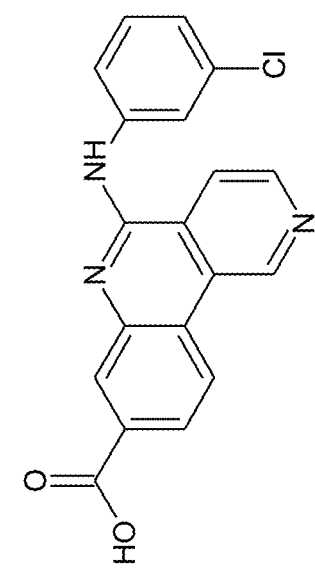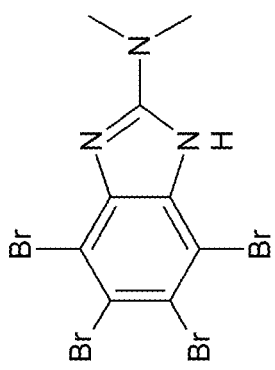
Figure 13 (cont.)

| compound | MW | IC50 |
|---|---|---|
| CX-4945 | 349.77 | 1 nM |
| TTP22 | 330.42 | 0.1 uM |
| DMAT | 476.79 | 0.13 uM |
| TBB | 434.71 | 1.6 uM |

SEQUENCE LISTING

<160> NUMBER OF SEQ ID NOS: 16

<210> SEQ ID NO 1
<211> LENGTH: 3969
<212> TYPE: PRT
<213> ORGANISM: Homo sapiens

<400> SEQUENCE: 1

Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Ala Pro Arg
            20                  25                  30

Gln Arg Val Pro Ala Leu Leu Leu Pro Pro Gly Pro Pro Val Gly Gly
        35                  40                  45

Gly Gly Pro Gly Ala Pro Pro Ser Pro Pro Ala Val Ala Ala Ala Ala

```
            50                  55                  60
Ala Ala Gly Ser Ser Gly Ala Gly Val Pro Gly Gly Ala Ala
65                  70                  75                  80

Ala Ser Ala Ala Ser Ser Ser Ala Ser Ser Ser Ser Ser Ser
                    85                  90                  95

Ser Ser Ala Ser Ser Gly Pro Ala Leu Leu Arg Val Gly Pro Gly Phe
                100                 105                 110

Asp Ala Ala Leu Gln Val Ser Ala Ala Ile Gly Thr Asn Leu Arg Arg
                115                 120                 125

Phe Arg Ala Val Phe Gly Glu Ser Gly Gly Gly Gly Ser Gly Glu
130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
                180                 185                 190

Pro Ser Val Phe Ser Pro Leu Asn Lys Ser Glu Thr Lys Ser Gly Asp
                195                 200                 205

Lys Ile Lys Lys Lys Asp Ser Lys Ser Ile Glu Lys Lys Arg Gly Arg
                210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
                245                 250                 255

Lys Arg Thr Pro Ser Ala Thr Phe Gln Gln Ala Thr Lys Ile Lys Lys
                260                 265                 270

Leu Arg Ala Gly Lys Leu Ser Pro Leu Lys Ser Lys Phe Lys Thr Gly
                275                 280                 285

Lys Leu Gln Ile Gly Arg Lys Gly Val Gln Ile Val Arg Arg Gly
                290                 295                 300

Arg Pro Pro Ser Thr Glu Arg Ile Lys Thr Pro Ser Gly Leu Leu Ile
305                 310                 315                 320

Asn Ser Glu Leu Glu Lys Pro Gln Lys Val Arg Lys Asp Lys Glu Gly
                325                 330                 335

Thr Pro Pro Leu Thr Lys Glu Asp Lys Thr Val Val Arg Gln Ser Pro
                340                 345                 350

Arg Arg Ile Lys Pro Val Arg Ile Ile Pro Ser Ser Lys Arg Thr Asp
                355                 360                 365

Ala Thr Ile Ala Lys Gln Leu Leu Gln Arg Ala Lys Lys Gly Ala Gln
                370                 375                 380

Lys Lys Ile Glu Lys Glu Ala Ala Gln Leu Gln Gly Arg Lys Val Lys
385                 390                 395                 400

Thr Gln Val Lys Asn Ile Arg Gln Phe Ile Met Pro Val Val Ser Ala
                405                 410                 415

Ile Ser Ser Arg Ile Ile Lys Thr Pro Arg Arg Phe Ile Glu Asp Glu
                420                 425                 430

Asp Tyr Asp Pro Pro Ile Lys Ile Ala Arg Leu Glu Ser Thr Pro Asn
                435                 440                 445

Ser Arg Phe Ser Ala Pro Ser Cys Gly Ser Ser Glu Lys Ser Ser Ala
                450                 455                 460

Ala Ser Gln His Ser Ser Gln Met Ser Ser Asp Ser Ser Arg Ser Ser
465                 470                 475                 480
```

```
Ser Pro Ser Val Asp Thr Ser Thr Asp Ser Gln Ala Ser Glu Glu Ile
            485                 490                 495

Gln Val Leu Pro Glu Arg Ser Asp Thr Pro Glu Val His Pro Pro
        500                 505                 510

Leu Pro Ile Ser Gln Ser Pro Glu Asn Glu Ser Asn Asp Arg Arg Ser
            515                 520                 525

Arg Arg Tyr Ser Val Ser Glu Arg Ser Phe Gly Ser Arg Thr Thr Lys
        530                 535                 540

Lys Leu Ser Thr Leu Gln Ser Ala Pro Gln Gln Thr Ser Ser Ser
545                 550                 555                 560

Pro Pro Pro Pro Leu Leu Thr Pro Pro Pro Leu Gln Pro Ala Ser
                565                 570                 575

Ser Ile Ser Asp His Thr Pro Trp Leu Met Pro Pro Thr Ile Pro Leu
            580                 585                 590

Ala Ser Pro Phe Leu Pro Ala Ser Thr Ala Pro Met Gln Gly Lys Arg
        595                 600                 605

Lys Ser Ile Leu Arg Glu Pro Thr Phe Arg Trp Thr Ser Leu Lys His
        610                 615                 620

Ser Arg Ser Glu Pro Gln Tyr Phe Ser Ser Ala Lys Tyr Ala Lys Glu
625                 630                 635                 640

Gly Leu Ile Arg Lys Pro Ile Phe Asp Asn Phe Arg Pro Pro Leu
                645                 650                 655

Thr Pro Glu Asp Val Gly Phe Ala Ser Gly Phe Ser Ala Ser Gly Thr
            660                 665                 670

Ala Ala Ser Ala Arg Leu Phe Ser Pro Leu His Ser Gly Thr Arg Phe
        675                 680                 685

Asp Met His Lys Arg Ser Pro Leu Leu Arg Ala Pro Arg Phe Thr Pro
        690                 695                 700

Ser Glu Ala His Ser Arg Ile Phe Glu Ser Val Thr Leu Pro Ser Asn
705                 710                 715                 720

Arg Thr Ser Ala Gly Thr Ser Ser Ser Gly Val Ser Asn Arg Lys Arg
                725                 730                 735

Lys Arg Lys Val Phe Ser Pro Ile Arg Ser Glu Pro Arg Ser Pro Ser
            740                 745                 750

His Ser Met Arg Thr Arg Ser Gly Arg Leu Ser Ser Ser Glu Leu Ser
        755                 760                 765

Pro Leu Thr Pro Pro Ser Ser Val Ser Ser Ser Leu Ser Ile Ser Val
        770                 775                 780

Ser Pro Leu Ala Thr Ser Ala Leu Asn Pro Thr Phe Thr Phe Pro Ser
785                 790                 795                 800

His Ser Leu Thr Gln Ser Gly Glu Ser Ala Glu Lys Asn Gln Arg Pro
                805                 810                 815

Arg Lys Gln Thr Ser Ala Pro Ala Glu Pro Phe Ser Ser Ser Ser Pro
            820                 825                 830

Thr Pro Leu Phe Pro Trp Phe Thr Pro Gly Ser Gln Thr Glu Arg Gly
        835                 840                 845

Arg Asn Lys Asp Lys Ala Pro Glu Glu Leu Ser Lys Asp Arg Asp Ala
        850                 855                 860

Asp Lys Ser Val Glu Lys Asp Lys Ser Arg Glu Arg Asp Arg Glu Arg
865                 870                 875                 880

Glu Lys Glu Asn Lys Arg Glu Ser Arg Lys Glu Lys Arg Lys Lys Gly
                885                 890                 895
```

```
Ser Glu Ile Gln Ser Ser Ser Ala Leu Tyr Pro Val Gly Arg Val Ser
            900                 905                 910
Lys Glu Lys Val Val Gly Glu Asp Val Ala Thr Ser Ser Ser Ala Lys
        915                 920                 925
Lys Ala Thr Gly Arg Lys Lys Ser Ser His Asp Ser Gly Thr Asp
    930                 935                 940
Ile Thr Ser Val Thr Leu Gly Asp Thr Thr Ala Val Lys Thr Lys Ile
945                 950                 955                 960
Leu Ile Lys Lys Gly Arg Gly Asn Leu Glu Lys Thr Asn Leu Asp Leu
                965                 970                 975
Gly Pro Thr Ala Pro Ser Leu Glu Lys Glu Lys Thr Leu Cys Leu Ser
            980                 985                 990
Thr Pro Ser Ser Ser Thr Val Lys His Ser Thr Ser Ser Ile Gly Ser
            995                 1000                1005
Met Leu Ala Gln Ala Asp Lys Leu Pro Met Thr Asp Lys Arg Val
    1010                1015                1020
Ala Ser Leu Leu Lys Lys Ala Lys Ala Gln Leu Cys Lys Ile Glu
    1025                1030                1035
Lys Ser Lys Ser Leu Lys Gln Thr Asp Gln Pro Lys Ala Gln Gly
    1040                1045                1050
Gln Glu Ser Asp Ser Ser Glu Thr Ser Val Arg Gly Pro Arg Ile
    1055                1060                1065
Lys His Val Cys Arg Arg Ala Ala Val Ala Leu Gly Arg Lys Arg
    1070                1075                1080
Ala Val Phe Pro Asp Asp Met Pro Thr Leu Ser Ala Leu Pro Trp
    1085                1090                1095
Glu Glu Arg Glu Lys Ile Leu Ser Ser Met Gly Asn Asp Asp Lys
    1100                1105                1110
Ser Ser Ile Ala Gly Ser Glu Asp Ala Glu Pro Leu Ala Pro Pro
    1115                1120                1125
Ile Lys Pro Ile Lys Pro Val Thr Arg Asn Lys Ala Pro Gln Glu
    1130                1135                1140
Pro Pro Val Lys Lys Gly Arg Arg Ser Arg Arg Cys Gly Gln Cys
    1145                1150                1155
Pro Gly Cys Gln Val Pro Glu Asp Cys Gly Val Cys Thr Asn Cys
    1160                1165                1170
Leu Asp Lys Pro Lys Phe Gly Gly Arg Asn Ile Lys Lys Gln Cys
    1175                1180                1185
Cys Lys Met Arg Lys Cys Gln Asn Leu Gln Trp Met Pro Ser Lys
    1190                1195                1200
Ala Tyr Leu Gln Lys Gln Ala Lys Ala Val Lys Lys Lys Glu Lys
    1205                1210                1215
Lys Ser Lys Thr Ser Glu Lys Lys Asp Ser Lys Glu Ser Ser Val
    1220                1225                1230
Val Lys Asn Val Val Asp Ser Ser Gln Lys Pro Thr Pro Ser Ala
    1235                1240                1245
Arg Glu Asp Pro Ala Pro Lys Lys Ser Ser Ser Glu Pro Pro Pro
    1250                1255                1260
Arg Lys Pro Val Glu Glu Lys Ser Glu Glu Gly Asn Val Ser Ala
    1265                1270                1275
Pro Gly Pro Glu Ser Lys Gln Ala Thr Thr Pro Ala Ser Arg Lys
    1280                1285                1290
Ser Ser Lys Gln Val Ser Gln Pro Ala Leu Val Ile Pro Pro Gln
```

```
            1295                1300                1305

Pro  Pro  Thr  Thr  Gly  Pro  Pro  Arg  Lys  Glu  Val  Pro  Lys  Thr  Thr
     1310                1315                1320

Pro  Ser  Glu  Pro  Lys  Lys  Lys  Gln  Pro  Pro  Pro  Glu  Ser  Gly
     1325                1330                1335

Pro  Glu  Gln  Ser  Lys  Gln  Lys  Lys  Val  Ala  Pro  Arg  Pro  Ser  Ile
     1340                1345                1350

Pro  Val  Lys  Gln  Lys  Pro  Lys  Glu  Lys  Glu  Lys  Pro  Pro  Pro  Val
     1355                1360                1365

Asn  Lys  Gln  Glu  Asn  Ala  Gly  Thr  Leu  Asn  Ile  Leu  Ser  Thr  Leu
     1370                1375                1380

Ser  Asn  Gly  Asn  Ser  Ser  Lys  Gln  Lys  Ile  Pro  Ala  Asp  Gly  Val
     1385                1390                1395

His  Arg  Ile  Arg  Val  Asp  Phe  Lys  Glu  Asp  Cys  Glu  Ala  Glu  Asn
     1400                1405                1410

Val  Trp  Glu  Met  Gly  Gly  Leu  Gly  Ile  Leu  Thr  Ser  Val  Pro  Ile
     1415                1420                1425

Thr  Pro  Arg  Val  Val  Cys  Phe  Leu  Cys  Ala  Ser  Ser  Gly  His  Val
     1430                1435                1440

Glu  Phe  Val  Tyr  Cys  Gln  Val  Cys  Cys  Glu  Pro  Phe  His  Lys  Phe
     1445                1450                1455

Cys  Leu  Glu  Glu  Asn  Glu  Arg  Pro  Leu  Glu  Asp  Gln  Leu  Glu  Asn
     1460                1465                1470

Trp  Cys  Cys  Arg  Arg  Cys  Lys  Phe  Cys  His  Val  Cys  Gly  Arg  Gln
     1475                1480                1485

His  Gln  Ala  Thr  Lys  Gln  Leu  Leu  Glu  Cys  Asn  Lys  Cys  Arg  Asn
     1490                1495                1500

Ser  Tyr  His  Pro  Glu  Cys  Leu  Gly  Pro  Asn  Tyr  Pro  Thr  Lys  Pro
     1505                1510                1515

Thr  Lys  Lys  Lys  Lys  Val  Trp  Ile  Cys  Thr  Lys  Cys  Val  Arg  Cys
     1520                1525                1530

Lys  Ser  Cys  Gly  Ser  Thr  Thr  Pro  Gly  Lys  Gly  Trp  Asp  Ala  Gln
     1535                1540                1545

Trp  Ser  His  Asp  Phe  Ser  Leu  Cys  His  Asp  Cys  Ala  Lys  Leu  Phe
     1550                1555                1560

Ala  Lys  Gly  Asn  Phe  Cys  Pro  Leu  Cys  Asp  Lys  Cys  Tyr  Asp  Asp
     1565                1570                1575

Asp  Asp  Tyr  Glu  Ser  Lys  Met  Met  Gln  Cys  Gly  Lys  Cys  Asp  Arg
     1580                1585                1590

Trp  Val  His  Ser  Lys  Cys  Glu  Asn  Leu  Ser  Asp  Glu  Met  Tyr  Glu
     1595                1600                1605

Ile  Leu  Ser  Asn  Leu  Pro  Glu  Ser  Val  Ala  Tyr  Thr  Cys  Val  Asn
     1610                1615                1620

Cys  Thr  Glu  Arg  His  Pro  Ala  Glu  Trp  Arg  Leu  Ala  Leu  Glu  Lys
     1625                1630                1635

Glu  Leu  Gln  Ile  Ser  Leu  Lys  Gln  Val  Leu  Thr  Ala  Leu  Leu  Asn
     1640                1645                1650

Ser  Arg  Thr  Thr  Ser  His  Leu  Leu  Arg  Tyr  Arg  Gln  Ala  Ala  Lys
     1655                1660                1665

Pro  Pro  Asp  Leu  Asn  Pro  Glu  Thr  Glu  Glu  Ser  Ile  Pro  Ser  Arg
     1670                1675                1680

Ser  Ser  Pro  Glu  Gly  Pro  Asp  Pro  Pro  Val  Leu  Thr  Glu  Val  Ser
     1685                1690                1695
```

-continued

```
Lys Gln Asp Asp Gln Gln Pro Leu Asp Leu Glu Gly Val Lys Arg
    1700                1705                1710
Lys Met Asp Gln Gly Asn Tyr Thr Ser Val Leu Glu Phe Ser Asp
    1715                1720                1725
Asp Ile Val Lys Ile Ile Gln Ala Ala Ile Asn Ser Asp Gly Gly
    1730                1735                1740
Gln Pro Glu Ile Lys Lys Ala Asn Ser Met Val Lys Ser Phe Phe
    1745                1750                1755
Ile Arg Gln Met Glu Arg Val Phe Pro Trp Phe Ser Val Lys Lys
    1760                1765                1770
Ser Arg Phe Trp Glu Pro Asn Lys Val Ser Ser Asn Ser Gly Met
    1775                1780                1785
Leu Pro Asn Ala Val Leu Pro Pro Ser Leu Asp His Asn Tyr Ala
    1790                1795                1800
Gln Trp Gln Glu Arg Glu Glu Asn Ser His Thr Glu Gln Pro Pro
    1805                1810                1815
Leu Met Lys Lys Ile Ile Pro Ala Pro Lys Pro Lys Gly Pro Gly
    1820                1825                1830
Glu Pro Asp Ser Pro Thr Pro Leu His Pro Pro Thr Pro Pro Ile
    1835                1840                1845
Leu Ser Thr Asp Arg Ser Arg Glu Asp Ser Pro Glu Leu Asn Pro
    1850                1855                1860
Pro Pro Gly Ile Glu Asp Asn Arg Gln Cys Ala Leu Cys Leu Thr
    1865                1870                1875
Tyr Gly Asp Asp Ser Ala Asn Asp Ala Gly Arg Leu Leu Tyr Ile
    1880                1885                1890
Gly Gln Asn Glu Trp Thr His Val Asn Cys Ala Leu Trp Ser Ala
    1895                1900                1905
Glu Val Phe Glu Asp Asp Asp Gly Ser Leu Lys Asn Val His Met
    1910                1915                1920
Ala Val Ile Arg Gly Lys Gln Leu Arg Cys Glu Phe Cys Gln Lys
    1925                1930                1935
Pro Gly Ala Thr Val Gly Cys Cys Leu Thr Ser Cys Thr Ser Asn
    1940                1945                1950
Tyr His Phe Met Cys Ser Arg Ala Lys Asn Cys Val Phe Leu Asp
    1955                1960                1965
Asp Lys Lys Val Tyr Cys Gln Arg His Arg Asp Leu Ile Lys Gly
    1970                1975                1980
Glu Val Val Pro Glu Asn Gly Phe Glu Val Phe Arg Arg Val Phe
    1985                1990                1995
Val Asp Phe Glu Gly Ile Ser Leu Arg Arg Lys Phe Leu Asn Gly
    2000                2005                2010
Leu Glu Pro Glu Asn Ile His Met Met Ile Gly Ser Met Thr Ile
    2015                2020                2025
Asp Cys Leu Gly Ile Leu Asn Asp Leu Ser Asp Cys Glu Asp Lys
    2030                2035                2040
Leu Phe Pro Ile Gly Tyr Gln Cys Ser Arg Val Tyr Trp Ser Thr
    2045                2050                2055
Thr Asp Ala Arg Lys Arg Cys Val Tyr Thr Cys Lys Ile Val Glu
    2060                2065                2070
Cys Arg Pro Pro Val Val Glu Pro Asp Ile Asn Ser Thr Val Glu
    2075                2080                2085
```

-continued

```
His Asp Glu Asn Arg Thr Ile Ala His Ser Pro Thr Ser Phe Thr
    2090                2095                2100

Glu Ser Ser Ser Lys Glu Ser Gln Asn Thr Ala Glu Ile Ile Ser
    2105                2110                2115

Pro Pro Ser Pro Asp Arg Pro Pro His Ser Gln Thr Ser Gly Ser
    2120                2125                2130

Cys Tyr Tyr His Val Ile Ser Lys Val Pro Arg Ile Arg Thr Pro
    2135                2140                2145

Ser Tyr Ser Pro Thr Gln Arg Ser Pro Gly Cys Arg Pro Leu Pro
    2150                2155                2160

Ser Ala Gly Ser Pro Thr Pro Thr Thr His Glu Ile Val Thr Val
    2165                2170                2175

Gly Asp Pro Leu Leu Ser Ser Gly Leu Arg Ser Ile Gly Ser Arg
    2180                2185                2190

Arg His Ser Thr Ser Ser Leu Ser Pro Gln Arg Ser Lys Leu Arg
    2195                2200                2205

Ile Met Ser Pro Met Arg Thr Gly Asn Thr Tyr Ser Arg Asn Asn
    2210                2215                2220

Val Ser Ser Val Ser Thr Thr Gly Thr Ala Thr Asp Leu Glu Ser
    2225                2230                2235

Ser Ala Lys Val Val Asp His Val Leu Gly Pro Leu Asn Ser Ser
    2240                2245                2250

Thr Ser Leu Gly Gln Asn Thr Ser Thr Ser Ser Asn Leu Gln Arg
    2255                2260                2265

Thr Val Val Thr Val Gly Asn Lys Asn Ser His Leu Asp Gly Ser
    2270                2275                2280

Ser Ser Ser Glu Met Lys Gln Ser Ser Ala Ser Asp Leu Val Ser
    2285                2290                2295

Lys Ser Ser Ser Leu Lys Gly Glu Lys Thr Lys Val Leu Ser Ser
    2300                2305                2310

Lys Ser Ser Glu Gly Ser Ala His Asn Val Ala Tyr Pro Gly Ile
    2315                2320                2325

Pro Lys Leu Ala Pro Gln Val His Asn Thr Thr Ser Arg Glu Leu
    2330                2335                2340

Asn Val Ser Lys Ile Gly Ser Phe Ala Glu Pro Ser Ser Val Ser
    2345                2350                2355

Phe Ser Ser Lys Glu Ala Leu Ser Phe Pro His Leu His Leu Arg
    2360                2365                2370

Gly Gln Arg Asn Asp Arg Asp Gln His Thr Asp Ser Thr Gln Ser
    2375                2380                2385

Ala Asn Ser Ser Pro Asp Glu Asp Thr Glu Val Lys Thr Leu Lys
    2390                2395                2400

Leu Ser Gly Met Ser Asn Arg Ser Ser Ile Ile Asn Glu His Met
    2405                2410                2415

Gly Ser Ser Ser Arg Asp Arg Arg Gln Lys Gly Lys Lys Ser Cys
    2420                2425                2430

Lys Glu Thr Phe Lys Glu Lys His Ser Ser Lys Ser Phe Leu Glu
    2435                2440                2445

Pro Gly Gln Val Thr Thr Gly Glu Glu Gly Asn Leu Lys Pro Glu
    2450                2455                2460

Phe Met Asp Glu Val Leu Thr Pro Glu Tyr Met Gly Gln Arg Pro
    2465                2470                2475

Cys Asn Asn Val Ser Ser Asp Lys Ile Gly Asp Lys Gly Leu Ser
```

```
            2480                2485                2490
Met Pro Gly Val Pro Lys Ala Pro Pro Met Gln Val Glu Gly Ser
    2495                2500                2505

Ala Lys Glu Leu Gln Ala Pro Arg Lys Arg Thr Val Lys Val Thr
    2510                2515                2520

Leu Thr Pro Leu Lys Met Glu Asn Glu Ser Gln Ser Lys Asn Ala
    2525                2530                2535

Leu Lys Glu Ser Ser Pro Ala Ser Pro Leu Gln Ile Glu Ser Thr
    2540                2545                2550

Ser Pro Thr Glu Pro Ile Ser Ala Ser Glu Asn Pro Gly Asp Gly
    2555                2560                2565

Pro Val Ala Gln Pro Ser Pro Asn Asn Thr Ser Cys Gln Asp Ser
    2570                2575                2580

Gln Ser Asn Asn Tyr Gln Asn Leu Pro Val Gln Asp Arg Asn Leu
    2585                2590                2595

Met Leu Pro Asp Gly Pro Lys Pro Gln Glu Asp Gly Ser Phe Lys
    2600                2605                2610

Arg Arg Tyr Pro Arg Arg Ser Ala Arg Ala Arg Ser Asn Met Phe
    2615                2620                2625

Phe Gly Leu Thr Pro Leu Tyr Gly Val Arg Ser Tyr Gly Glu Glu
    2630                2635                2640

Asp Ile Pro Phe Tyr Ser Ser Ser Thr Gly Lys Lys Arg Gly Lys
    2645                2650                2655

Arg Ser Ala Glu Gly Gln Val Asp Gly Ala Asp Leu Ser Thr
    2660                2665                2670

Ser Asp Glu Asp Asp Leu Tyr Tyr Tyr Asn Phe Thr Arg Thr Val
    2675                2680                2685

Ile Ser Ser Gly Gly Glu Glu Arg Leu Ala Ser His Asn Leu Phe
    2690                2695                2700

Arg Glu Glu Glu Gln Cys Asp Leu Pro Lys Ile Ser Gln Leu Asp
    2705                2710                2715

Gly Val Asp Asp Gly Thr Glu Ser Asp Thr Ser Val Thr Ala Thr
    2720                2725                2730

Thr Arg Lys Ser Ser Gln Ile Pro Lys Arg Asn Gly Lys Glu Asn
    2735                2740                2745

Gly Thr Glu Asn Leu Lys Ile Asp Arg Pro Glu Asp Ala Gly Glu
    2750                2755                2760

Lys Glu His Val Thr Lys Ser Ser Val Gly His Lys Asn Glu Pro
    2765                2770                2775

Lys Met Asp Asn Cys His Ser Val Ser Arg Val Lys Thr Gln Gly
    2780                2785                2790

Gln Asp Ser Leu Glu Ala Gln Leu Ser Ser Leu Glu Ser Ser Arg
    2795                2800                2805

Arg Val His Thr Ser Thr Pro Ser Asp Lys Asn Leu Leu Asp Thr
    2810                2815                2820

Tyr Asn Thr Glu Leu Leu Lys Ser Asp Ser Asp Asn Asn Asn Ser
    2825                2830                2835

Asp Asp Cys Gly Asn Ile Leu Pro Ser Asp Ile Met Asp Phe Val
    2840                2845                2850

Leu Lys Asn Thr Pro Ser Met Gln Ala Leu Gly Glu Ser Pro Glu
    2855                2860                2865

Ser Ser Ser Ser Glu Leu Leu Asn Leu Gly Glu Gly Leu Gly Leu
    2870                2875                2880
```

```
Asp Ser Asn Arg Glu Lys Asp Met Gly Leu Phe Glu Val Phe Ser
        2885            2890            2895

Gln Gln Leu Pro Thr Thr Glu Pro Val Asp Ser Ser Val Ser Ser
        2900            2905            2910

Ser Ile Ser Ala Glu Glu Gln Phe Glu Leu Pro Leu Glu Leu Pro
        2915            2920            2925

Ser Asp Leu Ser Val Leu Thr Thr Arg Ser Pro Thr Val Pro Ser
        2930            2935            2940

Gln Asn Pro Ser Arg Leu Ala Val Ile Ser Asp Ser Gly Glu Lys
        2945            2950            2955

Arg Val Thr Ile Thr Glu Lys Ser Val Ala Ser Ser Glu Ser Asp
        2960            2965            2970

Pro Ala Leu Leu Ser Pro Gly Val Asp Pro Thr Pro Glu Gly His
        2975            2980            2985

Met Thr Pro Asp His Phe Ile Gln Gly His Met Asp Ala Asp His
        2990            2995            3000

Ile Ser Ser Pro Pro Cys Gly Ser Val Glu Gln Gly His Gly Asn
        3005            3010            3015

Asn Gln Asp Leu Thr Arg Asn Ser Ser Thr Pro Gly Leu Gln Val
        3020            3025            3030

Pro Val Ser Pro Thr Val Pro Ile Gln Asn Gln Lys Tyr Val Pro
        3035            3040            3045

Asn Ser Thr Asp Ser Pro Gly Pro Ser Gln Ile Ser Asn Ala Ala
        3050            3055            3060

Val Gln Thr Thr Pro Pro His Leu Lys Pro Ala Thr Glu Lys Leu
        3065            3070            3075

Ile Val Val Asn Gln Asn Met Gln Pro Leu Tyr Val Leu Gln Thr
        3080            3085            3090

Leu Pro Asn Gly Val Thr Gln Lys Ile Gln Leu Thr Ser Ser Val
        3095            3100            3105

Ser Ser Thr Pro Ser Val Met Glu Thr Asn Thr Ser Val Leu Gly
        3110            3115            3120

Pro Met Gly Gly Gly Leu Thr Leu Thr Thr Gly Leu Asn Pro Ser
        3125            3130            3135

Leu Pro Thr Ser Gln Ser Leu Phe Pro Ser Ala Ser Lys Gly Leu
        3140            3145            3150

Leu Pro Met Ser His His Gln His Leu His Ser Phe Pro Ala Ala
        3155            3160            3165

Thr Gln Ser Ser Phe Pro Pro Asn Ile Ser Asn Pro Pro Ser Gly
        3170            3175            3180

Leu Leu Ile Gly Val Gln Pro Pro Pro Asp Pro Gln Leu Leu Val
        3185            3190            3195

Ser Glu Ser Ser Gln Arg Thr Asp Leu Ser Thr Thr Val Ala Thr
        3200            3205            3210

Pro Ser Ser Gly Leu Lys Lys Arg Pro Ile Ser Arg Leu Gln Thr
        3215            3220            3225

Arg Lys Asn Lys Lys Leu Ala Pro Ser Ser Thr Pro Ser Asn Ile
        3230            3235            3240

Ala Pro Ser Asp Val Val Ser Asn Met Thr Leu Ile Asn Phe Thr
        3245            3250            3255

Pro Ser Gln Leu Pro Asn His Pro Ser Leu Leu Asp Leu Gly Ser
        3260            3265            3270
```

```
Leu Asn Thr Ser Ser His Arg Thr Val Pro Asn Ile Ile Lys Arg
3275                3280                3285

Ser Lys Ser Ser Ile Met Tyr Phe Glu Pro Ala Pro Leu Leu Pro
3290                3295                3300

Gln Ser Val Gly Gly Thr Ala Ala Thr Ala Ala Gly Thr Ser Thr
3305                3310                3315

Ile Ser Gln Asp Thr Ser His Leu Thr Ser Gly Ser Val Ser Gly
3320                3325                3330

Leu Ala Ser Ser Ser Val Leu Asn Val Val Ser Met Gln Thr
3335                3340                3345

Thr Thr Thr Pro Thr Ser Ser Ala Ser Val Pro Gly His Val Thr
3350                3355                3360

Leu Thr Asn Pro Arg Leu Leu Gly Thr Pro Asp Ile Gly Ser Ile
3365                3370                3375

Ser Asn Leu Leu Ile Lys Ala Ser Gln Gln Ser Leu Gly Ile Gln
3380                3385                3390

Asp Gln Pro Val Ala Leu Pro Pro Ser Ser Gly Met Phe Pro Gln
3395                3400                3405

Leu Gly Thr Ser Gln Thr Pro Ser Thr Ala Ala Ile Thr Ala Ala
3410                3415                3420

Ser Ser Ile Cys Val Leu Pro Ser Thr Gln Thr Thr Gly Ile Thr
3425                3430                3435

Ala Ala Ser Pro Ser Gly Glu Ala Asp Glu His Tyr Gln Leu Gln
3440                3445                3450

His Val Asn Gln Leu Leu Ala Ser Lys Thr Gly Ile His Ser Ser
3455                3460                3465

Gln Arg Asp Leu Asp Ser Ala Ser Gly Pro Gln Val Ser Asn Phe
3470                3475                3480

Thr Gln Thr Val Asp Ala Pro Asn Ser Met Gly Leu Glu Gln Asn
3485                3490                3495

Lys Ala Leu Ser Ser Ala Val Gln Ala Ser Pro Thr Ser Pro Gly
3500                3505                3510

Gly Ser Pro Ser Ser Pro Ser Gly Gln Arg Ser Ala Ser Pro
3515                3520                3525

Ser Val Pro Gly Pro Thr Lys Pro Lys Pro Lys Thr Lys Arg Phe
3530                3535                3540

Gln Leu Pro Leu Asp Lys Gly Asn Gly Lys Lys His Lys Val Ser
3545                3550                3555

His Leu Arg Thr Ser Ser Ser Glu Ala His Ile Pro Asp Gln Glu
3560                3565                3570

Thr Thr Ser Leu Thr Ser Gly Thr Gly Thr Pro Gly Ala Glu Ala
3575                3580                3585

Glu Gln Gln Asp Thr Ala Ser Val Glu Gln Ser Ser Gln Lys Glu
3590                3595                3600

Cys Gly Gln Pro Ala Gly Gln Val Ala Val Leu Pro Glu Val Gln
3605                3610                3615

Val Thr Gln Asn Pro Ala Asn Glu Gln Glu Ser Ala Glu Pro Lys
3620                3625                3630

Thr Val Glu Glu Glu Glu Ser Asn Phe Ser Ser Pro Leu Met Leu
3635                3640                3645

Trp Leu Gln Gln Glu Gln Lys Arg Lys Glu Ser Ile Thr Glu Lys
3650                3655                3660

Lys Pro Lys Lys Gly Leu Val Phe Glu Ile Ser Ser Asp Asp Gly
```

```
                3665                3670                3675

Phe Gln Ile Cys Ala Glu Ser Ile Glu Asp Ala Trp Lys Ser Leu
            3680                3685                3690

Thr Asp Lys Val Gln Glu Arg Ser Asn Ala Arg Leu Lys Gln
3695                3700                3705

Leu Ser Phe Ala Gly Val Asn Gly Leu Arg Met Leu Gly Ile Leu
        3710                3715                3720

His Asp Ala Val Val Phe Leu Ile Glu Gln Leu Ser Gly Ala Lys
    3725                3730                3735

His Cys Arg Asn Tyr Lys Phe Arg Phe His Lys Pro Glu Glu Ala
3740                3745                3750

Asn Glu Pro Pro Leu Asn Pro His Gly Ser Ala Arg Ala Glu Val
        3755                3760                3765

His Leu Arg Lys Ser Ala Phe Asp Met Phe Asn Phe Leu Ala Ser
    3770                3775                3780

Lys His Arg Gln Pro Pro Glu Tyr Asn Pro Asn Asp Glu Glu Glu
3785                3790                3795

Glu Glu Val Gln Leu Lys Ser Ala Arg Arg Ala Thr Ser Met Asp
        3800                3805                3810

Leu Pro Met Pro Met Arg Phe Arg His Leu Lys Lys Thr Ser Lys
    3815                3820                3825

Glu Ala Val Gly Val Tyr Arg Ser Pro Ile His Gly Arg Gly Leu
3830                3835                3840

Phe Cys Lys Arg Asn Ile Asp Ala Gly Glu Met Val Ile Glu Tyr
        3845                3850                3855

Ala Gly Asn Val Ile Arg Ser Ile Gln Thr Asp Lys Arg Glu Lys
    3860                3865                3870

Tyr Tyr Asp Ser Lys Gly Ile Gly Cys Tyr Met Phe Arg Ile Asp
3875                3880                3885

Asp Ser Glu Val Val Asp Ala Thr Met His Gly Asn Ala Ala Arg
        3890                3895                3900

Phe Ile Asn His Ser Cys Glu Pro Asn Cys Tyr Ser Arg Val Ile
    3905                3910                3915

Asn Ile Asp Gly Gln Lys His Ile Val Ile Phe Ala Met Arg Lys
3920                3925                3930

Ile Tyr Arg Gly Glu Glu Leu Thr Tyr Asp Tyr Lys Phe Pro Ile
        3935                3940                3945

Glu Asp Ala Ser Asn Lys Leu Pro Cys Asn Cys Gly Ala Lys Lys
    3950                3955                3960

Cys Arg Lys Phe Leu Asn
3965

<210> SEQ ID NO 2
<211> LENGTH: 3931
<212> TYPE: PRT
<213> ORGANISM: Homo sapiens

<400> SEQUENCE: 2

Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Ala Pro Arg
                20                  25                  30

Gln Arg Val Pro Ala Leu Leu Leu Pro Pro Gly Pro Pro Val Gly Gly
        35                  40                  45
```

-continued

```
Gly Gly Pro Gly Ala Pro Pro Ser Pro Pro Ala Val Ala Ala Ala
     50                  55                  60
Ala Ala Ala Gly Ser Ser Gly Ala Gly Val Pro Gly Gly Ala Ala Ala
 65              70                  75                  80
Ala Ser Ala Ala Ser Ser Ser Ser Ala Ser Ser Ser Ser Ser Ser
             85                  90                  95
Ser Ser Ala Ser Ser Gly Pro Ala Leu Leu Arg Val Gly Pro Gly Phe
         100                 105                 110
Asp Ala Ala Leu Gln Val Ser Ala Ala Ile Gly Thr Asn Leu Arg Arg
             115                 120                 125
Phe Arg Ala Val Phe Gly Glu Ser Gly Gly Gly Gly Ser Gly Glu
 130                 135                 140
Asp Glu Gln Phe Leu Gly Phe Gly Ser Asp Glu Glu Val Arg Val Arg
 145                 150                 155                 160
Ser Pro Thr Arg Ser Pro Ser Val Lys Thr Ser Pro Arg Lys Pro Arg
                 165                 170                 175
Gly Arg Pro Arg Ser Gly Ser Asp Arg Asn Ser Ala Ile Leu Ser Asp
                 180                 185                 190
Pro Ser Val Phe Ser Pro Leu Asn Lys Ser Glu Thr Lys Ser Gly Asp
             195                 200                 205
Lys Ile Lys Lys Lys Asp Ser Lys Ser Ile Glu Lys Lys Arg Gly Arg
 210                 215                 220
Pro Pro Thr Phe Pro Gly Val Lys Ile Lys Ile Thr His Gly Lys Asp
 225                 230                 235                 240
Ile Ser Glu Leu Pro Lys Gly Asn Lys Glu Asp Ser Leu Lys Lys Ile
                 245                 250                 255
Lys Arg Thr Pro Ser Ala Thr Phe Gln Gln Ala Thr Lys Ile Lys Lys
                 260                 265                 270
Leu Arg Ala Gly Lys Leu Ser Pro Leu Lys Ser Lys Phe Lys Thr Gly
             275                 280                 285
Lys Leu Gln Ile Gly Arg Lys Gly Val Gln Ile Val Arg Arg Gly
 290                 295                 300
Arg Pro Pro Ser Thr Glu Arg Ile Lys Thr Pro Ser Gly Leu Leu Ile
 305                 310                 315                 320
Asn Ser Glu Leu Glu Lys Pro Gln Lys Val Arg Lys Asp Lys Glu Gly
                 325                 330                 335
Thr Pro Pro Leu Thr Lys Glu Asp Lys Thr Val Val Arg Gln Ser Pro
             340                 345                 350
Arg Arg Ile Lys Pro Val Arg Ile Ile Pro Ser Ser Lys Arg Thr Asp
             355                 360                 365
Ala Thr Ile Ala Lys Gln Leu Leu Gln Arg Ala Lys Lys Gly Ala Gln
 370                 375                 380
Lys Lys Ile Glu Lys Glu Ala Ala Gln Leu Gln Gly Arg Lys Val Lys
 385                 390                 395                 400
Thr Gln Val Lys Asn Ile Arg Gln Phe Ile Met Pro Val Val Ser Ala
                 405                 410                 415
Ile Ser Ser Arg Ile Ile Lys Thr Pro Arg Arg Phe Ile Glu Asp Glu
             420                 425                 430
Asp Tyr Asp Pro Pro Ile Lys Ile Ala Arg Leu Glu Ser Thr Pro Asn
             435                 440                 445
Ser Arg Phe Ser Ala Pro Ser Cys Gly Ser Ser Glu Lys Ser Ser Ala
 450                 455                 460
Ala Ser Gln His Ser Ser Gln Met Ser Ser Asp Ser Ser Arg Ser Ser
```

```
            465                 470                 475                 480
        Ser Pro Ser Val Asp Thr Ser Thr Asp Ser Gln Ala Ser Glu Glu Ile
                        485                 490                 495
        Gln Val Leu Pro Glu Glu Arg Ser Asp Thr Pro Glu Val His Pro Pro
                    500                 505                 510
        Leu Pro Ile Ser Gln Ser Pro Glu Asn Glu Ser Asn Asp Arg Arg Ser
                515                 520                 525
        Arg Arg Tyr Ser Val Ser Glu Arg Ser Phe Gly Ser Arg Thr Thr Lys
            530                 535                 540
        Lys Leu Ser Thr Leu Gln Ser Ala Pro Gln Gln Thr Ser Ser Ser
        545                 550                 555                 560
        Pro Pro Pro Pro Leu Leu Thr Pro Pro Pro Leu Gln Pro Ala Ser
                        565                 570                 575
        Ser Ile Ser Asp His Thr Pro Trp Leu Met Pro Thr Ile Pro Leu
                        580                 585                 590
        Ala Ser Pro Phe Leu Pro Ala Ser Thr Ala Pro Met Gln Gly Lys Arg
                    595                 600                 605
        Lys Ser Ile Leu Arg Glu Pro Thr Phe Arg Trp Thr Ser Leu Lys His
                610                 615                 620
        Ser Arg Ser Glu Pro Gln Tyr Phe Ser Ser Ala Lys Tyr Ala Lys Glu
        625                 630                 635                 640
        Gly Leu Ile Arg Lys Pro Ile Phe Asp Asn Phe Arg Pro Pro Pro Leu
                        645                 650                 655
        Thr Pro Glu Asp Val Gly Phe Ala Ser Gly Phe Ser Ala Ser Gly Thr
                    660                 665                 670
        Ala Ala Ser Ala Arg Leu Phe Ser Pro Leu His Ser Gly Thr Arg Phe
                675                 680                 685
        Asp Met His Lys Arg Ser Pro Leu Leu Arg Ala Pro Arg Phe Thr Pro
            690                 695                 700
        Ser Glu Ala His Ser Arg Ile Phe Glu Ser Val Thr Leu Pro Ser Asn
        705                 710                 715                 720
        Arg Thr Ser Ala Gly Thr Ser Ser Ser Gly Val Ser Asn Arg Lys Arg
                        725                 730                 735
        Lys Arg Lys Val Phe Ser Pro Ile Arg Ser Glu Pro Arg Ser Pro Ser
                        740                 745                 750
        His Ser Met Arg Thr Arg Ser Gly Arg Leu Ser Ser Ser Glu Leu Ser
                    755                 760                 765
        Pro Leu Thr Pro Pro Ser Ser Val Ser Ser Ser Leu Ser Ile Ser Val
                770                 775                 780
        Ser Pro Leu Ala Thr Ser Ala Leu Asn Pro Thr Phe Thr Phe Pro Ser
        785                 790                 795                 800
        His Ser Leu Thr Gln Ser Gly Glu Ser Ala Glu Lys Asn Gln Arg Pro
                    805                 810                 815
        Arg Lys Gln Thr Ser Ala Pro Ala Glu Pro Phe Ser Ser Ser Ser Pro
                820                 825                 830
        Thr Pro Leu Phe Pro Trp Phe Thr Pro Gly Ser Gln Thr Glu Arg Gly
                    835                 840                 845
        Arg Asn Lys Asp Lys Ala Pro Glu Glu Leu Ser Lys Asp Arg Asp Ala
                850                 855                 860
        Asp Lys Ser Val Glu Lys Asp Lys Ser Arg Glu Arg Asp Arg Glu Arg
        865                 870                 875                 880
        Glu Lys Glu Asn Lys Arg Glu Ser Arg Lys Glu Lys Arg Lys Lys Gly
                        885                 890                 895
```

```
Ser Glu Ile Gln Ser Ser Ser Ala Leu Tyr Pro Val Gly Arg Val Ser
            900                 905                 910

Lys Glu Lys Val Val Gly Glu Asp Val Ala Thr Ser Ser Ala Lys
        915                 920                 925

Lys Ala Thr Gly Arg Lys Lys Ser Ser His Asp Ser Gly Thr Asp
        930                 935                 940

Ile Thr Ser Val Thr Leu Gly Asp Thr Ala Val Lys Thr Lys Ile
945                 950                 955                 960

Leu Ile Lys Lys Gly Arg Gly Asn Leu Glu Lys Thr Asn Leu Asp Leu
                965                 970                 975

Gly Pro Thr Ala Pro Ser Leu Glu Lys Glu Lys Thr Leu Cys Leu Ser
            980                 985                 990

Thr Pro Ser Ser Ser Thr Val Lys His Ser Thr Ser Ser Ile Gly Ser
            995                 1000                1005

Met Leu Ala Gln Ala Asp Lys Leu Pro Met Thr Asp Lys Arg Val
    1010                1015                1020

Ala Ser Leu Leu Lys Lys Ala Lys Ala Gln Leu Cys Lys Ile Glu
    1025                1030                1035

Lys Ser Lys Ser Leu Lys Gln Thr Asp Gln Pro Lys Ala Gln Gly
    1040                1045                1050

Gln Glu Ser Asp Ser Ser Glu Thr Ser Val Arg Gly Pro Arg Ile
    1055                1060                1065

Lys His Val Cys Arg Arg Ala Ala Val Ala Leu Gly Arg Lys Arg
    1070                1075                1080

Ala Val Phe Pro Asp Asp Met Pro Thr Leu Ser Ala Leu Pro Trp
    1085                1090                1095

Glu Glu Arg Glu Lys Ile Leu Ser Ser Met Gly Asn Asp Asp Lys
    1100                1105                1110

Ser Ser Ile Ala Gly Ser Glu Asp Ala Glu Pro Leu Ala Pro Pro
    1115                1120                1125

Ile Lys Pro Ile Lys Pro Val Thr Arg Asn Lys Ala Pro Gln Glu
    1130                1135                1140

Pro Pro Val Lys Lys Gly Arg Arg Ser Arg Arg Cys Gly Gln Cys
    1145                1150                1155

Pro Gly Cys Gln Val Pro Glu Asp Cys Gly Val Cys Thr Asn Cys
    1160                1165                1170

Leu Asp Lys Pro Lys Phe Gly Gly Arg Asn Ile Lys Lys Gln Cys
    1175                1180                1185

Cys Lys Met Arg Lys Cys Gln Asn Leu Gln Trp Met Pro Ser Lys
    1190                1195                1200

Ala Tyr Leu Gln Lys Gln Ala Lys Ala Val Lys Lys Lys Glu Lys
    1205                1210                1215

Lys Ser Lys Thr Ser Glu Lys Lys Asp Ser Lys Glu Ser Ser Val
    1220                1225                1230

Val Lys Asn Val Val Asp Ser Ser Gln Lys Pro Thr Pro Ser Ala
    1235                1240                1245

Arg Glu Asp Pro Ala Pro Lys Lys Ser Ser Ser Glu Pro Pro Pro
    1250                1255                1260

Arg Lys Pro Val Glu Glu Lys Ser Glu Glu Gly Asn Val Ser Ala
    1265                1270                1275

Pro Gly Pro Glu Ser Lys Gln Ala Thr Thr Pro Ala Ser Arg Lys
    1280                1285                1290
```

-continued

```
Ser Ser Lys Gln Val Ser Gln Pro Ala Leu Val Ile Pro Pro Gln
1295                1300                1305

Pro Pro Thr Thr Gly Pro Pro Arg Lys Glu Val Pro Lys Thr Thr
1310                1315                1320

Pro Ser Glu Pro Lys Lys Lys Gln Pro Pro Pro Glu Ser Gly
1325                1330                1335

Pro Glu Gln Ser Lys Gln Lys Lys Val Ala Pro Arg Pro Ser Ile
1340                1345                1350

Pro Val Lys Gln Lys Pro Lys Glu Lys Glu Lys Pro Pro Pro Val
1355                1360                1365

Asn Lys Gln Glu Asn Ala Gly Thr Leu Asn Ile Leu Ser Thr Leu
1370                1375                1380

Ser Asn Gly Asn Ser Ser Lys Gln Lys Ile Pro Ala Asp Gly Val
1385                1390                1395

His Arg Ile Arg Val Asp Phe Lys Phe Val Tyr Cys Gln Val Cys
1400                1405                1410

Cys Glu Pro Phe His Lys Phe Cys Leu Glu Glu Asn Glu Arg Pro
1415                1420                1425

Leu Glu Asp Gln Leu Glu Asn Trp Cys Cys Arg Arg Cys Lys Phe
1430                1435                1440

Cys His Val Cys Gly Arg Gln His Gln Ala Thr Lys Gln Leu Leu
1445                1450                1455

Glu Cys Asn Lys Cys Arg Asn Ser Tyr His Pro Glu Cys Leu Gly
1460                1465                1470

Pro Asn Tyr Pro Thr Lys Pro Thr Lys Lys Lys Val Trp Ile
1475                1480                1485

Cys Thr Lys Cys Val Arg Cys Lys Ser Cys Gly Ser Thr Thr Pro
1490                1495                1500

Gly Lys Gly Trp Asp Ala Gln Trp Ser His Asp Phe Ser Leu Cys
1505                1510                1515

His Asp Cys Ala Lys Leu Phe Ala Lys Gly Asn Phe Cys Pro Leu
1520                1525                1530

Cys Asp Lys Cys Tyr Asp Asp Asp Tyr Glu Ser Lys Met Met
1535                1540                1545

Gln Cys Gly Lys Cys Asp Arg Trp Val His Ser Lys Cys Glu Asn
1550                1555                1560

Leu Ser Asp Glu Met Tyr Glu Ile Leu Ser Asn Leu Pro Glu Ser
1565                1570                1575

Val Ala Tyr Thr Cys Val Asn Cys Thr Glu Arg His Pro Ala Glu
1580                1585                1590

Trp Arg Leu Ala Leu Glu Lys Glu Leu Gln Ile Ser Leu Lys Gln
1595                1600                1605

Val Leu Thr Ala Leu Leu Asn Ser Arg Thr Thr Ser His Leu Leu
1610                1615                1620

Arg Tyr Arg Gln Ala Ala Lys Pro Pro Asp Leu Asn Pro Glu Thr
1625                1630                1635

Glu Glu Ser Ile Pro Ser Arg Ser Ser Pro Glu Gly Pro Asp Pro
1640                1645                1650

Pro Val Leu Thr Glu Val Ser Lys Gln Asp Asp Gln Gln Pro Leu
1655                1660                1665

Asp Leu Glu Gly Val Lys Arg Lys Met Asp Gln Gly Asn Tyr Thr
1670                1675                1680

Ser Val Leu Glu Phe Ser Asp Asp Ile Val Lys Ile Ile Gln Ala
```

```
                1685                1690                1695

Ala Ile Asn Ser Asp Gly Gly Gln Pro Glu Ile Lys Lys Ala Asn
    1700                1705                1710

Ser Met Val Lys Ser Phe Phe Ile Arg Gln Met Glu Arg Val Phe
    1715                1720                1725

Pro Trp Phe Ser Val Lys Lys Ser Arg Phe Trp Glu Pro Asn Lys
    1730                1735                1740

Val Ser Ser Asn Ser Gly Met Leu Pro Asn Ala Val Leu Pro Pro
    1745                1750                1755

Ser Leu Asp His Asn Tyr Ala Gln Trp Gln Glu Arg Glu Glu Asn
    1760                1765                1770

Ser His Thr Glu Gln Pro Pro Leu Met Lys Lys Ile Ile Pro Ala
    1775                1780                1785

Pro Lys Pro Lys Gly Pro Gly Glu Pro Asp Ser Pro Thr Pro Leu
    1790                1795                1800

His Pro Pro Thr Pro Pro Ile Leu Ser Thr Asp Arg Ser Arg Glu
    1805                1810                1815

Asp Ser Pro Glu Leu Asn Pro Pro Pro Gly Ile Glu Asp Asn Arg
    1820                1825                1830

Gln Cys Ala Leu Cys Leu Thr Tyr Gly Asp Asp Ser Ala Asn Asp
    1835                1840                1845

Ala Gly Arg Leu Leu Tyr Ile Gly Gln Asn Glu Trp Thr His Val
    1850                1855                1860

Asn Cys Ala Leu Trp Ser Ala Glu Val Phe Glu Asp Asp Asp Gly
    1865                1870                1875

Ser Leu Lys Asn Val His Met Ala Val Ile Arg Gly Lys Gln Leu
    1880                1885                1890

Arg Cys Glu Phe Cys Gln Lys Pro Gly Ala Thr Val Gly Cys Cys
    1895                1900                1905

Leu Thr Ser Cys Thr Ser Asn Tyr His Phe Met Cys Ser Arg Ala
    1910                1915                1920

Lys Asn Cys Val Phe Leu Asp Asp Lys Lys Val Tyr Cys Gln Arg
    1925                1930                1935

His Arg Asp Leu Ile Lys Gly Glu Val Val Pro Glu Asn Gly Phe
    1940                1945                1950

Glu Val Phe Arg Arg Val Phe Val Asp Phe Glu Gly Ile Ser Leu
    1955                1960                1965

Arg Arg Lys Phe Leu Asn Gly Leu Glu Pro Glu Asn Ile His Met
    1970                1975                1980

Met Ile Gly Ser Met Thr Ile Asp Cys Leu Gly Ile Leu Asn Asp
    1985                1990                1995

Leu Ser Asp Cys Glu Asp Lys Leu Phe Pro Ile Gly Tyr Gln Cys
    2000                2005                2010

Ser Arg Val Tyr Trp Ser Thr Thr Asp Ala Arg Lys Arg Cys Val
    2015                2020                2025

Tyr Thr Cys Lys Ile Val Glu Cys Arg Pro Pro Val Val Glu Pro
    2030                2035                2040

Asp Ile Asn Ser Thr Val Glu His Asp Glu Asn Arg Thr Ile Ala
    2045                2050                2055

His Ser Pro Thr Ser Phe Thr Glu Ser Ser Ser Lys Glu Ser Gln
    2060                2065                2070

Asn Thr Ala Glu Ile Ile Ser Pro Pro Ser Pro Asp Arg Pro Pro
    2075                2080                2085
```

```
His Ser Gln Thr Ser Gly Ser Cys Tyr Tyr His Val Ile Ser Lys
    2090            2095                2100

Val Pro Arg Ile Arg Thr Pro Ser Tyr Ser Pro Thr Gln Arg Ser
    2105            2110                2115

Pro Gly Cys Arg Pro Leu Pro Ser Ala Gly Ser Pro Thr Pro Thr
    2120            2125                2130

Thr His Glu Ile Val Thr Val Gly Asp Pro Leu Leu Ser Ser Gly
    2135            2140                2145

Leu Arg Ser Ile Gly Ser Arg Arg His Ser Thr Ser Ser Leu Ser
    2150            2155                2160

Pro Gln Arg Ser Lys Leu Arg Ile Met Ser Pro Met Arg Thr Gly
    2165            2170                2175

Asn Thr Tyr Ser Arg Asn Asn Val Ser Ser Val Ser Thr Thr Gly
    2180            2185                2190

Thr Ala Thr Asp Leu Glu Ser Ser Ala Lys Val Val Asp His Val
    2195            2200                2205

Leu Gly Pro Leu Asn Ser Ser Thr Ser Leu Gly Gln Asn Thr Ser
    2210            2215                2220

Thr Ser Ser Asn Leu Gln Arg Thr Val Val Thr Val Gly Asn Lys
    2225            2230                2235

Asn Ser His Leu Asp Gly Ser Ser Ser Ser Glu Met Lys Gln Ser
    2240            2245                2250

Ser Ala Ser Asp Leu Val Ser Lys Ser Ser Leu Lys Gly Glu
    2255            2260                2265

Lys Thr Lys Val Leu Ser Ser Lys Ser Ser Glu Gly Ser Ala His
    2270            2275                2280

Asn Val Ala Tyr Pro Gly Ile Pro Lys Leu Ala Pro Gln Val His
    2285            2290                2295

Asn Thr Thr Ser Arg Glu Leu Asn Val Ser Lys Ile Gly Ser Phe
    2300            2305                2310

Ala Glu Pro Ser Ser Val Ser Phe Ser Ser Lys Glu Ala Leu Ser
    2315            2320                2325

Phe Pro His Leu His Leu Arg Gly Gln Arg Asn Asp Arg Asp Gln
    2330            2335                2340

His Thr Asp Ser Thr Gln Ser Ala Asn Ser Ser Pro Asp Glu Asp
    2345            2350                2355

Thr Glu Val Lys Thr Leu Lys Leu Ser Gly Met Ser Asn Arg Ser
    2360            2365                2370

Ser Ile Ile Asn Glu His Met Gly Ser Ser Arg Asp Arg Arg
    2375            2380                2385

Gln Lys Gly Lys Lys Ser Cys Lys Glu Thr Phe Lys Glu Lys His
    2390            2395                2400

Ser Ser Lys Ser Phe Leu Glu Pro Gly Gln Val Thr Thr Gly Glu
    2405            2410                2415

Glu Gly Asn Leu Lys Pro Glu Phe Met Asp Glu Val Leu Thr Pro
    2420            2425                2430

Glu Tyr Met Gly Gln Arg Pro Cys Asn Asn Val Ser Ser Asp Lys
    2435            2440                2445

Ile Gly Asp Lys Gly Leu Ser Met Pro Gly Val Pro Lys Ala Pro
    2450            2455                2460

Pro Met Gln Val Glu Gly Ser Ala Lys Glu Leu Gln Ala Pro Arg
    2465            2470                2475
```

```
Lys Arg Thr Val Lys Val Thr Leu Thr Pro Leu Lys Met Glu Asn
2480            2485                2490

Glu Ser Gln Ser Lys Asn Ala Leu Lys Glu Ser Ser Pro Ala Ser
2495            2500                2505

Pro Leu Gln Ile Glu Ser Thr Ser Pro Thr Glu Pro Ile Ser Ala
2510            2515                2520

Ser Glu Asn Pro Gly Asp Gly Pro Val Ala Gln Pro Ser Pro Asn
2525            2530                2535

Asn Thr Ser Cys Gln Asp Ser Gln Ser Asn Asn Tyr Gln Asn Leu
2540            2545                2550

Pro Val Gln Asp Arg Asn Leu Met Leu Pro Asp Gly Pro Lys Pro
2555            2560                2565

Gln Glu Asp Gly Ser Phe Lys Arg Arg Tyr Pro Arg Arg Ser Ala
2570            2575                2580

Arg Ala Arg Ser Asn Met Phe Phe Gly Leu Thr Pro Leu Tyr Gly
2585            2590                2595

Val Arg Ser Tyr Gly Glu Glu Asp Ile Pro Phe Tyr Ser Ser Ser
2600            2605                2610

Thr Gly Lys Lys Arg Gly Lys Arg Ser Ala Glu Gly Gln Val Asp
2615            2620                2625

Gly Ala Asp Asp Leu Ser Thr Ser Asp Glu Asp Asp Leu Tyr Tyr
2630            2635                2640

Tyr Asn Phe Thr Arg Thr Val Ile Ser Ser Gly Gly Glu Glu Arg
2645            2650                2655

Leu Ala Ser His Asn Leu Phe Arg Glu Glu Glu Gln Cys Asp Leu
2660            2665                2670

Pro Lys Ile Ser Gln Leu Asp Gly Val Asp Asp Gly Thr Glu Ser
2675            2680                2685

Asp Thr Ser Val Thr Ala Thr Thr Arg Lys Ser Ser Gln Ile Pro
2690            2695                2700

Lys Arg Asn Gly Lys Glu Asn Gly Thr Glu Asn Leu Lys Ile Asp
2705            2710                2715

Arg Pro Glu Asp Ala Gly Glu Lys Glu His Val Thr Lys Ser Ser
2720            2725                2730

Val Gly His Lys Asn Glu Pro Lys Met Asp Asn Cys His Ser Val
2735            2740                2745

Ser Arg Val Lys Thr Gln Gly Gln Asp Ser Leu Glu Ala Gln Leu
2750            2755                2760

Ser Ser Leu Glu Ser Ser Arg Arg Val His Thr Ser Thr Pro Ser
2765            2770                2775

Asp Lys Asn Leu Leu Asp Thr Tyr Asn Thr Glu Leu Leu Lys Ser
2780            2785                2790

Asp Ser Asp Asn Asn Asn Ser Asp Asp Cys Gly Asn Ile Leu Pro
2795            2800                2805

Ser Asp Ile Met Asp Phe Val Leu Lys Asn Thr Pro Ser Met Gln
2810            2815                2820

Ala Leu Gly Glu Ser Pro Glu Ser Ser Ser Ser Glu Leu Leu Asn
2825            2830                2835

Leu Gly Glu Gly Leu Gly Leu Asp Ser Asn Arg Glu Lys Asp Met
2840            2845                2850

Gly Leu Phe Glu Val Phe Ser Gln Gln Leu Pro Thr Thr Glu Pro
2855            2860                2865

Val Asp Ser Ser Val Ser Ser Ser Ile Ser Ala Glu Glu Gln Phe
```

-continued

```
                2870                2875                2880
Glu Leu Pro Leu Glu Leu Pro Ser Asp Leu Ser Val Leu Thr Thr
        2885                2890                2895
Arg Ser Pro Thr Val Pro Ser Gln Asn Pro Ser Arg Leu Ala Val
        2900                2905                2910
Ile Ser Asp Ser Gly Glu Lys Arg Val Thr Ile Thr Glu Lys Ser
        2915                2920                2925
Val Ala Ser Ser Glu Ser Asp Pro Ala Leu Leu Ser Pro Gly Val
        2930                2935                2940
Asp Pro Thr Pro Glu Gly His Met Thr Pro Asp His Phe Ile Gln
        2945                2950                2955
Gly His Met Asp Ala Asp His Ile Ser Ser Pro Cys Gly Ser
        2960                2965                2970
Val Glu Gln Gly His Gly Asn Asn Gln Asp Leu Thr Arg Asn Ser
        2975                2980                2985
Ser Thr Pro Gly Leu Gln Val Pro Val Ser Pro Thr Val Pro Ile
        2990                2995                3000
Gln Asn Gln Lys Tyr Val Pro Asn Ser Thr Asp Ser Pro Gly Pro
        3005                3010                3015
Ser Gln Ile Ser Asn Ala Ala Val Gln Thr Thr Pro Pro His Leu
        3020                3025                3030
Lys Pro Ala Thr Glu Lys Leu Ile Val Val Asn Gln Asn Met Gln
        3035                3040                3045
Pro Leu Tyr Val Leu Gln Thr Leu Pro Asn Gly Val Thr Gln Lys
        3050                3055                3060
Ile Gln Leu Thr Ser Ser Val Ser Ser Thr Pro Ser Val Met Glu
        3065                3070                3075
Thr Asn Thr Ser Val Leu Gly Pro Met Gly Gly Gly Leu Thr Leu
        3080                3085                3090
Thr Thr Gly Leu Asn Pro Ser Leu Pro Thr Ser Gln Ser Leu Phe
        3095                3100                3105
Pro Ser Ala Ser Lys Gly Leu Leu Pro Met Ser His His Gln His
        3110                3115                3120
Leu His Ser Phe Pro Ala Ala Thr Gln Ser Ser Phe Pro Pro Asn
        3125                3130                3135
Ile Ser Asn Pro Pro Ser Gly Leu Leu Ile Gly Val Gln Pro Pro
        3140                3145                3150
Pro Asp Pro Gln Leu Leu Val Ser Glu Ser Ser Gln Arg Thr Asp
        3155                3160                3165
Leu Ser Thr Thr Val Ala Thr Pro Ser Ser Gly Leu Lys Lys Arg
        3170                3175                3180
Pro Ile Ser Arg Leu Gln Thr Arg Lys Asn Lys Lys Leu Ala Pro
        3185                3190                3195
Ser Ser Thr Pro Ser Asn Ile Ala Pro Ser Asp Val Val Ser Asn
        3200                3205                3210
Met Thr Leu Ile Asn Phe Thr Pro Ser Gln Leu Pro Asn His Pro
        3215                3220                3225
Ser Leu Leu Asp Leu Gly Ser Leu Asn Thr Ser Ser His Arg Thr
        3230                3235                3240
Val Pro Asn Ile Ile Lys Arg Ser Lys Ser Ser Ile Met Tyr Phe
        3245                3250                3255
Glu Pro Ala Pro Leu Leu Pro Gln Ser Val Gly Gly Thr Ala Ala
        3260                3265                3270
```

-continued

```
Thr Ala Ala Gly Thr Ser Thr Ile Ser Gln Asp Thr Ser His Leu
    3275                3280                3285

Thr Ser Gly Ser Val Ser Gly Leu Ala Ser Ser Ser Val Leu
    3290                3295                3300

Asn Val Val Ser Met Gln Thr Thr Thr Pro Thr Ser Ser Ala
    3305                3310                3315

Ser Val Pro Gly His Val Thr Leu Thr Asn Pro Arg Leu Leu Gly
    3320                3325                3330

Thr Pro Asp Ile Gly Ser Ile Ser Asn Leu Leu Ile Lys Ala Ser
    3335                3340                3345

Gln Gln Ser Leu Gly Ile Gln Asp Gln Pro Val Ala Leu Pro Pro
    3350                3355                3360

Ser Ser Gly Met Phe Pro Gln Leu Gly Thr Ser Gln Thr Pro Ser
    3365                3370                3375

Thr Ala Ala Ile Thr Ala Ala Ser Ser Ile Cys Val Leu Pro Ser
    3380                3385                3390

Thr Gln Thr Thr Gly Ile Thr Ala Ala Ser Pro Ser Gly Glu Ala
    3395                3400                3405

Asp Glu His Tyr Gln Leu Gln His Val Asn Gln Leu Leu Ala Ser
    3410                3415                3420

Lys Thr Gly Ile His Ser Ser Gln Arg Asp Leu Asp Ser Ala Ser
    3425                3430                3435

Gly Pro Gln Val Ser Asn Phe Thr Gln Thr Val Asp Ala Pro Asn
    3440                3445                3450

Ser Met Gly Leu Glu Gln Asn Lys Ala Leu Ser Ser Ala Val Gln
    3455                3460                3465

Ala Ser Pro Thr Ser Pro Gly Gly Ser Pro Ser Ser Pro Ser Ser
    3470                3475                3480

Gly Gln Arg Ser Ala Ser Pro Ser Val Pro Gly Pro Thr Lys Pro
    3485                3490                3495

Lys Pro Lys Thr Lys Arg Phe Gln Leu Pro Leu Asp Lys Gly Asn
    3500                3505                3510

Gly Lys Lys His Lys Val Ser His Leu Arg Thr Ser Ser Ser Glu
    3515                3520                3525

Ala His Ile Pro Asp Gln Glu Thr Thr Ser Leu Thr Ser Gly Thr
    3530                3535                3540

Gly Thr Pro Gly Ala Glu Ala Glu Gln Gln Asp Thr Ala Ser Val
    3545                3550                3555

Glu Gln Ser Ser Gln Lys Glu Cys Gly Gln Pro Ala Gly Gln Val
    3560                3565                3570

Ala Val Leu Pro Glu Val Gln Val Thr Gln Asn Pro Ala Asn Glu
    3575                3580                3585

Gln Glu Ser Ala Glu Pro Lys Thr Val Glu Glu Glu Ser Asn
    3590                3595                3600

Phe Ser Ser Pro Leu Met Leu Trp Leu Gln Gln Glu Gln Lys Arg
    3605                3610                3615

Lys Glu Ser Ile Thr Glu Lys Lys Pro Lys Lys Gly Leu Val Phe
    3620                3625                3630

Glu Ile Ser Ser Asp Asp Gly Phe Gln Ile Cys Ala Glu Ser Ile
    3635                3640                3645

Glu Asp Ala Trp Lys Ser Leu Thr Asp Lys Val Gln Glu Ala Arg
    3650                3655                3660
```

```
Ser Asn Ala Arg Leu Lys Gln Leu Ser Phe Ala Gly Val Asn Gly
    3665                3670                3675

Leu Arg Met Leu Gly Ile Leu His Asp Ala Val Val Phe Leu Ile
    3680                3685                3690

Glu Gln Leu Ser Gly Ala Lys His Cys Arg Asn Tyr Lys Phe Arg
    3695                3700                3705

Phe His Lys Pro Glu Glu Ala Asn Glu Pro Pro Leu Asn Pro His
    3710                3715                3720

Gly Ser Ala Arg Ala Glu Val His Leu Arg Lys Ser Ala Phe Asp
    3725                3730                3735

Met Phe Asn Phe Leu Ala Ser Lys His Arg Gln Pro Pro Glu Tyr
    3740                3745                3750

Asn Pro Asn Asp Glu Glu Glu Glu Val Gln Leu Lys Ser Ala
    3755                3760                3765

Arg Arg Ala Thr Ser Met Asp Leu Pro Met Pro Met Arg Phe Arg
    3770                3775                3780

His Leu Lys Lys Thr Ser Lys Glu Ala Val Gly Val Tyr Arg Ser
    3785                3790                3795

Pro Ile His Gly Arg Gly Leu Phe Cys Lys Arg Asn Ile Asp Ala
    3800                3805                3810

Gly Glu Met Val Ile Glu Tyr Ala Gly Asn Val Ile Arg Ser Ile
    3815                3820                3825

Gln Thr Asp Lys Arg Glu Lys Tyr Tyr Asp Ser Lys Gly Ile Gly
    3830                3835                3840

Cys Tyr Met Phe Arg Ile Asp Asp Ser Glu Val Val Asp Ala Thr
    3845                3850                3855

Met His Gly Asn Ala Ala Arg Phe Ile Asn His Ser Cys Glu Pro
    3860                3865                3870

Asn Cys Tyr Ser Arg Val Ile Asn Ile Asp Gly Gln Lys His Ile
    3875                3880                3885

Val Ile Phe Ala Met Arg Lys Ile Tyr Arg Gly Glu Glu Leu Thr
    3890                3895                3900

Tyr Asp Tyr Lys Phe Pro Ile Glu Asp Ala Ser Asn Lys Leu Pro
    3905                3910                3915

Cys Asn Cys Gly Ala Lys Lys Cys Arg Lys Phe Leu Asn
    3920                3925                3930

<210> SEQ ID NO 3
<211> LENGTH: 3972
<212> TYPE: PRT
<213> ORGANISM: Homo sapiens

<400> SEQUENCE: 3

Met Ala His Ser Cys Arg Trp Arg Phe Pro Ala Arg Pro Gly Thr Thr
1               5                   10                  15

Gly Gly Gly Gly Gly Gly Gly Arg Arg Gly Leu Gly Gly Ala Pro Arg
                20                  25                  30

Gln Arg Val Pro Ala Leu Leu Leu Pro Pro Gly Pro Pro Val Gly Gly
            35                  40                  45

Gly Gly Pro Gly Ala Pro Pro Ser Pro Ala Val Ala Ala Ala Ala
        50                  55                  60

Ala Ala Ala Gly Ser Ser Gly Ala Gly Val Pro Gly Gly Ala Ala Ala
65                  70                  75                  80

Ala Ser Ala Ala Ser Ser Ser Ser Ala Ser Ser Ser Ser Ser Ser
                85                  90                  95
```

-continued

```
Ser Ser Ala Ser Ser Gly Pro Ala Leu Leu Arg Val Gly Pro Gly Phe
            100                 105                 110

Asp Ala Ala Leu Gln Val Ser Ala Ala Ile Gly Thr Asn Leu Arg Arg
        115                 120                 125

Phe Arg Ala Val Phe Gly Glu Ser Gly Gly Gly Gly Ser Gly Glu
130                 135                 140

Asp Glu Gln Phe Leu Gly Phe Gly Ser Asp Glu Glu Val Arg Val Arg
145                 150                 155                 160

Ser Pro Thr Arg Ser Pro Ser Val Lys Thr Ser Pro Arg Lys Pro Arg
                165                 170                 175

Gly Arg Pro Arg Ser Gly Ser Asp Arg Asn Ser Ala Ile Leu Ser Asp
                180                 185                 190

Pro Ser Val Phe Ser Pro Leu Asn Lys Ser Glu Thr Lys Ser Gly Asp
                195                 200                 205

Lys Ile Lys Lys Lys Asp Ser Lys Ser Ile Glu Lys Lys Arg Gly Arg
    210                 215                 220

Pro Pro Thr Phe Pro Gly Val Lys Ile Lys Ile Thr His Gly Lys Asp
225                 230                 235                 240

Ile Ser Glu Leu Pro Lys Gly Asn Lys Glu Asp Ser Leu Lys Lys Ile
                245                 250                 255

Lys Arg Thr Pro Ser Ala Thr Phe Gln Gln Ala Thr Lys Ile Lys Lys
                260                 265                 270

Leu Arg Ala Gly Lys Leu Ser Pro Leu Lys Ser Lys Phe Lys Thr Gly
            275                 280                 285

Lys Leu Gln Ile Gly Arg Lys Gly Val Gln Ile Val Arg Arg Arg Gly
        290                 295                 300

Arg Pro Pro Ser Thr Glu Arg Ile Lys Thr Pro Ser Gly Leu Leu Ile
305                 310                 315                 320

Asn Ser Glu Leu Glu Lys Pro Gln Lys Val Arg Lys Asp Lys Glu Gly
                325                 330                 335

Thr Pro Pro Leu Thr Lys Glu Asp Lys Thr Val Val Arg Gln Ser Pro
                340                 345                 350

Arg Arg Ile Lys Pro Val Arg Ile Ile Pro Ser Ser Lys Arg Thr Asp
            355                 360                 365

Ala Thr Ile Ala Lys Gln Leu Leu Gln Arg Ala Lys Lys Gly Ala Gln
        370                 375                 380

Lys Lys Ile Glu Lys Glu Ala Ala Gln Leu Gln Gly Arg Lys Val Lys
385                 390                 395                 400

Thr Gln Val Lys Asn Ile Arg Gln Phe Ile Met Pro Val Val Ser Ala
                405                 410                 415

Ile Ser Ser Arg Ile Ile Lys Thr Pro Arg Arg Phe Ile Glu Asp Glu
                420                 425                 430

Asp Tyr Asp Pro Pro Ile Lys Ile Ala Arg Leu Glu Ser Thr Pro Asn
            435                 440                 445

Ser Arg Phe Ser Ala Pro Ser Cys Gly Ser Ser Glu Lys Ser Ser Ala
        450                 455                 460

Ala Ser Gln His Ser Ser Gln Met Ser Ser Asp Ser Ser Arg Ser Ser
465                 470                 475                 480

Ser Pro Ser Val Asp Thr Ser Thr Asp Ser Gln Ala Ser Glu Glu Ile
                485                 490                 495

Gln Val Leu Pro Glu Glu Arg Ser Asp Thr Pro Glu Val His Pro Pro
                500                 505                 510
```

```
Leu Pro Ile Ser Gln Ser Pro Glu Asn Glu Ser Asn Asp Arg Arg Ser
            515                 520                 525

Arg Arg Tyr Ser Val Ser Glu Arg Ser Phe Gly Ser Arg Thr Thr Lys
    530                 535                 540

Lys Leu Ser Thr Leu Gln Ser Ala Pro Gln Gln Gln Thr Ser Ser Ser
545                 550                 555                 560

Pro Pro Pro Pro Leu Leu Thr Pro Pro Pro Leu Gln Pro Ala Ser
                565                 570                 575

Ser Ile Ser Asp His Thr Pro Trp Leu Met Pro Pro Thr Ile Pro Leu
            580                 585                 590

Ala Ser Pro Phe Leu Pro Ala Ser Thr Ala Pro Met Gln Gly Lys Arg
        595                 600                 605

Lys Ser Ile Leu Arg Glu Pro Thr Phe Arg Trp Thr Ser Leu Lys His
    610                 615                 620

Ser Arg Ser Glu Pro Gln Tyr Phe Ser Ser Ala Lys Tyr Ala Lys Glu
625                 630                 635                 640

Gly Leu Ile Arg Lys Pro Ile Phe Asp Asn Phe Arg Pro Pro Pro Leu
                645                 650                 655

Thr Pro Glu Asp Val Gly Phe Ala Ser Gly Phe Ser Ala Ser Gly Thr
            660                 665                 670

Ala Ala Ser Ala Arg Leu Phe Ser Pro Leu His Ser Gly Thr Arg Phe
        675                 680                 685

Asp Met His Lys Arg Ser Pro Leu Leu Arg Ala Pro Arg Phe Thr Pro
    690                 695                 700

Ser Glu Ala His Ser Arg Ile Phe Glu Ser Val Thr Leu Pro Ser Asn
705                 710                 715                 720

Arg Thr Ser Ala Gly Thr Ser Ser Ser Gly Val Ser Asn Arg Lys Arg
                725                 730                 735

Lys Arg Lys Val Phe Ser Pro Ile Arg Ser Glu Pro Arg Ser Pro Ser
            740                 745                 750

His Ser Met Arg Thr Arg Ser Gly Arg Leu Ser Ser Glu Leu Ser
        755                 760                 765

Pro Leu Thr Pro Pro Ser Ser Val Ser Ser Ser Leu Ser Ile Ser Val
    770                 775                 780

Ser Pro Leu Ala Thr Ser Ala Leu Asn Pro Thr Phe Thr Phe Pro Ser
785                 790                 795                 800

His Ser Leu Thr Gln Ser Gly Glu Ser Ala Glu Lys Asn Gln Arg Pro
                805                 810                 815

Arg Lys Gln Thr Ser Ala Pro Ala Glu Pro Phe Ser Ser Ser Ser Pro
            820                 825                 830

Thr Pro Leu Phe Pro Trp Phe Thr Pro Gly Ser Gln Thr Glu Arg Gly
        835                 840                 845

Arg Asn Lys Asp Lys Ala Pro Glu Glu Leu Ser Lys Asp Arg Asp Ala
    850                 855                 860

Asp Lys Ser Val Glu Lys Asp Lys Ser Arg Glu Arg Asp Arg Glu Arg
865                 870                 875                 880

Glu Lys Glu Asn Lys Arg Glu Ser Arg Lys Glu Lys Arg Lys Lys Gly
                885                 890                 895

Ser Glu Ile Gln Ser Ser Ser Ala Leu Tyr Pro Val Gly Arg Val Ser
            900                 905                 910

Lys Glu Lys Val Val Gly Glu Asp Val Ala Thr Ser Ser Ser Ala Lys
        915                 920                 925

Lys Ala Thr Gly Arg Lys Lys Ser Ser Ser His Asp Ser Gly Thr Asp
```

```
              930            935            940
Ile Thr Ser Val Thr Leu Gly Asp Thr Thr Ala Val Lys Thr Lys Ile
945                950            955             960

Leu Ile Lys Lys Gly Arg Gly Asn Leu Glu Lys Thr Asn Leu Asp Leu
            965            970             975

Gly Pro Thr Ala Pro Ser Leu Glu Lys Glu Lys Thr Leu Cys Leu Ser
            980            985             990

Thr Pro Ser Ser Ser Thr Val Lys His Ser Thr Ser Ser Ile Gly Ser
            995            1000            1005

Met Leu Ala Gln Ala Asp Lys Leu Pro Met Thr Asp Lys Arg Val
    1010            1015           1020

Ala Ser Leu Leu Lys Lys Ala Lys Ala Gln Leu Cys Lys Ile Glu
    1025            1030           1035

Lys Ser Lys Ser Leu Lys Gln Thr Asp Gln Pro Lys Ala Gln Gly
    1040            1045           1050

Gln Glu Ser Asp Ser Ser Glu Thr Ser Val Arg Gly Pro Arg Ile
    1055            1060           1065

Lys His Val Cys Arg Arg Ala Ala Val Ala Leu Gly Arg Lys Arg
    1070            1075           1080

Ala Val Phe Pro Asp Asp Met Pro Thr Leu Ser Ala Leu Pro Trp
    1085            1090           1095

Glu Glu Arg Glu Lys Ile Leu Ser Ser Met Gly Asn Asp Asp Lys
    1100            1105           1110

Ser Ser Ile Ala Gly Ser Glu Asp Ala Glu Pro Leu Ala Pro Pro
    1115            1120           1125

Ile Lys Pro Ile Lys Pro Val Thr Arg Asn Lys Ala Pro Gln Glu
    1130            1135           1140

Pro Pro Val Lys Lys Gly Arg Arg Ser Arg Arg Cys Gly Gln Cys
    1145            1150           1155

Pro Gly Cys Gln Val Pro Glu Asp Cys Gly Val Cys Thr Asn Cys
    1160            1165           1170

Leu Asp Lys Pro Lys Phe Gly Gly Arg Asn Ile Lys Lys Gln Cys
    1175            1180           1185

Cys Lys Met Arg Lys Cys Gln Asn Leu Gln Trp Met Pro Ser Lys
    1190            1195           1200

Ala Tyr Leu Gln Lys Gln Ala Lys Ala Val Lys Lys Lys Glu Lys
    1205            1210           1215

Lys Ser Lys Thr Ser Glu Lys Lys Asp Ser Lys Glu Ser Ser Val
    1220            1225           1230

Val Lys Asn Val Val Asp Ser Ser Gln Lys Pro Thr Pro Ser Ala
    1235            1240           1245

Arg Glu Asp Pro Ala Pro Lys Lys Ser Ser Glu Pro Pro Pro
    1250            1255           1260

Arg Lys Pro Val Glu Glu Lys Ser Glu Glu Gly Asn Val Ser Ala
    1265            1270           1275

Pro Gly Pro Glu Ser Lys Gln Ala Thr Thr Pro Ala Ser Arg Lys
    1280            1285           1290

Ser Ser Lys Gln Val Ser Gln Pro Ala Leu Val Ile Pro Pro Gln
    1295            1300           1305

Pro Pro Thr Thr Gly Pro Pro Arg Lys Glu Val Pro Lys Thr Thr
    1310            1315           1320

Pro Ser Glu Pro Lys Lys Lys Gln Pro Pro Pro Glu Ser Gly
    1325            1330           1335
```

-continued

Pro Glu Gln Ser Lys Gln Lys Lys Val Ala Pro Arg Pro Ser Ile
1340             1345                 1350

Pro Val Lys Gln Lys Pro Lys Glu Lys Glu Lys Pro Pro Pro Val
1355             1360                 1365

Asn Lys Gln Glu Asn Ala Gly Thr Leu Asn Ile Leu Ser Thr Leu
1370             1375                 1380

Ser Asn Gly Asn Ser Ser Lys Gln Lys Ile Pro Ala Asp Gly Val
1385             1390                 1395

His Arg Ile Arg Val Asp Phe Lys Glu Asp Cys Glu Ala Glu Asn
1400             1405                 1410

Val Trp Glu Met Gly Gly Leu Gly Ile Leu Thr Ser Val Pro Ile
1415             1420                 1425

Thr Pro Arg Val Val Cys Phe Leu Cys Ala Ser Ser Gly His Val
1430             1435                 1440

Glu Phe Val Tyr Cys Gln Val Cys Cys Glu Pro Phe His Lys Phe
1445             1450                 1455

Cys Leu Glu Glu Asn Glu Arg Pro Leu Glu Asp Gln Leu Glu Asn
1460             1465                 1470

Trp Cys Cys Arg Arg Cys Lys Phe Cys His Val Cys Gly Arg Gln
1475             1480                 1485

His Gln Ala Thr Lys Gln Leu Leu Glu Cys Asn Lys Cys Arg Asn
1490             1495                 1500

Ser Tyr His Pro Glu Cys Leu Gly Pro Asn Tyr Pro Thr Lys Pro
1505             1510                 1515

Thr Lys Lys Lys Lys Val Trp Ile Cys Thr Lys Cys Val Arg Cys
1520             1525                 1530

Lys Ser Cys Gly Ser Thr Thr Pro Gly Lys Gly Trp Asp Ala Gln
1535             1540                 1545

Trp Ser His Asp Phe Ser Leu Cys His Asp Cys Ala Lys Leu Phe
1550             1555                 1560

Ala Lys Gly Asn Phe Cys Pro Leu Cys Asp Lys Cys Tyr Asp Asp
1565             1570                 1575

Asp Asp Tyr Glu Ser Lys Met Met Gln Cys Gly Lys Cys Asp Arg
1580             1585                 1590

Trp Val His Ser Lys Cys Glu Asn Leu Ser Gly Thr Glu Asp Glu
1595             1600                 1605

Met Tyr Glu Ile Leu Ser Asn Leu Pro Glu Ser Val Ala Tyr Thr
1610             1615                 1620

Cys Val Asn Cys Thr Glu Arg His Pro Ala Glu Trp Arg Leu Ala
1625             1630                 1635

Leu Glu Lys Glu Leu Gln Ile Ser Leu Lys Gln Val Leu Thr Ala
1640             1645                 1650

Leu Leu Asn Ser Arg Thr Thr Ser His Leu Leu Arg Tyr Arg Gln
1655             1660                 1665

Ala Ala Lys Pro Pro Asp Leu Asn Pro Glu Thr Glu Glu Ser Ile
1670             1675                 1680

Pro Ser Arg Ser Ser Pro Glu Gly Pro Asp Pro Val Leu Thr
1685             1690                 1695

Glu Val Ser Lys Gln Asp Asp Gln Gln Pro Leu Asp Leu Glu Gly
1700             1705                 1710

Val Lys Arg Lys Met Asp Gln Gly Asn Tyr Thr Ser Val Leu Glu
1715             1720                 1725

-continued

Phe Ser Asp Asp Ile Val Lys Ile Ile Gln Ala Ala Ile Asn Ser
1730                1735                1740

Asp Gly Gly Gln Pro Glu Ile Lys Lys Ala Asn Ser Met Val Lys
1745                1750                1755

Ser Phe Phe Ile Arg Gln Met Glu Arg Val Phe Pro Trp Phe Ser
1760                1765                1770

Val Lys Lys Ser Arg Phe Trp Glu Pro Asn Lys Val Ser Ser Asn
1775                1780                1785

Ser Gly Met Leu Pro Asn Ala Val Leu Pro Pro Ser Leu Asp His
1790                1795                1800

Asn Tyr Ala Gln Trp Gln Glu Arg Glu Glu Asn Ser His Thr Glu
1805                1810                1815

Gln Pro Pro Leu Met Lys Lys Ile Ile Pro Ala Pro Lys Pro Lys
1820                1825                1830

Gly Pro Gly Glu Pro Asp Ser Pro Thr Pro Leu His Pro Pro Thr
1835                1840                1845

Pro Pro Ile Leu Ser Thr Asp Arg Ser Arg Glu Asp Ser Pro Glu
1850                1855                1860

Leu Asn Pro Pro Pro Gly Ile Glu Asp Asn Arg Gln Cys Ala Leu
1865                1870                1875

Cys Leu Thr Tyr Gly Asp Ser Ala Asn Asp Ala Gly Arg Leu
1880                1885                1890

Leu Tyr Ile Gly Gln Asn Glu Trp Thr His Val Asn Cys Ala Leu
1895                1900                1905

Trp Ser Ala Glu Val Phe Glu Asp Asp Asp Gly Ser Leu Lys Asn
1910                1915                1920

Val His Met Ala Val Ile Arg Gly Lys Gln Leu Arg Cys Glu Phe
1925                1930                1935

Cys Gln Lys Pro Gly Ala Thr Val Gly Cys Cys Leu Thr Ser Cys
1940                1945                1950

Thr Ser Asn Tyr His Phe Met Cys Ser Arg Ala Lys Asn Cys Val
1955                1960                1965

Phe Leu Asp Asp Lys Lys Val Tyr Cys Gln Arg His Arg Asp Leu
1970                1975                1980

Ile Lys Gly Glu Val Val Pro Glu Asn Gly Phe Glu Val Phe Arg
1985                1990                1995

Arg Val Phe Val Asp Phe Glu Gly Ile Ser Leu Arg Arg Lys Phe
2000                2005                2010

Leu Asn Gly Leu Glu Pro Glu Asn Ile His Met Met Ile Gly Ser
2015                2020                2025

Met Thr Ile Asp Cys Leu Gly Ile Leu Asn Asp Leu Ser Asp Cys
2030                2035                2040

Glu Asp Lys Leu Phe Pro Ile Gly Tyr Gln Cys Ser Arg Val Tyr
2045                2050                2055

Trp Ser Thr Thr Asp Ala Arg Lys Arg Cys Val Tyr Thr Cys Lys
2060                2065                2070

Ile Val Glu Cys Arg Pro Pro Val Val Glu Pro Asp Ile Asn Ser
2075                2080                2085

Thr Val Glu His Asp Glu Asn Arg Thr Ile Ala His Ser Pro Thr
2090                2095                2100

Ser Phe Thr Glu Ser Ser Ser Lys Glu Ser Gln Asn Thr Ala Glu
2105                2110                2115

Ile Ile Ser Pro Pro Ser Pro Asp Arg Pro Pro His Ser Gln Thr

```
                    2120                2125                2130

Ser Gly Ser Cys Tyr Tyr His Val Ile Ser Lys Val Pro Arg Ile
    2135                2140                2145

Arg Thr Pro Ser Tyr Ser Pro Thr Gln Arg Ser Pro Gly Cys Arg
    2150                2155                2160

Pro Leu Pro Ser Ala Gly Ser Pro Thr Pro Thr Thr His Glu Ile
    2165                2170                2175

Val Thr Val Gly Asp Pro Leu Leu Ser Ser Gly Leu Arg Ser Ile
    2180                2185                2190

Gly Ser Arg Arg His Ser Thr Ser Ser Leu Ser Pro Gln Arg Ser
    2195                2200                2205

Lys Leu Arg Ile Met Ser Pro Met Arg Thr Gly Asn Thr Tyr Ser
    2210                2215                2220

Arg Asn Asn Val Ser Ser Val Ser Thr Thr Gly Thr Ala Thr Asp
    2225                2230                2235

Leu Glu Ser Ser Ala Lys Val Val Asp His Val Leu Gly Pro Leu
    2240                2245                2250

Asn Ser Ser Thr Ser Leu Gly Gln Asn Thr Ser Thr Ser Ser Asn
    2255                2260                2265

Leu Gln Arg Thr Val Val Thr Val Gly Asn Lys Asn Ser His Leu
    2270                2275                2280

Asp Gly Ser Ser Ser Ser Glu Met Lys Gln Ser Ser Ala Ser Asp
    2285                2290                2295

Leu Val Ser Lys Ser Ser Ser Leu Lys Gly Glu Lys Thr Lys Val
    2300                2305                2310

Leu Ser Ser Lys Ser Ser Glu Gly Ser Ala His Asn Val Ala Tyr
    2315                2320                2325

Pro Gly Ile Pro Lys Leu Ala Pro Gln Val His Asn Thr Thr Ser
    2330                2335                2340

Arg Glu Leu Asn Val Ser Lys Ile Gly Ser Phe Ala Glu Pro Ser
    2345                2350                2355

Ser Val Ser Phe Ser Ser Lys Glu Ala Leu Ser Phe Pro His Leu
    2360                2365                2370

His Leu Arg Gly Gln Arg Asn Asp Arg Asp Gln His Thr Asp Ser
    2375                2380                2385

Thr Gln Ser Ala Asn Ser Ser Pro Asp Glu Asp Thr Glu Val Lys
    2390                2395                2400

Thr Leu Lys Leu Ser Gly Met Ser Asn Arg Ser Ser Ile Ile Asn
    2405                2410                2415

Glu His Met Gly Ser Ser Ser Arg Asp Arg Arg Gln Lys Gly Lys
    2420                2425                2430

Lys Ser Cys Lys Glu Thr Phe Lys Glu Lys His Ser Ser Lys Ser
    2435                2440                2445

Phe Leu Glu Pro Gly Gln Val Thr Thr Gly Glu Glu Gly Asn Leu
    2450                2455                2460

Lys Pro Glu Phe Met Asp Glu Val Leu Thr Pro Glu Tyr Met Gly
    2465                2470                2475

Gln Arg Pro Cys Asn Asn Val Ser Ser Asp Lys Ile Gly Asp Lys
    2480                2485                2490

Gly Leu Ser Met Pro Gly Val Pro Lys Ala Pro Pro Met Gln Val
    2495                2500                2505

Glu Gly Ser Ala Lys Glu Leu Gln Ala Pro Arg Lys Arg Thr Val
    2510                2515                2520
```

```
Lys Val Thr Leu Thr Pro Leu Lys Met Glu Asn Glu Ser Gln Ser
        2525                2530                2535

Lys Asn Ala Leu Lys Glu Ser Ser Pro Ala Ser Pro Leu Gln Ile
        2540                2545                2550

Glu Ser Thr Ser Pro Thr Glu Pro Ile Ser Ala Ser Glu Asn Pro
        2555                2560                2565

Gly Asp Gly Pro Val Ala Gln Pro Ser Pro Asn Asn Thr Ser Cys
        2570                2575                2580

Gln Asp Ser Gln Ser Asn Asn Tyr Gln Asn Leu Pro Val Gln Asp
        2585                2590                2595

Arg Asn Leu Met Leu Pro Asp Gly Pro Lys Pro Gln Glu Asp Gly
        2600                2605                2610

Ser Phe Lys Arg Arg Tyr Pro Arg Arg Ser Ala Arg Ala Arg Ser
        2615                2620                2625

Asn Met Phe Phe Gly Leu Thr Pro Leu Tyr Gly Val Arg Ser Tyr
        2630                2635                2640

Gly Glu Glu Asp Ile Pro Phe Tyr Ser Ser Thr Gly Lys Lys
        2645                2650                2655

Arg Gly Lys Arg Ser Ala Glu Gly Gln Val Asp Gly Ala Asp Asp
        2660                2665                2670

Leu Ser Thr Ser Asp Glu Asp Asp Leu Tyr Tyr Tyr Asn Phe Thr
        2675                2680                2685

Arg Thr Val Ile Ser Ser Gly Gly Glu Glu Arg Leu Ala Ser His
        2690                2695                2700

Asn Leu Phe Arg Glu Glu Glu Gln Cys Asp Leu Pro Lys Ile Ser
        2705                2710                2715

Gln Leu Asp Gly Val Asp Asp Gly Thr Glu Ser Asp Thr Ser Val
        2720                2725                2730

Thr Ala Thr Thr Arg Lys Ser Ser Gln Ile Pro Lys Arg Asn Gly
        2735                2740                2745

Lys Glu Asn Gly Thr Glu Asn Leu Lys Ile Asp Arg Pro Glu Asp
        2750                2755                2760

Ala Gly Glu Lys Glu His Val Thr Lys Ser Ser Val Gly His Lys
        2765                2770                2775

Asn Glu Pro Lys Met Asp Asn Cys His Ser Val Ser Arg Val Lys
        2780                2785                2790

Thr Gln Gly Gln Asp Ser Leu Glu Ala Gln Leu Ser Ser Leu Glu
        2795                2800                2805

Ser Ser Arg Arg Val His Thr Ser Thr Pro Ser Asp Lys Asn Leu
        2810                2815                2820

Leu Asp Thr Tyr Asn Thr Glu Leu Leu Lys Ser Asp Ser Asp Asn
        2825                2830                2835

Asn Asn Ser Asp Asp Cys Gly Asn Ile Leu Pro Ser Asp Ile Met
        2840                2845                2850

Asp Phe Val Leu Lys Asn Thr Pro Ser Met Gln Ala Leu Gly Glu
        2855                2860                2865

Ser Pro Glu Ser Ser Ser Ser Glu Leu Leu Asn Leu Gly Glu Gly
        2870                2875                2880

Leu Gly Leu Asp Ser Asn Arg Glu Lys Asp Met Gly Leu Phe Glu
        2885                2890                2895

Val Phe Ser Gln Gln Leu Pro Thr Thr Glu Pro Val Asp Ser Ser
        2900                2905                2910
```

```
Val Ser Ser Ser Ile Ser Ala Glu Glu Gln Phe Glu Leu Pro Leu
2915                2920                2925

Glu Leu Pro Ser Asp Leu Ser Val Leu Thr Thr Arg Ser Pro Thr
2930                2935                2940

Val Pro Ser Gln Asn Pro Ser Arg Leu Ala Val Ile Ser Asp Ser
2945                2950                2955

Gly Glu Lys Arg Val Thr Ile Thr Glu Lys Ser Val Ala Ser Ser
2960                2965                2970

Glu Ser Asp Pro Ala Leu Leu Ser Pro Gly Val Asp Pro Thr Pro
2975                2980                2985

Glu Gly His Met Thr Pro Asp His Phe Ile Gln Gly His Met Asp
2990                2995                3000

Ala Asp His Ile Ser Ser Pro Pro Cys Gly Ser Val Glu Gln Gly
3005                3010                3015

His Gly Asn Asn Gln Asp Leu Thr Arg Asn Ser Ser Thr Pro Gly
3020                3025                3030

Leu Gln Val Pro Val Ser Pro Thr Val Pro Ile Gln Asn Gln Lys
3035                3040                3045

Tyr Val Pro Asn Ser Thr Asp Ser Pro Gly Pro Ser Gln Ile Ser
3050                3055                3060

Asn Ala Ala Val Gln Thr Thr Pro Pro His Leu Lys Pro Ala Thr
3065                3070                3075

Glu Lys Leu Ile Val Val Asn Gln Asn Met Gln Pro Leu Tyr Val
3080                3085                3090

Leu Gln Thr Leu Pro Asn Gly Val Thr Gln Lys Ile Gln Leu Thr
3095                3100                3105

Ser Ser Val Ser Ser Thr Pro Ser Val Met Glu Thr Asn Thr Ser
3110                3115                3120

Val Leu Gly Pro Met Gly Gly Gly Leu Thr Leu Thr Thr Gly Leu
3125                3130                3135

Asn Pro Ser Leu Pro Thr Ser Gln Ser Leu Phe Pro Ser Ala Ser
3140                3145                3150

Lys Gly Leu Leu Pro Met Ser His His Gln His Leu His Ser Phe
3155                3160                3165

Pro Ala Ala Thr Gln Ser Ser Phe Pro Pro Asn Ile Ser Asn Pro
3170                3175                3180

Pro Ser Gly Leu Leu Ile Gly Val Gln Pro Pro Pro Asp Pro Gln
3185                3190                3195

Leu Leu Val Ser Glu Ser Ser Gln Arg Thr Asp Leu Ser Thr Thr
3200                3205                3210

Val Ala Thr Pro Ser Ser Gly Leu Lys Lys Arg Pro Ile Ser Arg
3215                3220                3225

Leu Gln Thr Arg Lys Asn Lys Lys Leu Ala Pro Ser Ser Thr Pro
3230                3235                3240

Ser Asn Ile Ala Pro Ser Asp Val Val Ser Asn Met Thr Leu Ile
3245                3250                3255

Asn Phe Thr Pro Ser Gln Leu Pro Asn His Pro Ser Leu Leu Asp
3260                3265                3270

Leu Gly Ser Leu Asn Thr Ser Ser His Arg Thr Val Pro Asn Ile
3275                3280                3285

Ile Lys Arg Ser Lys Ser Ser Ile Met Tyr Phe Glu Pro Ala Pro
3290                3295                3300

Leu Leu Pro Gln Ser Val Gly Gly Thr Ala Ala Thr Ala Ala Gly
```

```
            3305                3310                3315
Thr Ser Thr Ile Ser Gln Asp Thr Ser His Leu Thr Ser Gly Ser
    3320                3325                3330

Val Ser Gly Leu Ala Ser Ser Ser Val Leu Asn Val Val Ser
    3335                3340                3345

Met Gln Thr Thr Thr Thr Pro Thr Ser Ser Ala Ser Val Pro Gly
    3350                3355                3360

His Val Thr Leu Thr Asn Pro Arg Leu Leu Gly Thr Pro Asp Ile
    3365                3370                3375

Gly Ser Ile Ser Asn Leu Leu Ile Lys Ala Ser Gln Gln Ser Leu
    3380                3385                3390

Gly Ile Gln Asp Gln Pro Val Ala Leu Pro Pro Ser Ser Gly Met
    3395                3400                3405

Phe Pro Gln Leu Gly Thr Ser Gln Thr Pro Ser Thr Ala Ala Ile
    3410                3415                3420

Thr Ala Ala Ser Ser Ile Cys Val Leu Pro Ser Thr Gln Thr Thr
    3425                3430                3435

Gly Ile Thr Ala Ala Ser Pro Ser Gly Glu Ala Asp Glu His Tyr
    3440                3445                3450

Gln Leu Gln His Val Asn Gln Leu Leu Ala Ser Lys Thr Gly Ile
    3455                3460                3465

His Ser Ser Gln Arg Asp Leu Asp Ser Ala Ser Gly Pro Gln Val
    3470                3475                3480

Ser Asn Phe Thr Gln Thr Val Asp Ala Pro Asn Ser Met Gly Leu
    3485                3490                3495

Glu Gln Asn Lys Ala Leu Ser Ser Ala Val Gln Ala Ser Pro Thr
    3500                3505                3510

Ser Pro Gly Gly Ser Pro Ser Ser Pro Ser Ser Gly Gln Arg Ser
    3515                3520                3525

Ala Ser Pro Ser Val Pro Gly Pro Thr Lys Pro Lys Pro Lys Thr
    3530                3535                3540

Lys Arg Phe Gln Leu Pro Leu Asp Lys Gly Asn Gly Lys Lys His
    3545                3550                3555

Lys Val Ser His Leu Arg Thr Ser Ser Ser Glu Ala His Ile Pro
    3560                3565                3570

Asp Gln Glu Thr Thr Ser Leu Thr Ser Gly Thr Gly Thr Pro Gly
    3575                3580                3585

Ala Glu Ala Glu Gln Gln Asp Thr Ala Ser Val Glu Gln Ser Ser
    3590                3595                3600

Gln Lys Glu Cys Gly Gln Pro Ala Gly Gln Val Ala Val Leu Pro
    3605                3610                3615

Glu Val Gln Val Thr Gln Asn Pro Ala Asn Glu Gln Glu Ser Ala
    3620                3625                3630

Glu Pro Lys Thr Val Glu Glu Glu Ser Asn Phe Ser Ser Pro
    3635                3640                3645

Leu Met Leu Trp Leu Gln Gln Glu Gln Lys Arg Lys Glu Ser Ile
    3650                3655                3660

Thr Glu Lys Lys Pro Lys Lys Gly Leu Val Phe Glu Ile Ser Ser
    3665                3670                3675

Asp Asp Gly Phe Gln Ile Cys Ala Glu Ser Ile Glu Asp Ala Trp
    3680                3685                3690

Lys Ser Leu Thr Asp Lys Val Gln Glu Ala Arg Ser Asn Ala Arg
    3695                3700                3705
```

```
Leu Lys Gln Leu Ser Phe Ala Gly Val Asn Gly Leu Arg Met Leu
    3710            3715                3720

Gly Ile Leu His Asp Ala Val Val Phe Leu Ile Glu Gln Leu Ser
    3725            3730                3735

Gly Ala Lys His Cys Arg Asn Tyr Lys Phe Arg Phe His Lys Pro
    3740            3745                3750

Glu Glu Ala Asn Glu Pro Pro Leu Asn Pro His Gly Ser Ala Arg
    3755            3760                3765

Ala Glu Val His Leu Arg Lys Ser Ala Phe Asp Met Phe Asn Phe
    3770            3775                3780

Leu Ala Ser Lys His Arg Gln Pro Pro Glu Tyr Asn Pro Asn Asp
    3785            3790                3795

Glu Glu Glu Glu Glu Val Gln Leu Lys Ser Ala Arg Arg Ala Thr
    3800            3805                3810

Ser Met Asp Leu Pro Met Pro Met Arg Phe Arg His Leu Lys Lys
    3815            3820                3825

Thr Ser Lys Glu Ala Val Gly Val Tyr Arg Ser Pro Ile His Gly
    3830            3835                3840

Arg Gly Leu Phe Cys Lys Arg Asn Ile Asp Ala Gly Glu Met Val
    3845            3850                3855

Ile Glu Tyr Ala Gly Asn Val Ile Arg Ser Ile Gln Thr Asp Lys
    3860            3865                3870

Arg Glu Lys Tyr Tyr Asp Ser Lys Gly Ile Gly Cys Tyr Met Phe
    3875            3880                3885

Arg Ile Asp Asp Ser Glu Val Val Asp Ala Thr Met His Gly Asn
    3890            3895                3900

Ala Ala Arg Phe Ile Asn His Ser Cys Glu Pro Asn Cys Tyr Ser
    3905            3910                3915

Arg Val Ile Asn Ile Asp Gly Gln Lys His Ile Val Ile Phe Ala
    3920            3925                3930

Met Arg Lys Ile Tyr Arg Gly Glu Glu Leu Thr Tyr Asp Tyr Lys
    3935            3940                3945

Phe Pro Ile Glu Asp Ala Ser Asn Lys Leu Pro Cys Asn Cys Gly
    3950            3955                3960

Ala Lys Lys Cys Arg Lys Phe Leu Asn
    3965            3970

<210> SEQ ID NO 4
<211> LENGTH: 20
<212> TYPE: DNA
<213> ORGANISM: Artificial
<220> FEATURE:
<223> OTHER INFORMATION: Reverse primer for creating TASP1 knockout in
      human locus via CRISPR

<400> SEQUENCE: 4
gtcattagcc atgtgtccgt                                              20

<210> SEQ ID NO 5
<211> LENGTH: 20
<212> TYPE: DNA
<213> ORGANISM: Artificial
<220> FEATURE:
<223> OTHER INFORMATION: Forward primer for creating TASP1 knockout in
      human locus via CRISPR

<400> SEQUENCE: 5
```

```
ccccataggg gtggaatgta                                              20
```

```
<210> SEQ ID NO 6
<211> LENGTH: 19
<212> TYPE: PRT
<213> ORGANISM: Homo sapiens

<400> SEQUENCE: 6

Lys Ile Ser Gln Leu Asp Gly Val Asp Asp Gly Thr Glu Ser Asp Thr
1               5                   10                  15

Ser Val Thr

<210> SEQ ID NO 7
<211> LENGTH: 19
<212> TYPE: PRT
<213> ORGANISM: Homo sapiens

<400> SEQUENCE: 7

Arg Ile Glu Gln Leu Asp Gly Val Asp Asp Gly Thr Asp Ser Glu Ala
1               5                   10                  15

Glu Ala Val

<210> SEQ ID NO 8
<211> LENGTH: 19
<212> TYPE: PRT
<213> ORGANISM: Homo sapiens

<400> SEQUENCE: 8

Leu Val Leu Gln Val Asp Gly Thr Gly Asp Thr Ser Ser Glu Glu Asp
1               5                   10                  15

Glu Asp Glu

<210> SEQ ID NO 9
<211> LENGTH: 19
<212> TYPE: PRT
<213> ORGANISM: Artificial
<220> FEATURE:
<223> OTHER INFORMATION: Mutant form of human MLL1 protein having a
      T2724A substituteion and a S2726A substitution

<400> SEQUENCE: 9

Lys Ile Ser Gln Leu Asp Gly Val Asp Asp Gly Ala Glu Ala Asp Thr
1               5                   10                  15

Ser Val Thr

<210> SEQ ID NO 10
<211> LENGTH: 19
<212> TYPE: PRT
<213> ORGANISM: Artificial
<220> FEATURE:
<223> OTHER INFORMATION: Mutant form of human MLL1 protein having a
      T2724D substituteion and a S2726D substitution

<400> SEQUENCE: 10

Lys Ile Ser Gln Leu Asp Gly Val Asp Asp Gly Asp Glu Asp Asp Thr
1               5                   10                  15

Ser Val Thr

<210> SEQ ID NO 11
<211> LENGTH: 19
<212> TYPE: PRT
<213> ORGANISM: Artificial
<220> FEATURE:
```

```
<223> OTHER INFORMATION: Mutant form of human TFIIA protein having a
      S280A substitution and a S281A substitution

<400> SEQUENCE: 11

Leu Val Leu Gln Val Asp Gly Thr Gly Asp Thr Ala Ala Glu Glu Asp
1               5                   10                  15

Glu Asp Glu

<210> SEQ ID NO 12
<211> LENGTH: 19
<212> TYPE: PRT
<213> ORGANISM: Artificial
<220> FEATURE:
<223> OTHER INFORMATION: Mutant form of human TFIIA protein having a
      S280D substitution and a S281D substitution

<400> SEQUENCE: 12

Leu Val Leu Gln Val Asp Gly Thr Gly Asp Thr Asp Asp Glu Glu Asp
1               5                   10                  15

Glu Asp Glu

<210> SEQ ID NO 13
<211> LENGTH: 11
<212> TYPE: PRT
<213> ORGANISM: Artificial
<220> FEATURE:
<223> OTHER INFORMATION: Mutant form of human MLL1 protein cleavage site

<400> SEQUENCE: 13

Gln Val Asp Gly Ala Asp Asp Leu Ser Thr Ser
1               5                   10

<210> SEQ ID NO 14
<211> LENGTH: 11
<212> TYPE: PRT
<213> ORGANISM: Artificial
<220> FEATURE:
<223> OTHER INFORMATION: Mutant form of human MLL1 protein cleavage site

<400> SEQUENCE: 14

Gln Leu Asp Gly Val Asp Asp Gly Thr Glu Ser
1               5                   10

<210> SEQ ID NO 15
<211> LENGTH: 11
<212> TYPE: PRT
<213> ORGANISM: Artificial
<220> FEATURE:
<223> OTHER INFORMATION: Mutant form of human MLL1 protein cleavage site

<400> SEQUENCE: 15

Gln Leu Asp Gly Val Asp Asp Gly Thr Asp Ser
1               5                   10

<210> SEQ ID NO 16
<211> LENGTH: 10
<212> TYPE: PRT
<213> ORGANISM: Artificial
<220> FEATURE:
<223> OTHER INFORMATION: Mutant form of human MLL1 protein cleavage site

<400> SEQUENCE: 16

Gln Val Asp Gly Thr Gly Asp Thr Ser Ser
1               5                   10
```

THERAPEUTIC TARGETING OF PROTEOLYTIC CLEAVAGE OF THE MIXED LINEAGE LEUKEMIA GENE PRODUCT (MLL1) BY TASPASE1 USING KINASE INHIBITORS

CROSS-REFERENCE TO RELATED PATENT APPLICATIONS

The present application claims the benefit of priority to U.S. Provisional Application No. 62/622,376, filed on Jan. 26, 2018, the content of which is incorporated herein by reference in its entirety.

STATEMENT REGARDING FEDERALLY SPONSORED RESEARCH OR DEVELOPMENT

This invention was made with government support under 5R35CA197569-03 awarded by the National Institutes of Health. The government has certain rights in the invention.

BACKGROUND

The field of the invention relates to methods for treating cancers. In particular, the field of the invention relates to methods, compounds, and compositions for treating cancers that are characterized by proteolytic cleavage of the mixed lineage leukemia gene product 1 (MLL1) by taspase1. Cancers treated by the disclosed methods, compounds, and compositions may include cancers characterized by rearrangements in the mixed lineage leukemia gene, otherwise referred to as "MLL-r cancers," including MLL-r leukemias, such as Acute Lymphoblastic Leukemia (ALL) and/or Acute Myeloid Leukemia (AML). The methods, compounds, and compositions disclosed herein relate to the use of therapeutic agents that inhibit cleavage of MLL1 by taspase1, either directly or indirectly. Therapeutic agents for use in the disclosed methods may include kinase inhibitors that inhibit kinases such as casein kinase II (CKII), which phosphorylates MLL1 and targets the phosphorylated MLL for endoproteolytic cleavage by taspase1.

Rearrangements or translocations of the mixed lineage leukemia gene (MLL-r) have been shown to be associated with aggressive forms of leukemia. Cases of acute lymphoblastic leukemia (ALL) and acute myelogenous leukemia (AML) that are characterized by MLL-r are extremely aggressive and are predominantly seen in infants and in therapy-related leukemias. In contrast to other types of leukemias, the prognosis for MLL-r is dismal and despite advances in new therapies, cure rates have plateaued over the last several years. Therefore, new therapies are needed.

The mixed lineage leukemia gene (MLL) is located on chromosome 11q23. Chromosomal rearrangements involving translocations between one copy of 11q23 and another chromosome can generate oncogenic fusion proteins consisting of an n-terminal portion of MLL and a c-terminal portion of the fusion partner. The normal in vivo function of MLL is as the enzymatic subunit of a COMPASS-like complex that methylates histone H3 on its fourth lysine. The chimeric protein lacks the c-terminal methyltransferase, but gains properties of the c-terminal fusion partner. Since many of the translocation partners for MLL are transcriptional activators, the aberrant recruitment of the translocation partner to normal MLL targets, which include oncogenes, drives leukemogenesis via aberrant transcription activation. Despite the chromosomal translocation, one wild-type copy of the MLL gene exists but the protein levels expressed from this allele are observed to be much lower than the MLL chimeric protein. Therefore, the present inventors hypothesized that a decrease in wild-type MLL protein levels observed in MLL-r may contribute to the development of leukemia and devised a scheme to modulate wild-type MLL protein levels and wild-type MLL protein activity.

Taspase1 is an endopeptidase that cleaves its protein substrates following an aspartate residue. To date, mixed-lineage leukemia 1 (MLL1), MLL2 and transcription factor TFIIA are the only known substrates proteolytically cleaved by taspase1 in mammalian cells. MLL1 and numerous MLL1 fusion proteins with chromosomal translocations are key epigenetic regulators in normal hematopoiesis and human leukemia. However, the biological significance of the cleavage of MLL1 remains debated in mammalian cells due to the different mouse models used in previous studies.

Here, we employed CRISPR/Cas9 targeted genome editing approach to completely knock out taspase1 in human cancer cell lines. We demonstrated that taspase1 cleavage destabilizes MLL1 protein and primes the protein to its degradation pathways without affecting its nuclear localization and activation. MLL1 association with the chromatin was remarkably increased in taspase1 knockout (KO) cells due to the resistance to degradation. Phosphorylation by casein kinase II (CKII) near the taspase1 cleavage site of MLL1 facilitated the cleavage process, and inhibition of CKII by small molecules partially blocked the conversion from full-length MLL1 to cleaved proteins. CKII inhibition resulted in the increase of genome-wide MLL1 occupancy and exclusion of Super Elongation Complex (SEC) recruitment in MLL leukemia cells. Therefore, loss of taspase1 inhibited cell proliferation partially through the MLL1-mediated gene expression alteration by modulating its stability and occupancy, and CKII inhibition may provide a therapy for MLL-r leukemia.

SUMMARY

Disclosed are methods, compounds, and compositions for treating cancer in a subject in need thereof, the cancer characterized by proteolytic cleavage by taspase1 of the mixed-lineage leukemia 1 gene product (MLL1). The methods include a step of administering to the subject a therapeutic agent that inhibits cleavage by taspase1 of MLL1, either directly or indirectly. Suitable therapeutic agents may include agents that inhibit the kinase activity of casein kinase II (CKII) where phosphorylation of MLL1 by CKII near the proteolytic cleavage site for taspase1 is required for cleavage by taspase1. Cancer treated by the disclosed methods and pharmaceutical compositions may include leukemia such as Acute Lymphoblastic Leukemia (ALL) and/or Acute Myeloid Leukemia (AML), particularly ALL and AML characterized by translocations in MLL1 and chimeric MLL1 fusion proteins, where treatment with CKII inhibitors may stabilize wild-type MLL1 which can displace the chimeric MLL1 fusion proteins from the Super Elongation Complex (SEC).

BRIEF DESCRIPTION OF THE FIGURES

FIG. 4. Full-length MLL1 displaces SEC occupancy at a subset of SEC target genes. Taspase1 WT and KO cells were transfected with Flag-MLLAF4 plasmid for 30 hours. ChIP-seq experiments were performed using antibody against ELL2. (A) Average plot showing the 867 binding regions of ELL2 with significant decrease in taspase1 KO cells compared to that in taspase1 WT 293T cells. (B) Average plot showing the MLL1 binding using MLL1N and MLL1C antibodies in taspase1 KO and WT 293T cells using the 867 regions identified in (A).

FIG. 10. Validation of MLL1 N-terminal and C-terminal antibodies in taspase1 WT and KO cells. Peak numbers of MLL1C and MLL1N in taspase1 WT and KO cells with shCtrl or shMLL1.

DETAILED DESCRIPTION

Figure 1:
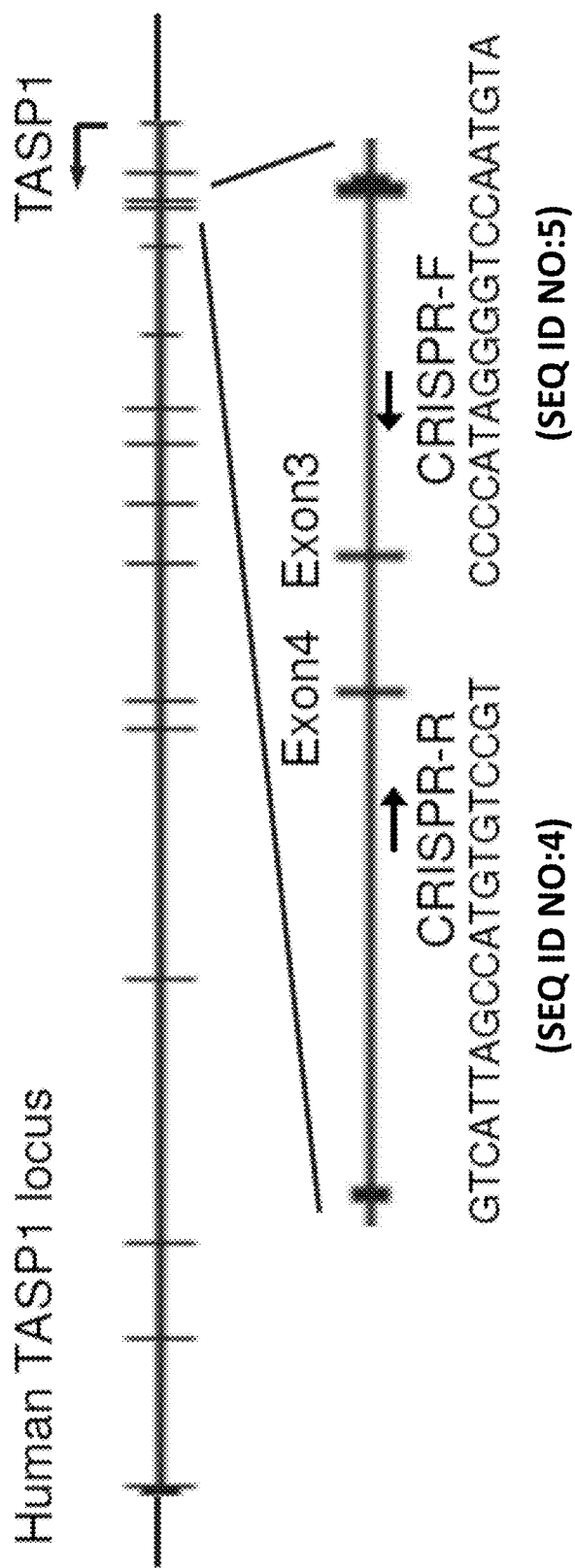
FIG. 1. Loss of taspase1 in 293T cells decreases cell proliferation without affecting the cellular localization of MLL1 and MLL2. (A) Generation of taspase1 knockout 293T cells by CRISPR/Cas9 targeted genome editing technology. (B) RNA-seq track showing the knockout of TASP1 gene in C49 and C104 clones. (C) Western blot showing the levels and molecular weight of MLL1, MLL2, TFIIA and taspase1, which are known substrates of taspase1 and the total histone H3K4me1, H3K4me2 and H3K4me3 levels. C45 is a heterozygous clone and C49 and C104 are KO clones of TASP1 gene. (D) Cell proliferation rate in taspase1 WT and KO 293T cells measured by cell counting. (E) 2-D colony formation in taspase1 WT and KO 293T cells. (F) Cellular fractionation showing that both cleaved and non-cleaved MLL1 and MLL2 were localized in the nuclear fraction. Full-length TFIIA was preferentially accumulated in the cytoplasmic fraction in taspase1 KO cells. Hsp90 and PARP are used as cytoplasmic and nuclear fraction biomarkers, respectively. (G) MLL1 N-terminal antibody is used in the immunofluorescence showing the nuclear localization of MLL1 proteins.
Figure 1:
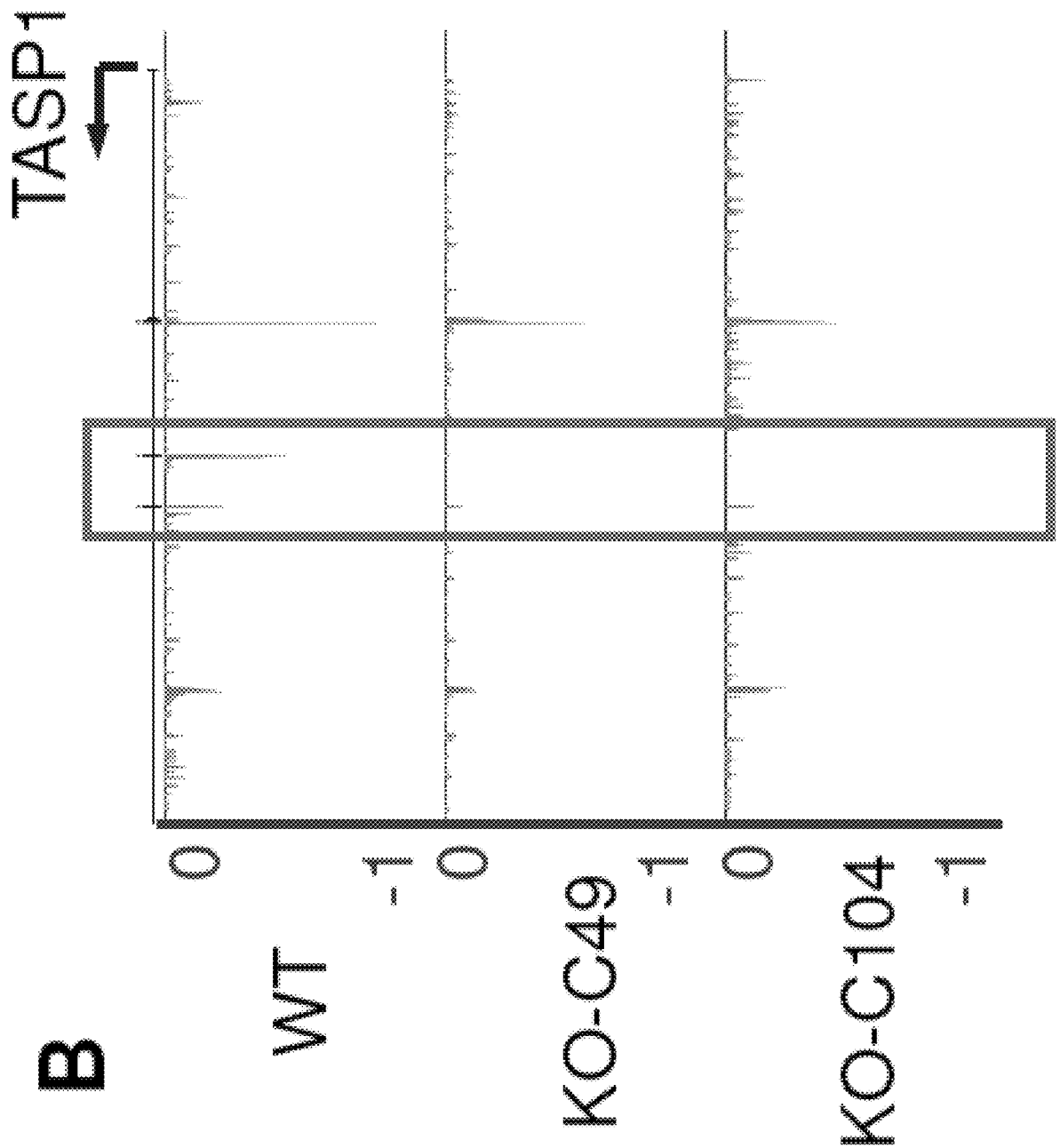
Figure 1:
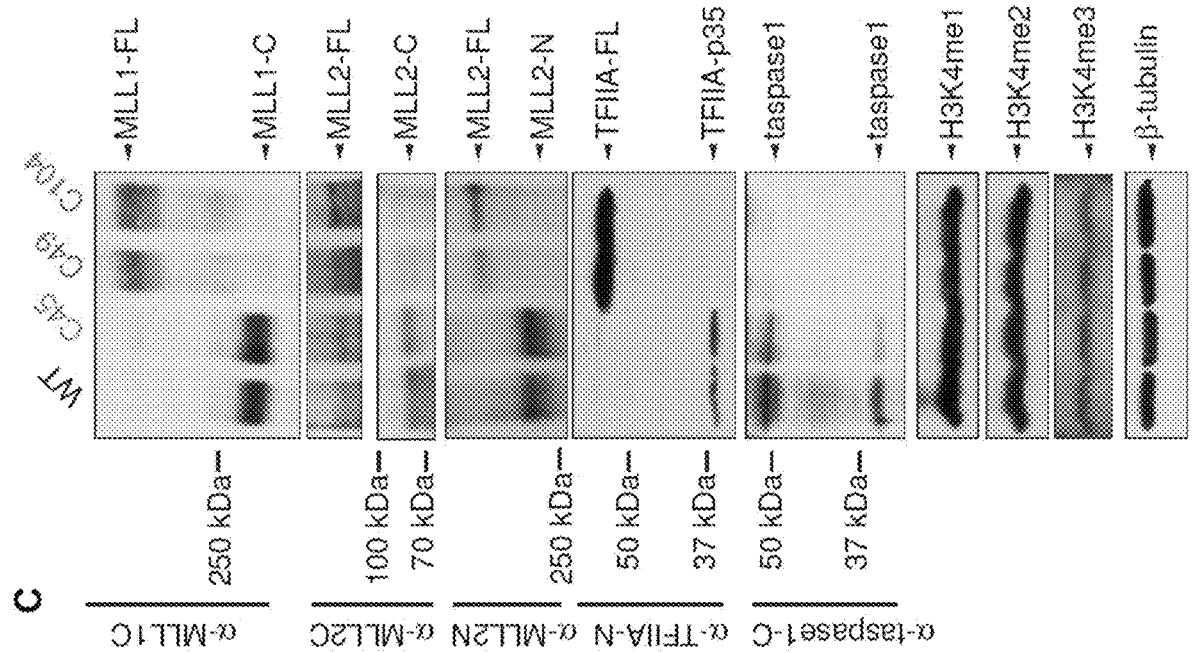
Figure 1:
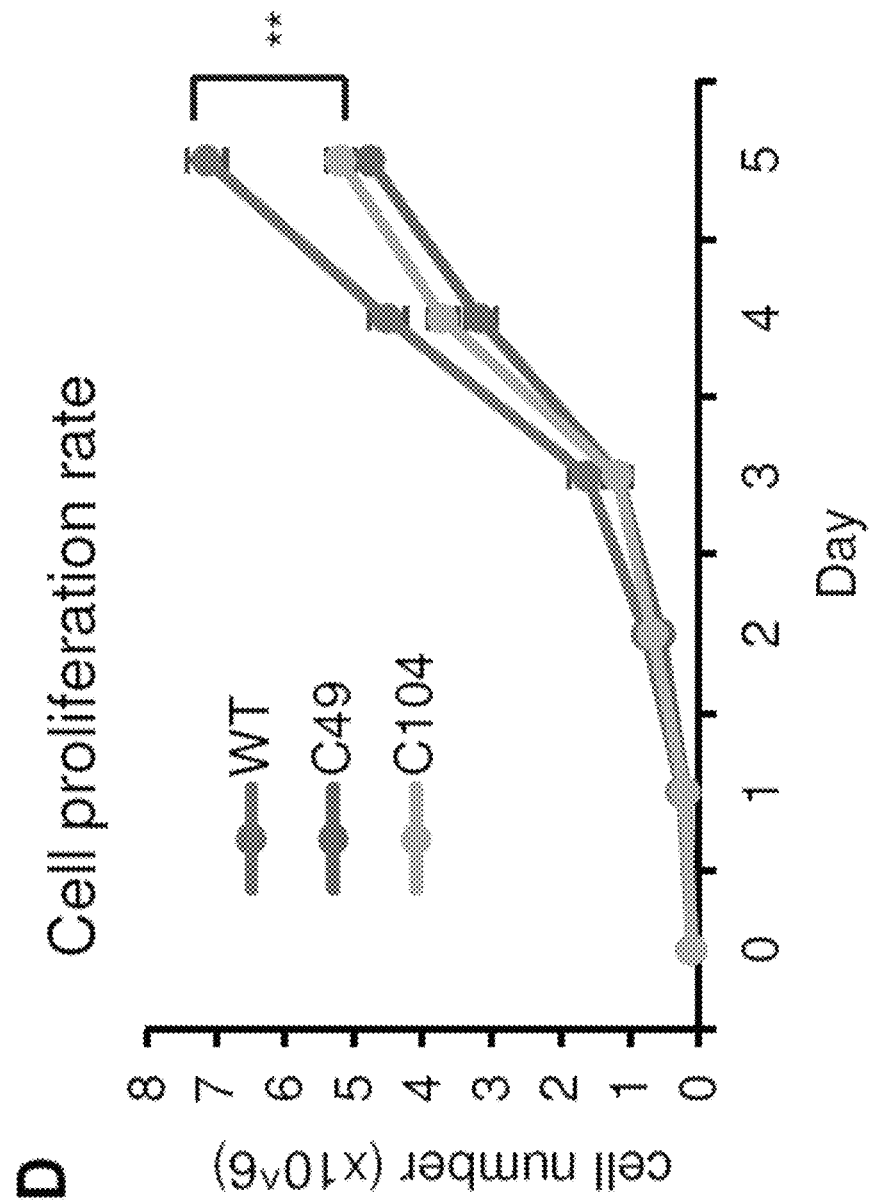
Figure 1:
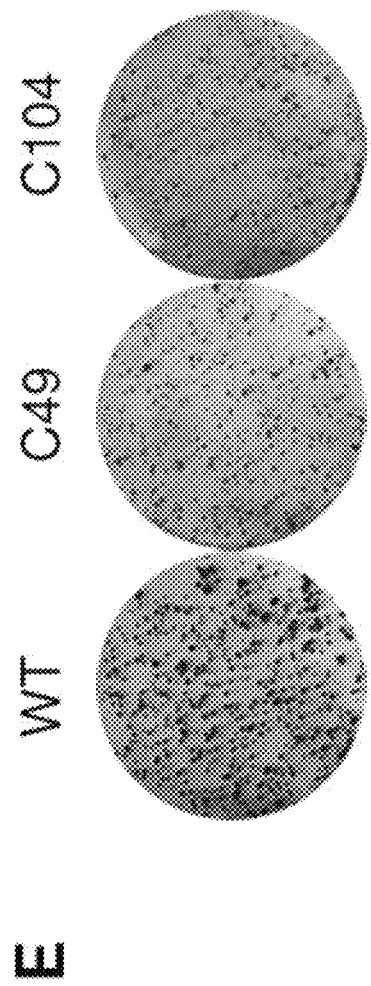
Figure 1:
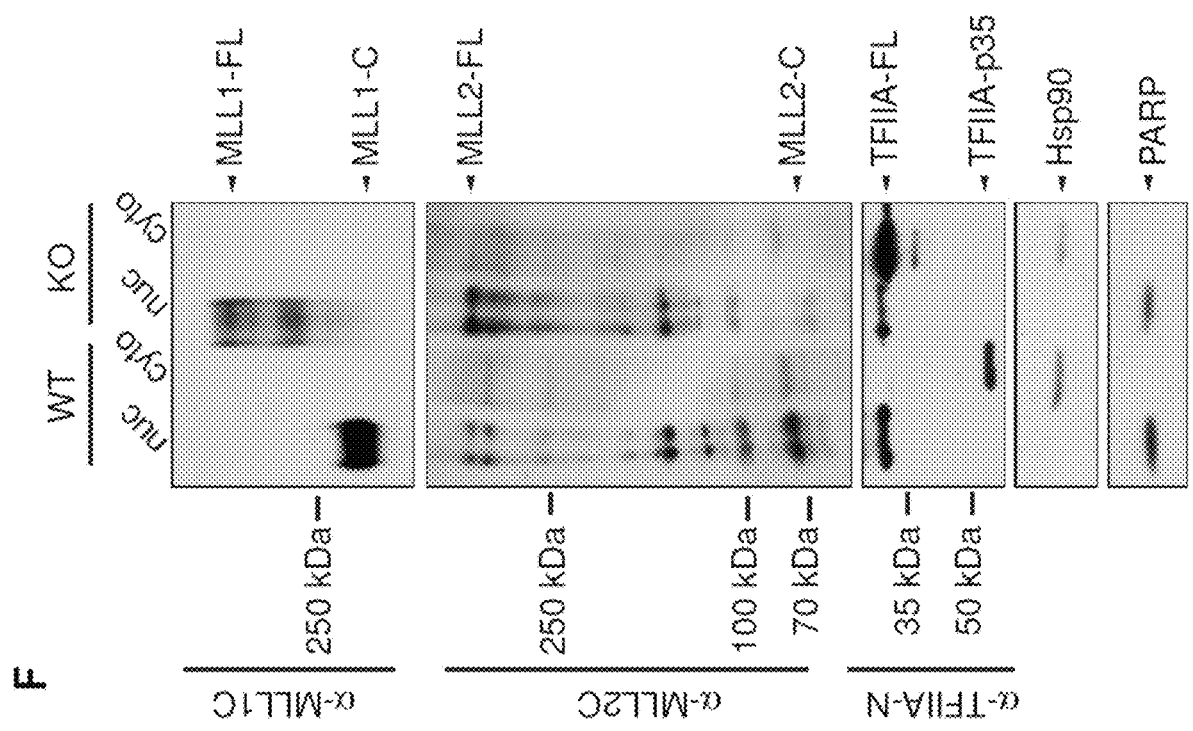
Figure 1:
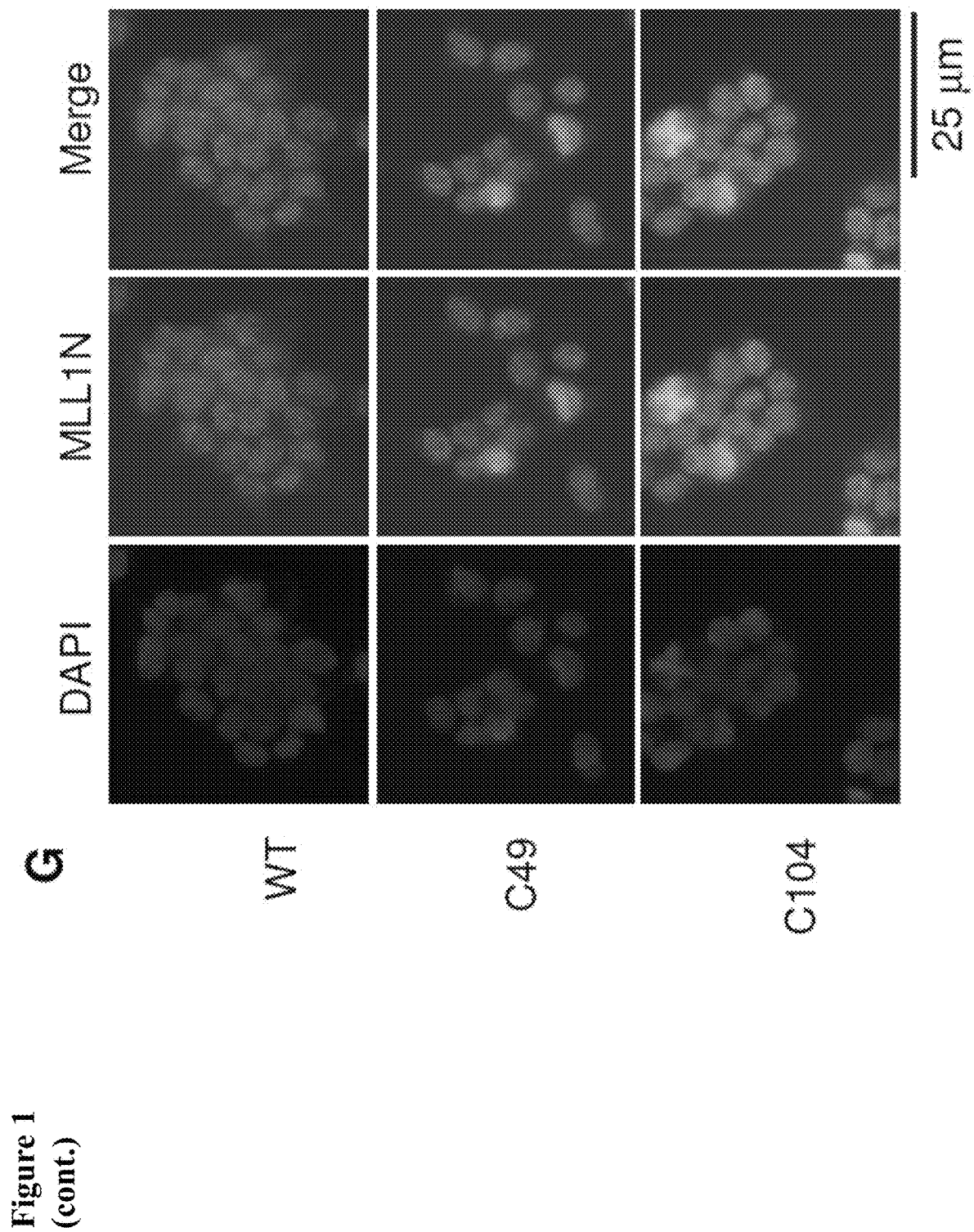

The present invention is described herein using several definitions, as set forth below and throughout the application.

Definitions

Unless otherwise specified or indicated by context, the terms "a", "an", and "the" mean "one or more." For example, "a compound" or "an inhibitor" should be interpreted to mean "one or more compounds" and "one or more inhibitors," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment, for example, treatment by include administering a therapeutic amount of one or more therapeutic agents that inhibit, either directly or indirectly, the proteolytic cleavage of mixed-lineage leukemia 1 protein (MLL1) by taspase1.

The mixed-lineage leukemia 1 (MLL1) gene may otherwise be referred to as Lysine [K]-specific MethylTransferase 2A or KMT2A) on chromosome 11q23. MLL1 may exist in several isoforms. The amino acid sequence of the full-length isoform 1 is provided herein as SEQ ID NO:1. The amino acid sequence of the full-length isoform 2 is provided herein as SEQ ID NO:2. The amino acid sequence of the full-length isoform 3 is provided herein as SEQ ID NO:3.

A "subject in need of treatment" may include a subject having a disease, disorder, or condition that is responsive to therapy with therapeutic agents that inhibit, either directly or indirectly, the proteolytic cleavage of mixed-lineage leukemia 1 protein (MLL1) by taspase1. For example, a "subject in need of treatment" may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "subject in need of treatment" may include a subject having a cancer that is characterized by proteolytic cleavage of MLL1 by taspase1 and that is responsive to therapy with therapeutic agents that inhibit, either directly or indirectly, the proteolytic cleavage of mixed-lineage leukemia 1 protein (MLL1) by taspase1. In particular, some leukemias such as acute lymphoblastic leukemia (ALL) or acute myelogenous leukemia (AML) may be treated by the disclosed methods, compounds, and pharmaceutical compositions.

A "subject in need of treatment" may include a subject having a cancer that is characterized by a rearrangement in the mixed lineage leukemia gene (e.g., via translocation), which may be referred to as a "MLL-r cancer" and which is responsive to an inhibitor of the proteolytic cleavage of wild-type MLL1 (e.g., a CKII inhibitor and/or a taspase1 inhibitor). In particular, some leukemia such as acute lymphoblastic leukemia (ALL) or acute myelogenous leukemia (AML) have been shown to be characterized by MLL-r. However, the present inventors' findings may be applicable to other cancers that are characterized by MML-r other than ALL and AML, including, but not limited to adenocarcinoma, lymphoma, melanoma, myeloma, sarcoma, and teratocarcinoma which are shown to be characterized by MLL-r. The present inventors' findings may be applicable to cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus which are shown to be characterized by MLL-r.

As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

Therapeutic Targeting of Proteolytic Cleavage of MLL1 by Taspase1 for Treating Cancer Disclosed are methods, compounds, and pharmaceutical compositions for treating a cancer in a subject in need thereof. Suitable cancers for treatment by the disclosed methods, compounds, and pharmaceutical compositions include cancers characterized by proteolytic cleavage by taspase1 of the mixed-lineage leukemia 1 gene product (MLL1). Suitable cancers may include cancers in which taspase1 is overexpressed in the cancer cells relative to normal cells. Suitable cancers may include cancers characterized by a rearrangement in the mixed lineage leukemia gene (e.g., via translocation), which may be referred to as a "MLL-r cancer" and which is responsive to an inhibitor of the proteolytic cleavage of wild-type MLL1 (e.g., a CKII inhibitor and/or a taspase1 inhibitor)

In some embodiments, cancers treated by the disclosed methods, compounds, and pharmaceutical composition are leukemia or lymphoma. In particular, cancers treated by the disclosed methods, compounds, and pharmaceutical compositions may include Acute Lymphoblastic Leukemia (ALL) and/or Acute Myeloid Leukemia (AML).

Suitable cancers treated by the disclosed methods, compounds, and pharmaceutical compositions may include cancers characterized by proteolytic cleavage of MLL1 by taspase1. In some embodiments, the proteolytic cleavage is a proteolytic cleavage between amino acid 2718 (aspartic acid) and amino acid 2681 (glycine) of SEQ ID NO:1; or between amino acid 2680 (aspartic acid) and amino acid 2719 (glycine) of SEQ ID NO:2; or between amino acid 2721 (aspartic acid) and amino acid 2722 (glycine) of SEQ ID NO:3.

The disclosed methods and pharmaceutical compositions utilize or include a therapeutic agent that inhibits cleavage by taspase1 of MLL1. The therapeutic agent may inhibit cleavage of MLL1 by taspase1, directly or indirectly.

In some embodiments, the therapeutic agent inhibits cleavage of MLL1 by taspase1 indirectly. For example, prior to being cleaved by taspase1, MLL1 must be phosphorylated at serine and/or threonine residues near the cleavage site (e.g., within 20 amino acids downstream of the proteolytic cleavage site). In some embodiments of the disclosed methods and pharmaceutical compositions, the therapeutic agent inhibits cleavage of MLL1 by taspase1 indirectly inhibiting phosphorylation of MLL1 at one or more serine or threonine residues.

In particular, suitable therapeutic agents for the disclosed methods and pharmaceutical compositions may include therapeutic agents that inhibit the kinase activity of casein kinase II (CKII). Inhibitors of CKII are known in the art.

Suitable CKII inhibitors for the disclosed methods and pharmaceutical compositions may include, but are not limited to, compounds or a pharmaceutical salts thereof disclosed in U.S. Pat. Nos. 7,956,064; 8,168,651; 8,367,681; 8,575,177, 8,853,234; 8,853,235; 9,062,043; 9,303,033; the contents of which are incorporated herein by reference in their entireties. Suitable CKII inhibitors for the disclosed methods and pharmaceutical compositions may include, but are not limited to, compounds or a pharmaceutical salts thereof disclosed in U.S. Published Application Nos. 2014/0094448; 2012/0208792; 2012/0190669; 2012/0129849; 2012/0122804; 2011/0263581; 2011/0218184; 2011/0160240; 2011/0152240; 2011/0112086; 2011/0071136; 2011/0071115; 2011/0065712; 2011/0065698; 2009/0264423; 2009/0215761; and 2009/0093465; the contents of which are incorporated herein by reference in their entireties.

More particularly, in some embodiments of the disclosed methods and pharmaceutical compositions, the therapeutic agent may comprise a compound having a formula or a pharmaceutical salt thereof:

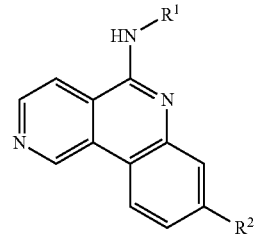

wherein:

$R^1$ is selected from hydrogen, halo, amino, cyano, hydroxyl, alkyl, alkenyl, alkynyl, C3-C8 cycloalkyl, or a saturated or unsaturated carbocycle or heterocycle comprising one 5- or 6-membered ring or comprising two or three fused 5- or 6-membered rings; optionally substituted at one or more positions with a substituent selected from halo, amino, cyano, hydroxyl, alkyl, alkenyl, or alkynyl; and $R^2$ is carboxyl, alkyl ester, carboxamido, acyl, cyano, a saturated or unsaturated carbocycle or heterocycle comprising one 5- or 6-membered ring or comprising two or three fused 5- or 6-membered rings.

Even more particularly, in some embodiments of the disclosed methods and pharmaceutical compositions, the therapeutic agent may comprise a compound having a formula or a pharmaceutical salt thereof:

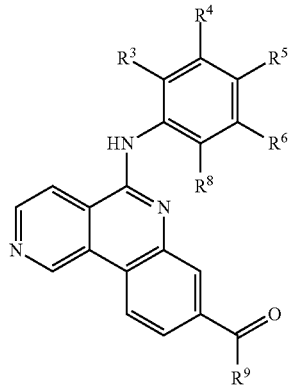

wherein:

R³, R⁴, R⁵, R⁶, R⁷, and R⁸ are selected from hydrogen, halo, amino, cyano, hydroxyl, alkyl, alkenyl, and alkynyl; and R⁹ is hydroxyl or alkoxy.

A particularly suitable compound for use in the disclosed methods may include a compound of the formula or a pharmaceutical salt thereof:

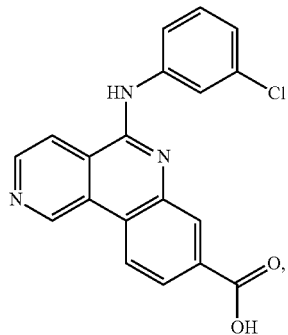 [SMILES: O=C(O)c1ccc2c(c1)nc(Nc1cccc(Cl)c1)c1ccncc12]

which otherwise is referred to as 5-(3-chlorophenylamino)benzo[c][2,6]naphthyridine-8-carboxylic acid or "CX-4945." (See Pierre et al., "Discovery and SAR of 5-(3-chlorophenylamino)benzo[c][2,6]naphthyridine-8-carboxylic acid (CX-4945), the first clinical stage inhibitor of protein kinase CK2 for the treatment of cancer," J. Med. Chem. 2011 Jan. 27; 54(2):635-54; the content of which is incorporated herein by reference in its entirety).

The compound referred to as CX-4945 and other inhibitors of CKII contemplated herein may be synthesized by Scheme 1:

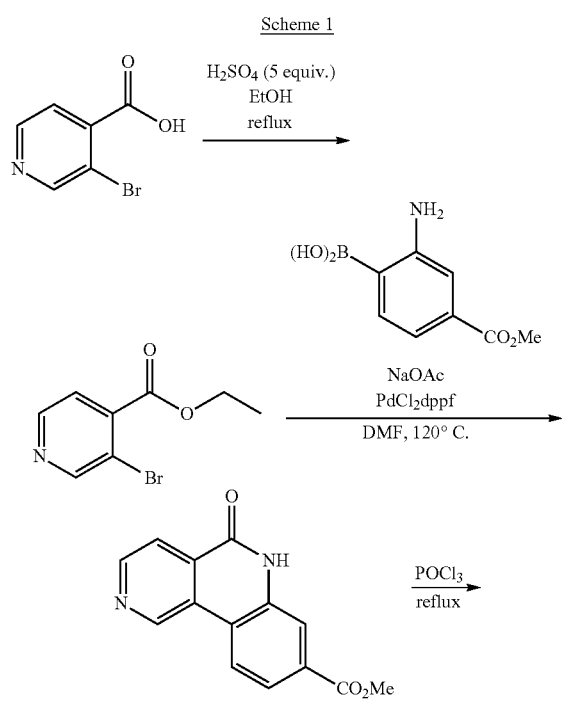

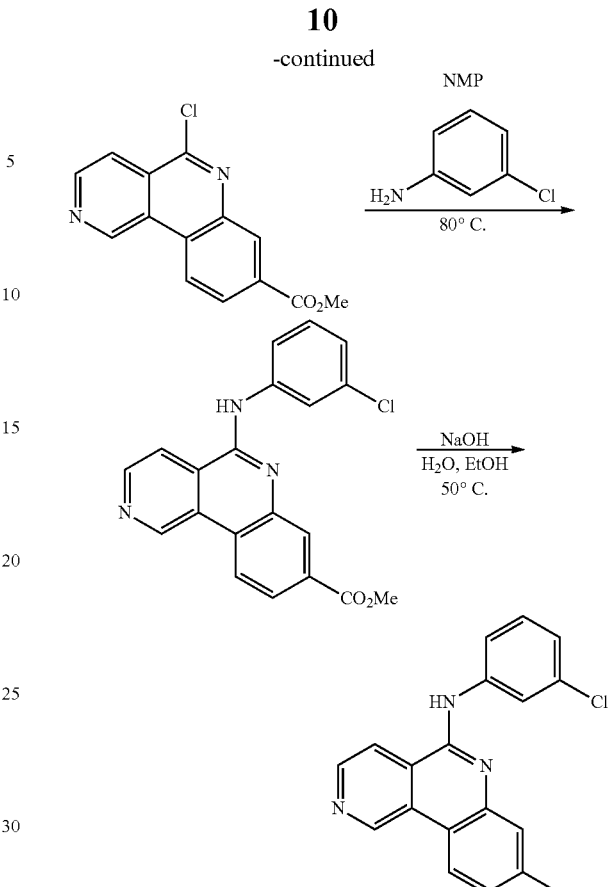

Other inhibitors of CKII are known in the art and may be suitable for the disclosed methods and pharmaceutical compositions. In particular, representative families of CKII inhibitors include carboxyl acid derivatives (see CX-4945 above), benzoimidazoles (e.g., 4,5,6,7-Tetrabromobenzotriazole (TBB), 2-dimethylamino-4,5,6,7-tetrabromobenzimidazole (DMAT)), anthraquinones (e.g., emodin), coumarins (e.g., 3,8-dibromo-7-hydroxy-4-methylchromen-2-one (DBC)), flavones (e.g., fisetin), pyrazolo-triazines (e.g., 8h), and thieno-pyrimidines (e.g., 3-[[5-(4-Methylphenyl)thieno[2,3-d]pyrimidin-4-yl]thio]propanoic acid (TTP 22)). (See Cozza, Pharmaceuticals, "The Development of CK2 Inhibitors: From Traditional_Pharmacology to in Silico Rational Drug Design," 2017, 10, 26, pages 1-23; and Pagano, "The selectivity of inhibitor of protein kinase CK2: an update," Biochem. J. 2008 Nov. 1; 415(3):353-65; the contents of which are incorporated herein by reference in their entireties).

In some embodiments of the disclosed methods and pharmaceutical compositions, the therapeutic agent may comprise an agent that inhibits the biological activity of taspase1 directly. For example, a suitable therapeutic agent may inhibit the proteolytic activity of taspase1 by binding to taspase1 or otherwise interacting with taspase1 to inhibit the proteolytic activity of taspase1. Suitable taspase1 inhibitors for the disclosed methods and pharmaceutical compositions may include, but are not limited to, compounds or a pharmaceutical salts thereof disclosed in U.S. Pat. Nos. 7,964,700; 8,501,811; the contents of which are incorporated herein by reference in their entireties. Suitable taspase1 inhibitors for the disclosed methods and pharmaceutical compositions may include peptidyl succinimidyl peptides as known in the art. (See, e.g., van den Boom et al., "Peptidyl Succinimidyl Peptides as Taspase 1 Inhibitors," ChemBioChem, 2014, 15, 2233-2237, the content of which is incorporated herein by reference in its entirety).

Formulations and Administration

The formula of the compounds disclosed herein should be interpreted as encompassing all possible stereoisomers, enantiomers, or epimers of the compounds unless the formulae indicates a specific stereoisomer, enantiomer, or epimer. The formulae of the compounds disclosed herein should be interpreted as encompassing salts, esters, amides, or solvates thereof of the compounds (e.g., pharmaceutically acceptable salts).

The disclosed therapeutic agents may be effective in inhibiting cell proliferation of cancer cells, including mixed lineage leukemia cells. Cell proliferation and inhibition thereof by the presently disclosed therapeutic agents may be assessed by cell viability methods disclosed in the art including colorimetric assays that utilize dyes such as MTT, XTT, and MTS to assess cell viability. Preferably, the disclosed therapeutic agents have an $IC_{50}$ of less than about 10 μM, 5 μM, 1 μM, or 0.5 μM in the selected assay.

The therapeutic agents utilized in the methods disclosed herein may be formulated as pharmaceutical compositions that include: (a) a therapeutically effective amount of one or more of the therapeutic agents as disclosed herein; and (b) one or more pharmaceutically acceptable carriers, excipients, or diluents. The pharmaceutical composition may include the therapeutic agent in a range of about 0.1 to 2000 mg (preferably about 0.5 to 500 mg, and more preferably about 1 to 100 mg). The pharmaceutical composition may be administered to provide the therapeutic agent at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a subject (e.g., after about 1, 2, 3, 4, 5, or 6 hours post-administration), the concentration of the therapeutic agent at the site of action is about 2 to 10 μM.

The therapeutic agents utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The therapeutic agents utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The therapeutic agents utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The therapeutic agents utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The therapeutic agents utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the therapeutic agents may be adapted for administration by any appropriate route, for example by the oral (including buccal or sublingual), or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Illustrative Embodiments

The following embodiments are illustrative and should not be interpreted to limit the scope of the claimed subject matter.

Embodiment 1. A method for treating a cancer in a subject in need thereof, the cancer characterized by proteolytic cleavage by taspase1 of the mixed-lineage leukemia 1 gene product (MLL1), the method comprising administering to the subject a therapeutic agent that inhibits cleavage by taspase1 of MLL1.

Embodiment 2. The method of embodiment 1, wherein the cancer is characterized by a rearrangement in the mixed lineage leukemia gene (MLL-r).

Embodiment 3. The method of embodiment 1 or 2, wherein the cancer is leukemia.

Embodiment 4. The method of any of the foregoing embodiments, wherein the cancer is Acute Lymphoblastic Leukemia (ALL) and/or Acute Myeloid Leukemia (AML).

Embodiment 5. The method of any of the foregoing embodiments, wherein the proteolytic cleavage is a proteolytic cleavage between amino acid 2718 (aspartic acid) and amino acid 2681 (glycine) of SEQ ID NO:1; or between amino acid 2680 (aspartic acid) and amino acid 2719 (glycine) of SEQ ID NO:2; or between amino acid 2721 (aspartic acid) and amino acid 2722 (glycine) of SEQ ID NO:3.

Embodiment 6. The method of any of the foregoing embodiments, wherein the therapeutic agent inhibits phosphorylation of MLL1 at one or more serine or threonine residues.

Embodiment 7. The method of any of the foregoing embodiments, wherein the therapeutic agent inhibits phosphorylation of the MLL1 gene product at one or more serine or threonine residues located downstream of the site of the proteolytic cleavage optionally within 20 amino acids downstream of the site of the proteolytic cleavage.

Embodiment 8. The method of any of the foregoing embodiments, wherein the therapeutic agent inhibits the kinase activity of casein kinase II (CKII).

Embodiment 9. The method of any of the foregoing embodiments, wherein the therapeutic agent comprises a compound or a pharmaceutical salt thereof disclosed in U.S. Pat. No. 7,956,064 or 8,168,651.

Embodiment 10. The method of any of the foregoing embodiments, wherein the therapeutic agent comprises a compound having the following formula or a pharmaceutical salt thereof:

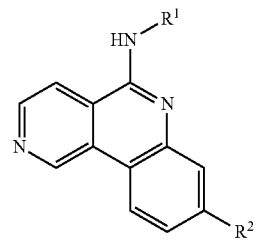

wherein:

R$^1$ is selected from hydrogen, halo, amino, cyano, hydroxyl, alkyl, alkenyl, alkynyl, C3-C8 cycloalkyl, or a saturated or unsaturated carbocycle or heterocycle comprising one 5- or 6-membered ring or comprising two or three fused 5- or 6-membered rings; optionally substituted at one or more positions with a substituent selected from halo, amino, cyano, hydroxyl, alkyl, alkenyl, or alkynyl; and R$^2$ is carboxyl, alkyl ester, carboxamido, acyl, cyano, a saturated or unsaturated carbocycle or heterocycle comprising one 5- or 6-membered ring or comprising two or three fused 5- or 6-membered rings.

Embodiment 11. The method of any of the foregoing embodiment wherein the therapeutic agent comprises a compound having the following formula or a pharmaceutical salt thereof:

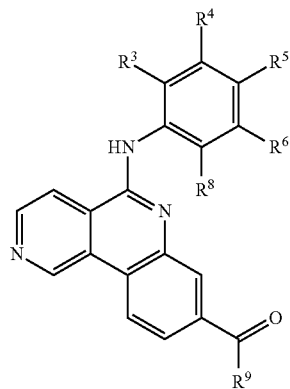

wherein:

R³, R⁴, R⁵, R⁶, R⁷, and R⁸ are selected from hydrogen, halo, amino, cyano, hydroxyl, alkyl, alkenyl, and alkynyl; and R⁹ is hydroxyl or alkoxy.

Embodiment 12. The method of any of the foregoing embodiments, wherein the therapeutic agent comprises a compound of the following formula or a pharmaceutical salt thereof:

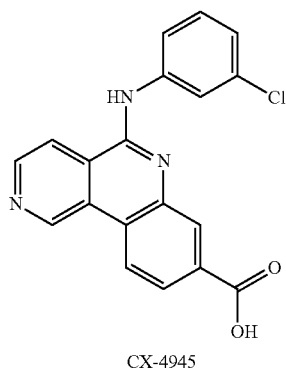 [SMILES: O=C(O)c1ccc2c(c1)nc(Nc1cccc(Cl)c1)c1ccncc12]

CX-4945

Embodiment 13. The method of any of the foregoing embodiment, wherein the therapeutic agents comprises an agent that inhibits the proteolytic activity of taspase1.

Embodiment 14. The method of any of the foregoing embodiments, wherein the therapeutic agent comprises a compound or a pharmaceutical salt thereof disclosed in U.S. Pat. No. 8,501,811.

EXAMPLES

The following Examples are illustrative and should not be interpreted to limit the scope of the claimed subject matter.

Title—Therapeutic Targeting of Childhood Leukemia by Pharmacological Inhibition of Proteolytic Cleavage of MLL1

Reference is made to the manuscript Zhao et al., "Regulation of MLL/COMPASS stability through its proteolytic cleavage by taspase1 as a possible approach for clinical therapy of leukemia," *Genes Dev.* Jan. 1, 2019 33: 61-74; Published in Advance Dec. 20, 2018, the content of which is incorporated herein by reference in its entirety.

Abstract

Chromosomal translocations of the Mixed-lineage leukemia 1 (MLL1) gene generating MLL-chimeras with numerous fusion partners have been demonstrated to drive pathogenesis of acute myeloid and lymphoid leukemia in children. Untranslocated MLL1 is a substrate for proteolytic cleavage by the endopeptidase, taspase 1, however, the biological significance of MLL1 cleavage by this endopeptidase remains unclear. Here, we employed CRISPR/Cas9 targeted genome editing approach to completely knockout taspase1 in human cancer cells and demonstrated that taspase1-dependent cleavage of MLL1 result in the stabilization of full-length MLL. Upon loss of taspase1, MLL1 association with chromatin is markedly increased due to the stabilization of its uncleaved version and this stabilization of the uncleaved MLL1 can result in the displacement of MLL-chimeras from chromatin. Our molecular and biochemical studies demonstrated that phosphorylation of MLL1 by casein kinase II (CKII) near its taspase1 cleavage site, facilitates the cleavage by the endopeptidase, and that the pharmacological inhibition of CKII blocks MLL1 cleavage, increasing its stability and the displacement of the MLL-chimeras from chromatin. Furthermore, inhibition of CKII in two independent mouse models of leukemia, resulted in the displacement of MLL-chimeras from chromatin, relieved the cellular oncogenic addiction to MLL chimeras and substantially delayed leukemic progression in animals. This study provides targeted therapeutic approaches for the treatment of aggressive MLL leukemia through the regulation of its cleavage by taspase 1.

Introduction

Threonine aspartase 1 (taspase1) is a unique endopeptidase that cleaves its protein substrates using threonine as the active nucleophile (Hsieh et al. 2003a). Taspase 1 was originally identified as the protease for MLL1, and later on, only limited numbers of taspase1 substrates were identified, which included MLL1, MLL2 and TFIIA in mammalian cells (Hsieh et al. 2003a; Takeda et al. 2006; Zhou et al. 2006) and HCF1 (dHCF1) in *Drosophila* (Capotosti et al. 2007). The proteolytic cleavage of TFIIA has been well documented: the uncleaved TFIIA is involved in active transcription in the nucleus whereas the cleaved TFIIA by taspase1 is less stable and targeted for proteasome-mediated degradation (Hoiby et al. 2004; Zhou et al. 2006). Although dHCF1 undergoes proteolytic maturation by *Drosophila* taspase1 (Capotosti et al. 2007), mammalian HCF1 is cleaved by N-acetylglucosamine (O-GlcNAc) transferase (OGT), which displays the species-specific divergence in this maturation process (Capotosti et al. 2011; Daou et al. 2011; Wunsch et al. 2015). In contrast to TFIIA and HCF, the biological significance of MLL1 cleavage by taspase1 is not clear (Hsieh et al. 2003a; Takeda et al. 2006; Yokoyama et al. 2013).

MLL1 is one of the members of the histone H3 lysine 4 (H3K4) methyltranferases found within the COMPASS (Complex proteins associated with Set1) family (Miller et al. 2001; Schuettengruber et al. 2017) that maintains H3K4 trimethylation (H3K4me3) on a subset of transcriptionally active genes in mouse embryonic fibroblasts (MEFs) and H3K4me2 predominantly at CpG-dense regions to regulate target gene expression (Wang et al. 2009; Rickels et al. 2016). Taspase1 proteolytically processes the full-length MLL1 protein into a 320 kDa N-terminal fragment (MLL1N) and a 180 kDa C-terminal fragment (MLL1C) at two conserved cleavage sites (D/GADD and D/GVDD motifs), and the two fragments further associate to form a stable dimer (Yokoyama et al. 2002; Hsieh et al. 2003a; Hsieh et al. 2003b). The N-terminal half of MLL1 contains AT hooks- (Zeleznik-Le et al. 1994), CXXC- and PHD/Bromo-domains which may function for DNA binding (Fair et al. 2001). The C-terminal half of MLL1 contains its transactivation domain and SET domain with histone H3K4 methyltransferase activity (Milne et al. 2002; Nakamura et al. 2002).

The MLL1 gene is found in chromosomal translocations with a large number of partner genes in childhood leukemia. In most cases, the leukemogenic fusion proteins contain the N-terminal half of MLL1 fused in frame to the C-terminal translocation partners. Consequently, the taspase1 cleavage sites are lost in these chimeric proteins. Therefore, the stability of these MLL-chimeras exceed the wild-type copy of MLL1 in the leukemic cells and fusion proteins drive the oncogenic target gene expression including HOXA4, HOXA5, HOXA9 and MEIS1 (Armstrong et al. 2002; Ayton and Cleary 2003; Wong et al. 2007; Wang et al. 2012a; Liang et al. 2017).

Different mouse models of leukemia have been established to study the biological consequences of MLL1 cleavage by taspase1 (Takeda et al. 2006; Yokoyama et al. 2013; Dong et al. 2014). However, no consistent conclusions have been reached due to the complexity of the mouse models. In one study, Taspase1$^{-/-}$ mice and knock-in mice with homozygous noncleavable alleles of MLL1 and/or MLL2 were generated (Takeda et al. 2006). Taspase1-deficient cells exhibited deregulated cell cycle genes and MEFs bearing the noncleavable (nc) alleles of MLL1 also showed proliferation defects, suggesting MLL1 is the crucial substrates for taspase1-coordinated cell proliferation (Takeda et al. 2006). In another study, the knock-in mice bearing homozygous noncleavable alleles of MLL1 displayed no apparent defects and MLL1$^{nc/nc}$ and MEFs bearing these mutations demonstrated normal pattern of proliferation with unaffected MLL target genes expression (Yokoyama et al. 2013). The controversies were raised from the complexity of the mouse models and the distinct downstream events examined (cell cycle genes and MLL1 target genes respectively). To address these inconsistencies, herein, we utilized CRISPR/Cas9 gene editing to completely knockout TASP1 gene in human cancer lines and characterized the functions of MLL1 cleavage by taspase1 in these cells and to determine the effect of taspase1 loss on MLL1 stability and the possibility of the use of this pathway for MLL-chimera therapy. Our study demonstrated that instead of activation and maturation of MLL1, taspase1 linked MLL1 to the degradation process and affected its turnover on chromatin for the proper gene expression independent of H3K4 methylation. Loss of taspase1 resulted in the inhibition of cellular growth partially through the increase of MLL1 occupancy and gene expression alterations. We also demonstrated that phosphorylation of MLL1 by casein kinase II (CKII) near MLL1-taspase1 cleavage site, facilitated the cleavage by the endopeptidase, and that the pharmacological inhibition of CKII blocks MLL1 cleavage, increased its stability and the displacement of the MLL-chimeras from chromatin. Furthermore, pharmacological inhibition of CKII resulted in alteration in MLL1 proteolytic cleavage, association of MLL-chimera on chromatin and relieving the cellular oncogenic addiction to MLL-chimeras. We showed that inhibition of MLL1 cleavage via this pathway can substantially delay leukemic progression in animals. This study provides targeted therapeutic approaches for the treatment of aggressive MLL leukemia through the regulation of its cleavage by taspase1.

Results

Loss of taspase1 decreases cellular proliferation without altering localization of MLL1 and MLL2. In order to systematically investigate the functions of taspase1 in mammalian cells and the potential therapeutic value in human cancers, we employed CRISPR/Cas9 technology to completely knock out taspase1 in several different cell-lines including 293T (FIG. 1A), MCF7 breast cancer, and HCT116 colorectal cancer cell-lines (FIGS. 8A and 8B). We generated two independent homozygous taspase1 knockout KO clones (C49 and C104) and verified both clones by RNA-sequencing (RNA-seq) at TASP1 gene locus (FIG. 1B). Loss of taspase1 in both C49 and C104 KO clones resulted defects in cleavage of MLL1, MLL2 and TFIIA, which are the known nuclear regulator substrates of taspase1 (Hsieh et al. 2003a; Takeda et al. 2006; Zhou et al. 2006), whereas the substrate cleavage was not affected in the heterozygous clone C45 (FIG. 1C, FIGS. 8A and 8B). The global histone H3K4 methylation levels (H3K4me1/2/3) as measured by Western analysis remained the same in taspase1 homozygous KO clones compared with WT cells (FIG. 1C and FIG. 8C). In both taspase1 clones, cellular proliferation rate was reduced and the colony formation ability of the cells was also diminished (FIGS. 1D and 1E).

Previous studies reported that the proteolytic cleavage of MLL1 by taspase1 maturated and activated MLL1 and enabled the translocation of MLL1 from the cytoplasm to nucleus for proper gene expression activation (Hsieh et al. 2003a; Zhang et al. 2013; Wang et al. 2016). In our study when taspase1 WT and KO 293T cell lysates were fractionated, both MLL1 and MLL2 were found solely in the nuclear fractions in both taspase1 WT and KO cells (FIG. 1F). Similar results observed with immunofluorescence studies where MLL1 and MLL2 staining overlapped with DAPI representing the nucleus in taspase1 WT and KO cells (FIG. 1G, and FIGS. 8D and 8E). Collectively, our study demonstrated that both the cleaved and non-cleavable MLL1 and MLL2 were present in the nucleus, suggesting the cellular localization of MLL1 and MLL2 is not affected by the loss of taspase1. Furthermore, RbBP5 interacted with both cleaved and non-cleavable MLL1 (FIG. 8F), and MLL1 proteins in taspase1 WT and KO cells eluted in the same fractionations in size exclusion chromatography (FIG. 8G), indicating MLL/COMPASS assembly is not altered in the taspase1 KO cells.

Figure 2:
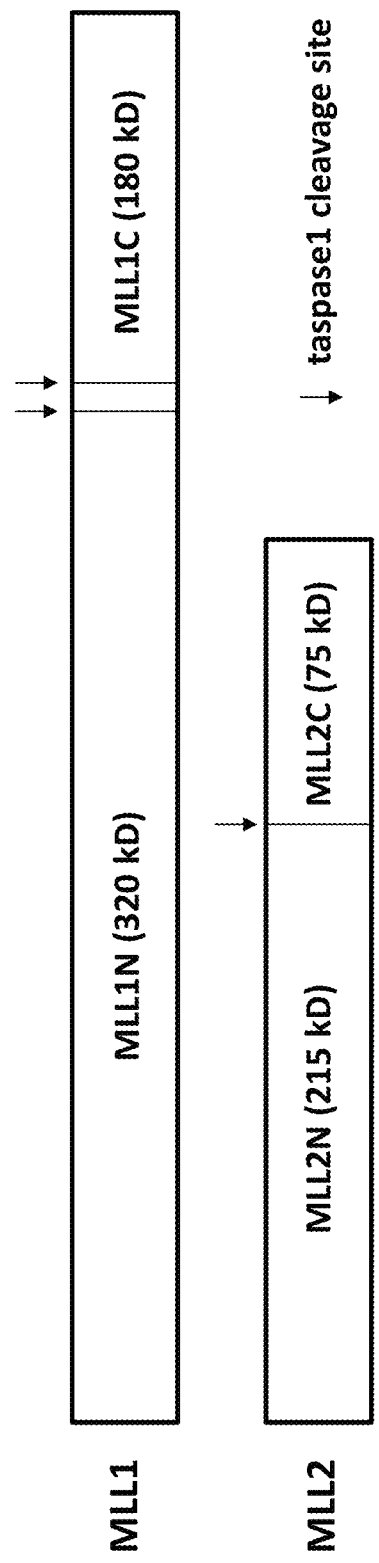
FIG. 2. MLL1 stability is increased without proteolytic cleavage. (A) Schematic diagram showing the cleavage of MLL1 and MLL2 by taspase1. (B) 293T taspase1 WT and KO cells were treated with 50 µg/ml cycloheximide (CHX) for 0 or 8 hrs. Cell lysates were collected and immunoblotted with MLL1, MLL2 and TFIIA. (C) and (D) MCF7 taspase1 WT and KO cells were treated with different concentrations of CHX (0, 10, 20 or 40 µg/ml) for 8 hrs. Cell lysates were collected and immunoblotted with MLL1, MLL2 and TFIIA. (E) and (F) HCT116 taspase1 WT and KO cells were treated with CHX (0, 5, 10 or 20 µg/ml) for 8 hrs. Cell lysates were collected and immunoblotted with MLL1. Quantification of MLL1 protein levels was performed with ImageJ.
Figure 2:
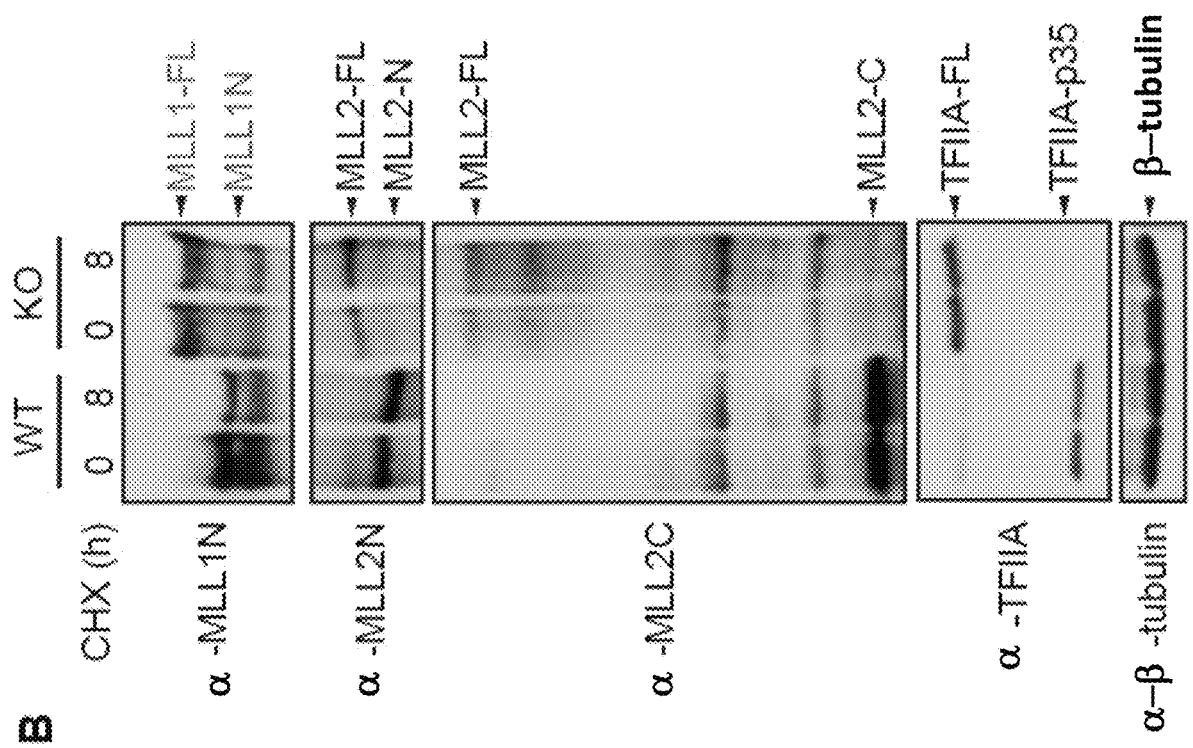
Figure 2:
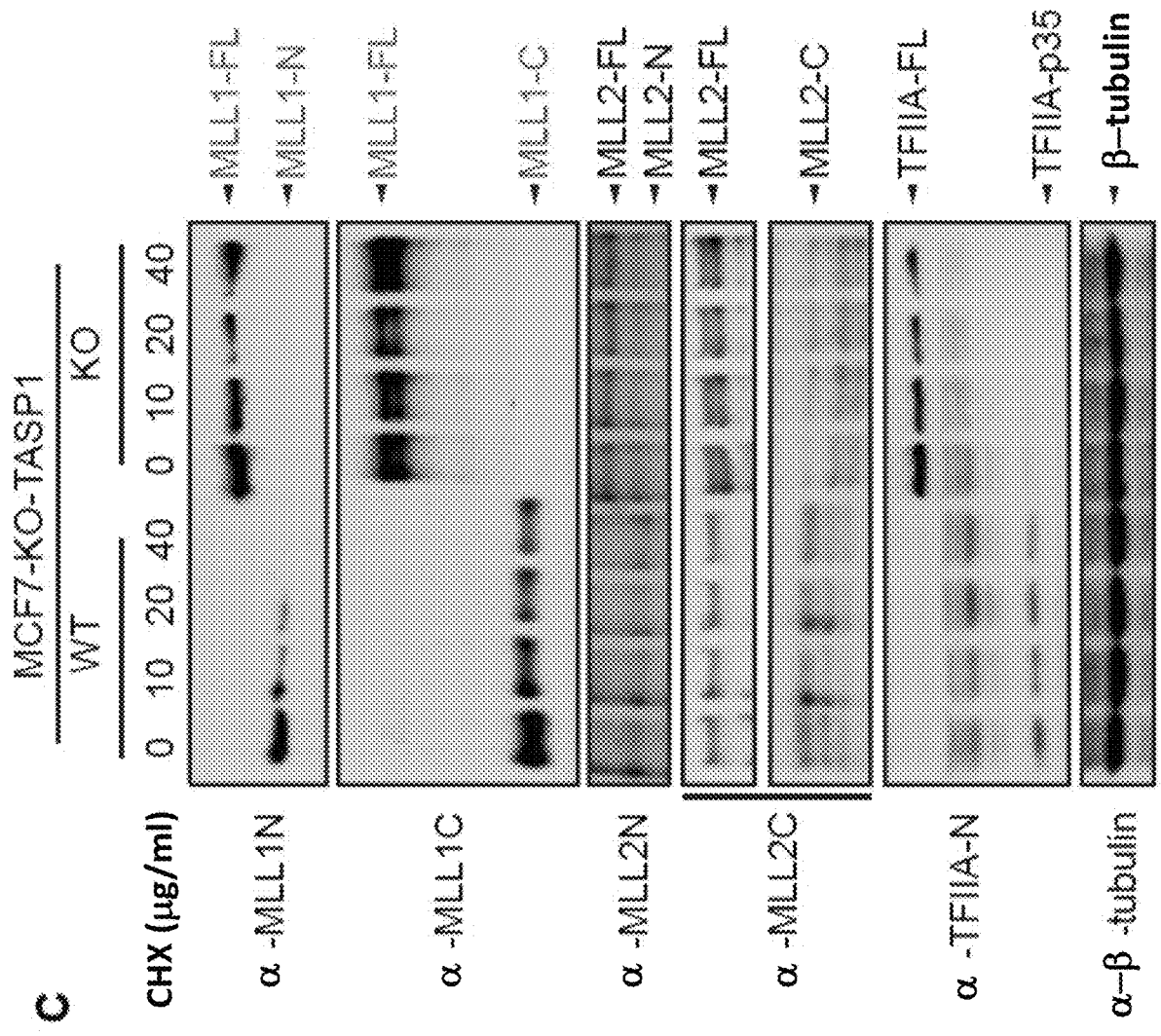
Figure 2:
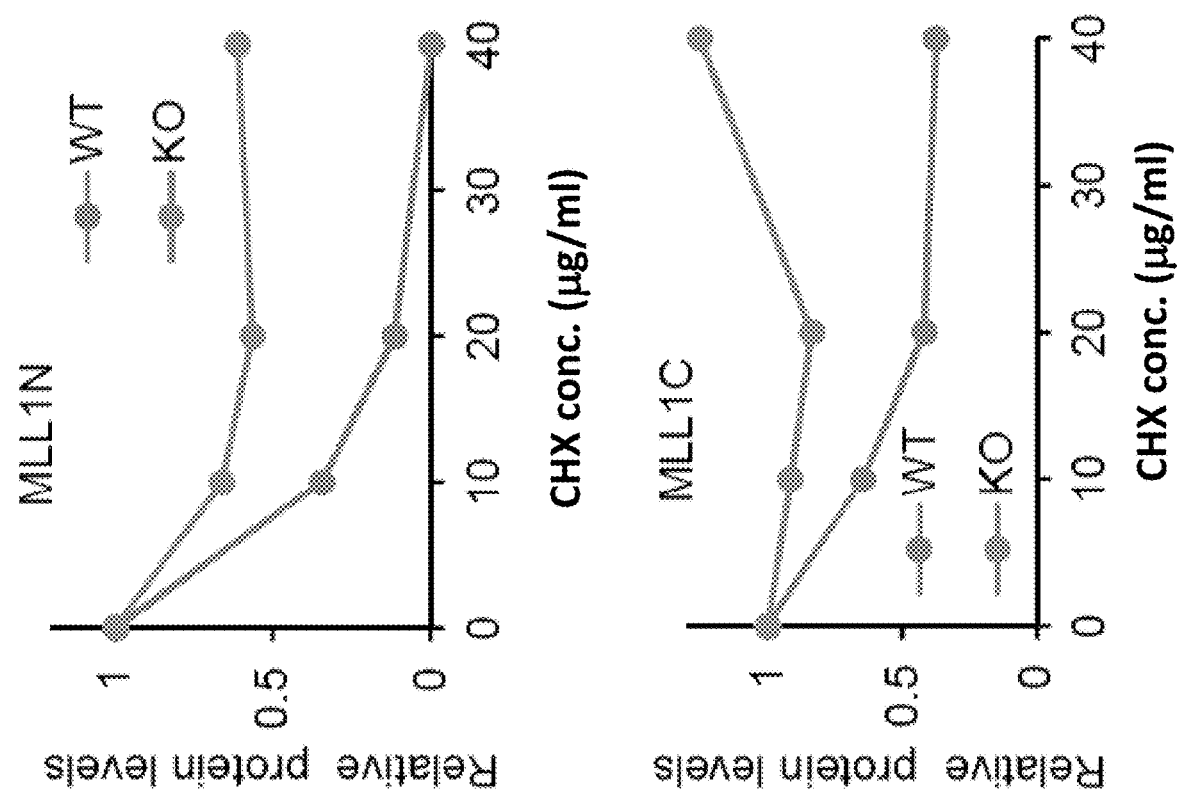
Figure 2:
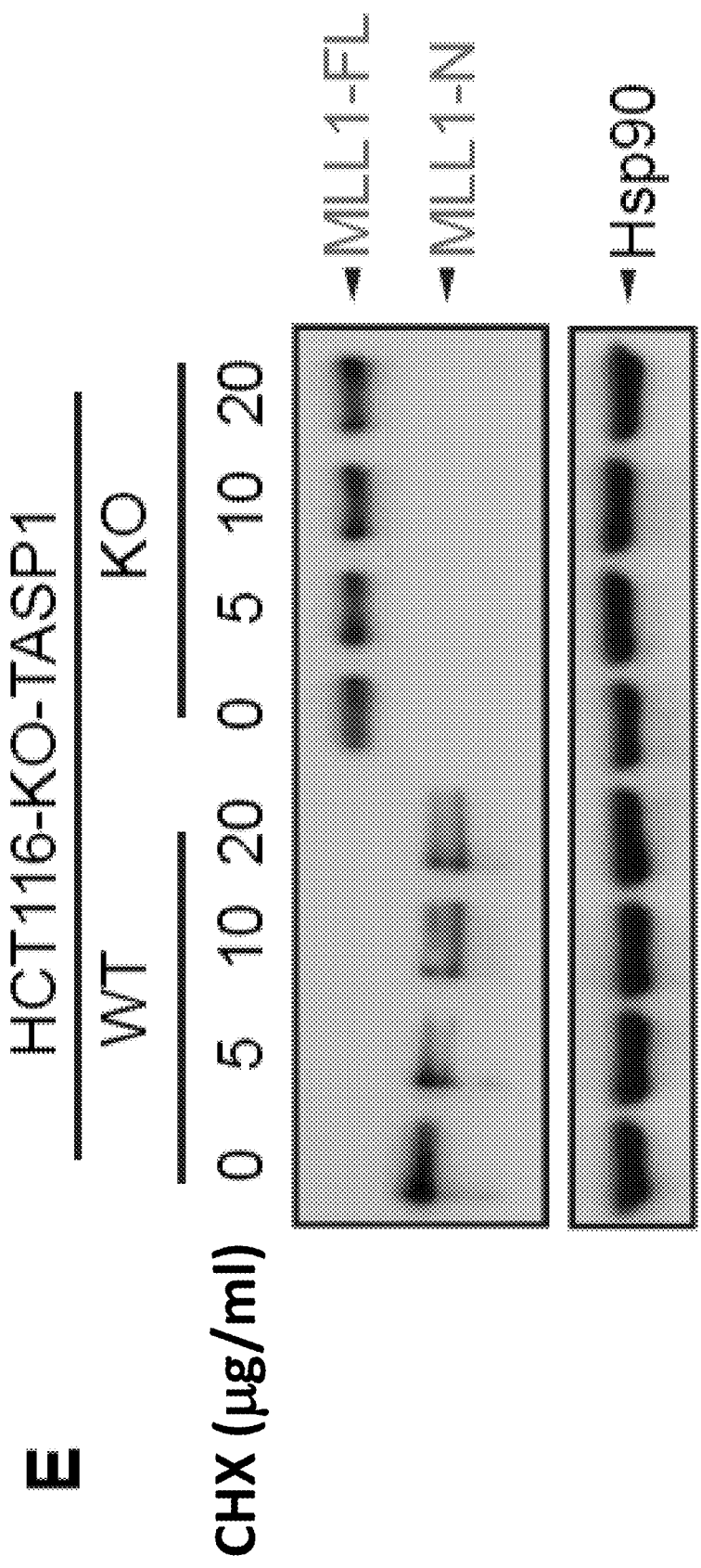
Figure 2:
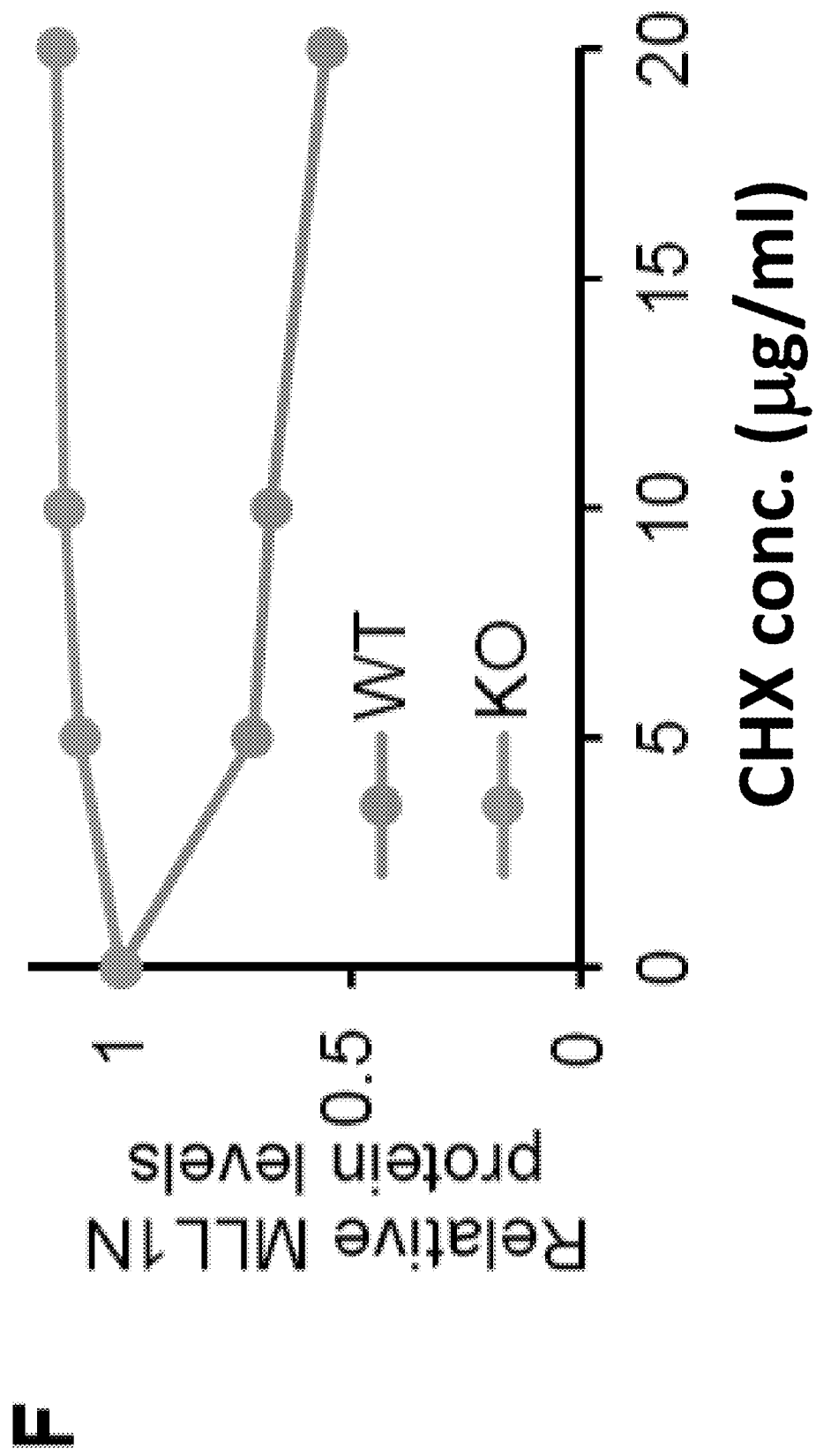
Figure 9:
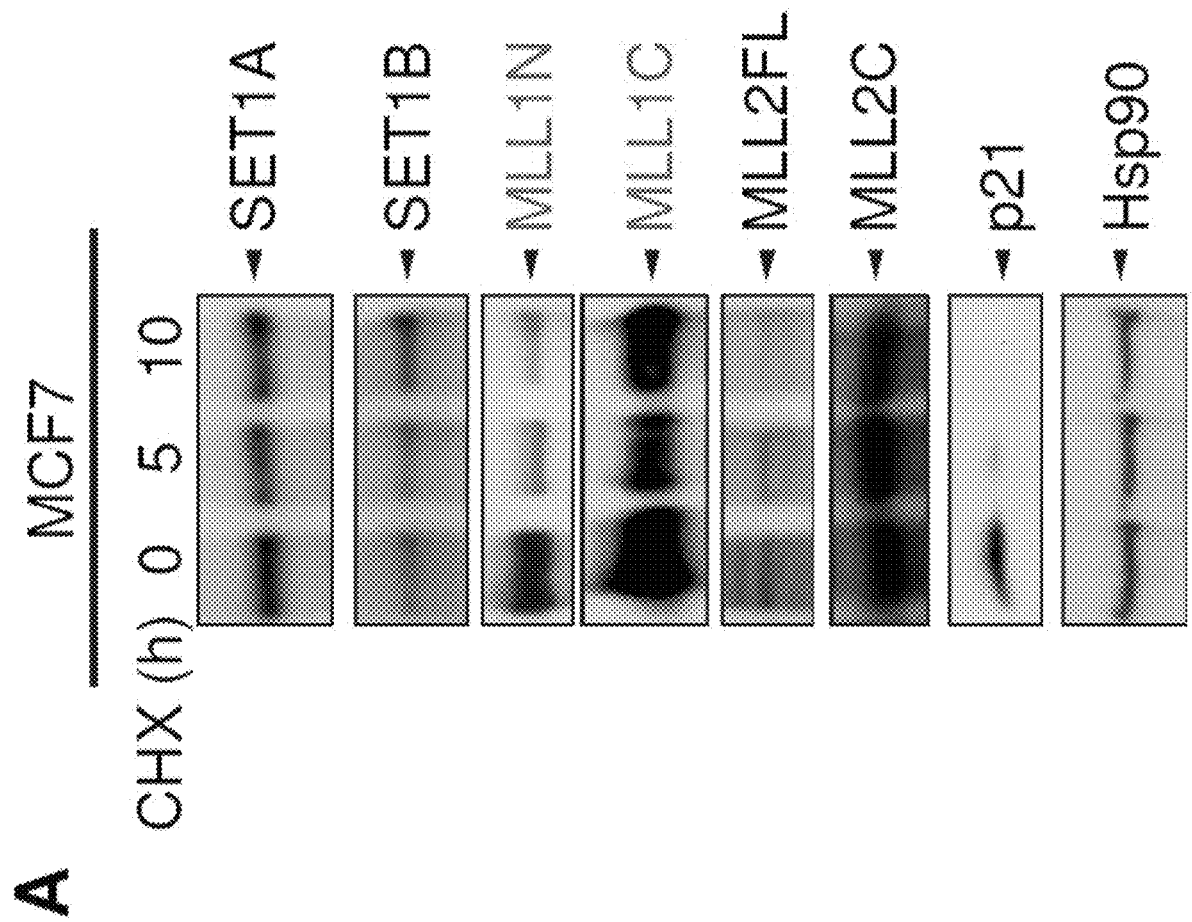
FIG. 9. MLL1 stability is highly regulated. MCF7 cells were treated with 40 µg/ml CHX for 0, 5 or 10 hrs. Protein levels of SET1A, SET1B, MLL1, MLL2 and p21 were determined by (A) Western blot and (B) quantified by ImageJ. p21 served as a positive control for CHX treatment.
Figure 9:
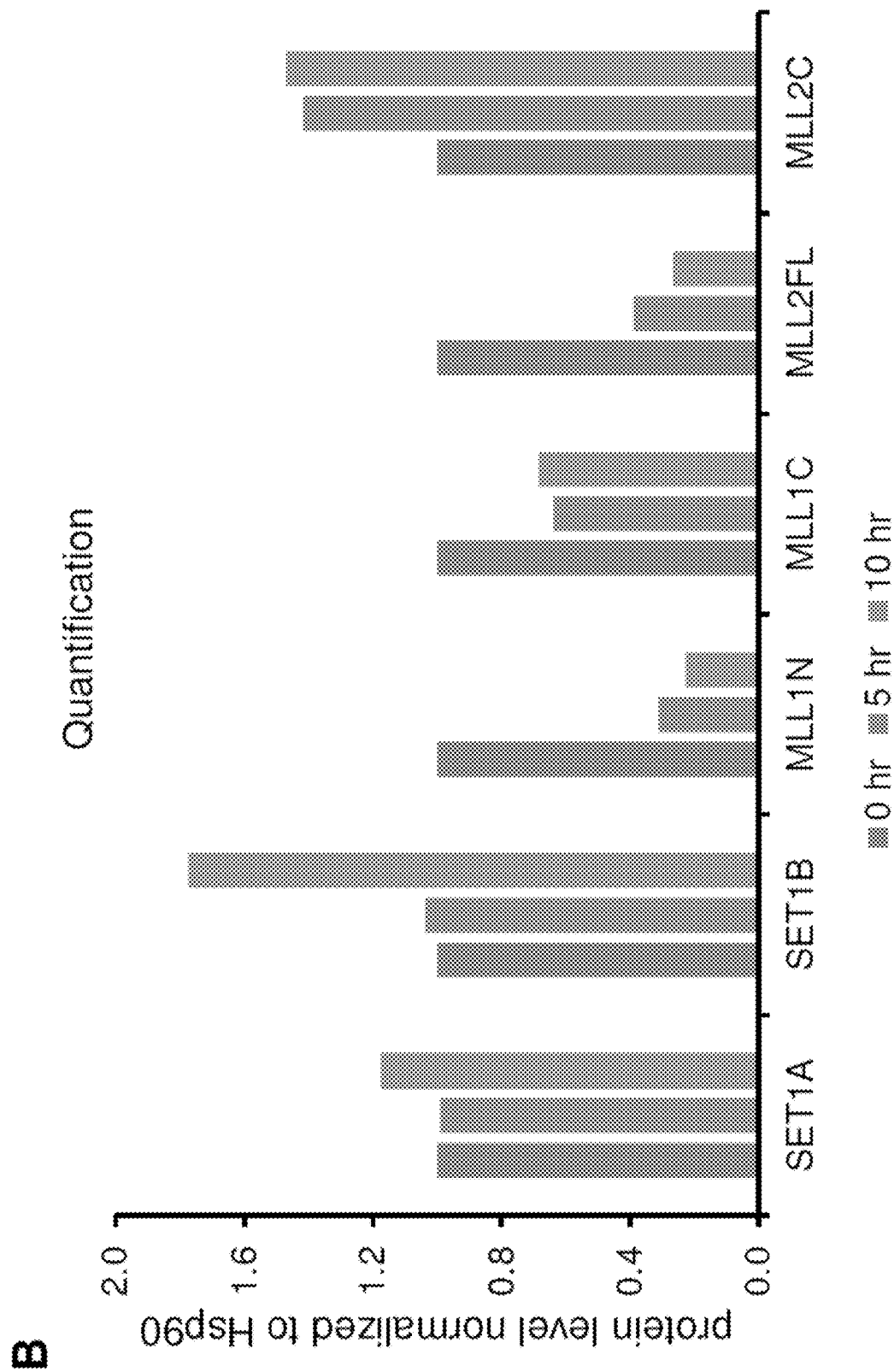

Taspase1-dependent MLL1 cleavage regulates MLL1 stability. Taspase1 has been shown to cleave TFIIA and target it for proteasomal degradation in the cytoplasm (Zhou et al. 2006). We also detect that MLL1 protein stability is highly regulated compared to other COMPASS family members (SET1A, SET1B and MLL2) as shown by the fast turnover with cycloheximide (CHX) induced protein degradation in cells within 10 hours of treatment (FIG. 9). However, it is not clear if MLL1 stability is also controlled by its taspase1-dependent proteolytic cleavage. This question triggered us to investigate MLL1 protein stability in taspase1 WT and KO cells we generated. First, we asked if that the mRNA transcripts for both KMT2A (MLL1) and KMT2B (MLL2) genes remained constant in taspase1 WT and KO cells (data not shown). We then, we performed CHX pulse-chase experiment to measure the MLL1 protein degradation rate in various taspase1 WT and KO cells (FIG. 2A-F). Upon treatment with CHX, MLL1 in WT cells were subject to proteasomal degradation while the non-cleavable MLL1 in taspase1 KO cells were relatively more resistant to CHX induced degradation (FIG. 2B). MLL2 and TFIIA proteins were not sensitive to CHX treatment in 293T cells during the same time frame and the protein levels remained constant in both WT and KO cells (FIG. 2B). Using increasing concentrations of CHX treatment in MCF7 and HCT116 taspase1 WT and KO cells, MLL1 protein levels were significantly more stable in taspase1 KO cells than in the counterpart in WT cells (FIG. 2C-F). Collectively, our results demonstrate that the proteolytic cleavage of MLL1 by taspase1 primed the MLL1 protein to the degradation pathways (FIG. 2 and data not shown), without affecting the cellular localization of MLL1 (FIGS. 1F and 1G).

Figure 3:
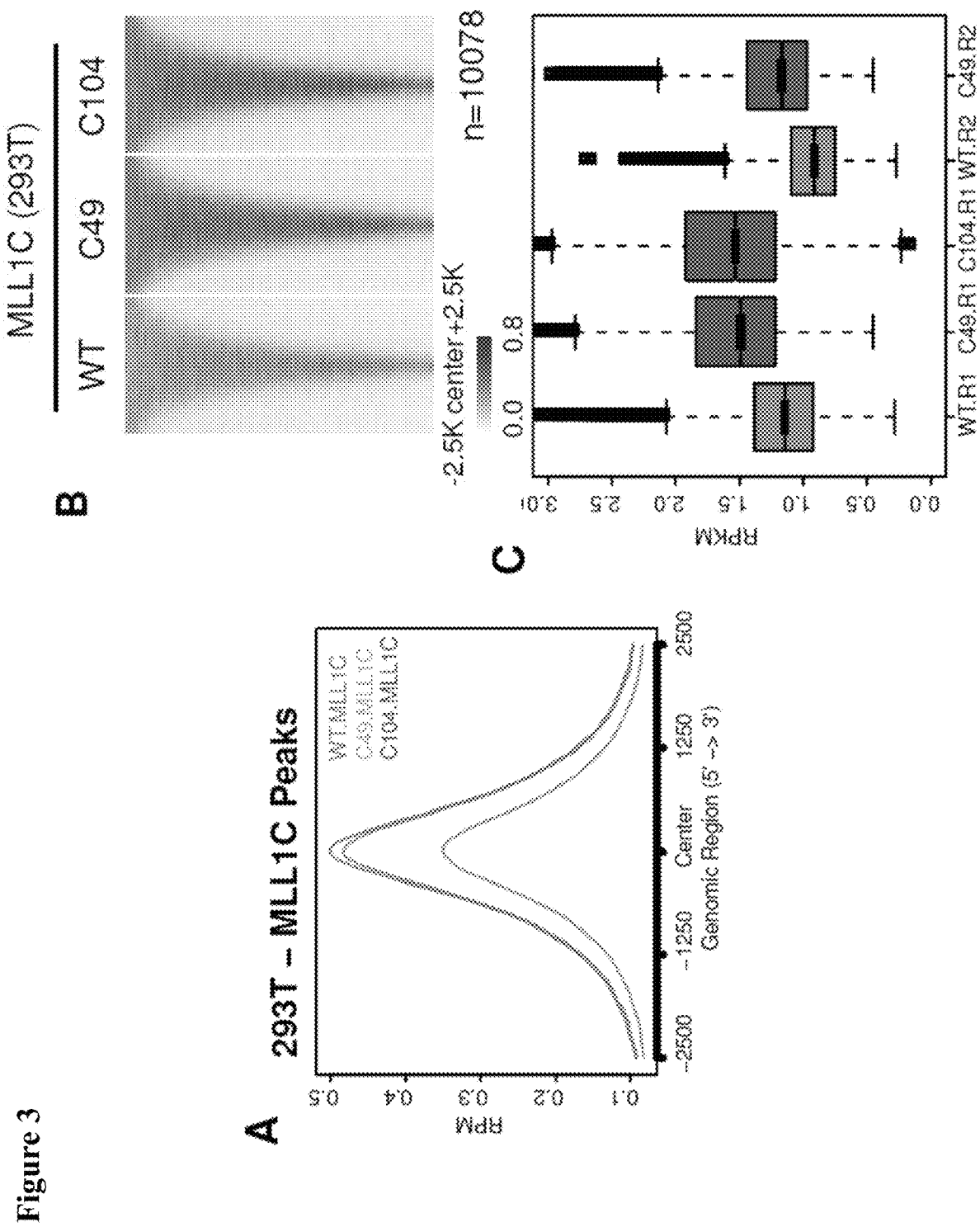
FIG. 3. MLL1 chromatin binding is increased in taspase1 KO cells. Coverage profiles, heatmaps and box plots of MLL1C (A)-(C), MLL1N (D)-(F) and MLL2C (G)-(I) in 293T cells, and MLL1C (J)-(L) and MLL1N (M)-(O) in MCF7 cells are shown. A region within 2.5 kb around the center of MLL1C, MLL1N or MLL2C is displayed. For the heatmaps, profiles are centered within 2.5 kb of MLL1 or MLL2 occupied peaks and sorted in descending order of MLL1C, MLL1N or MLL2C occupancy in WT cells. Box plots quantitation of the MLL1 occupancy in 293T cells is shown in replicates.
Figure 3:
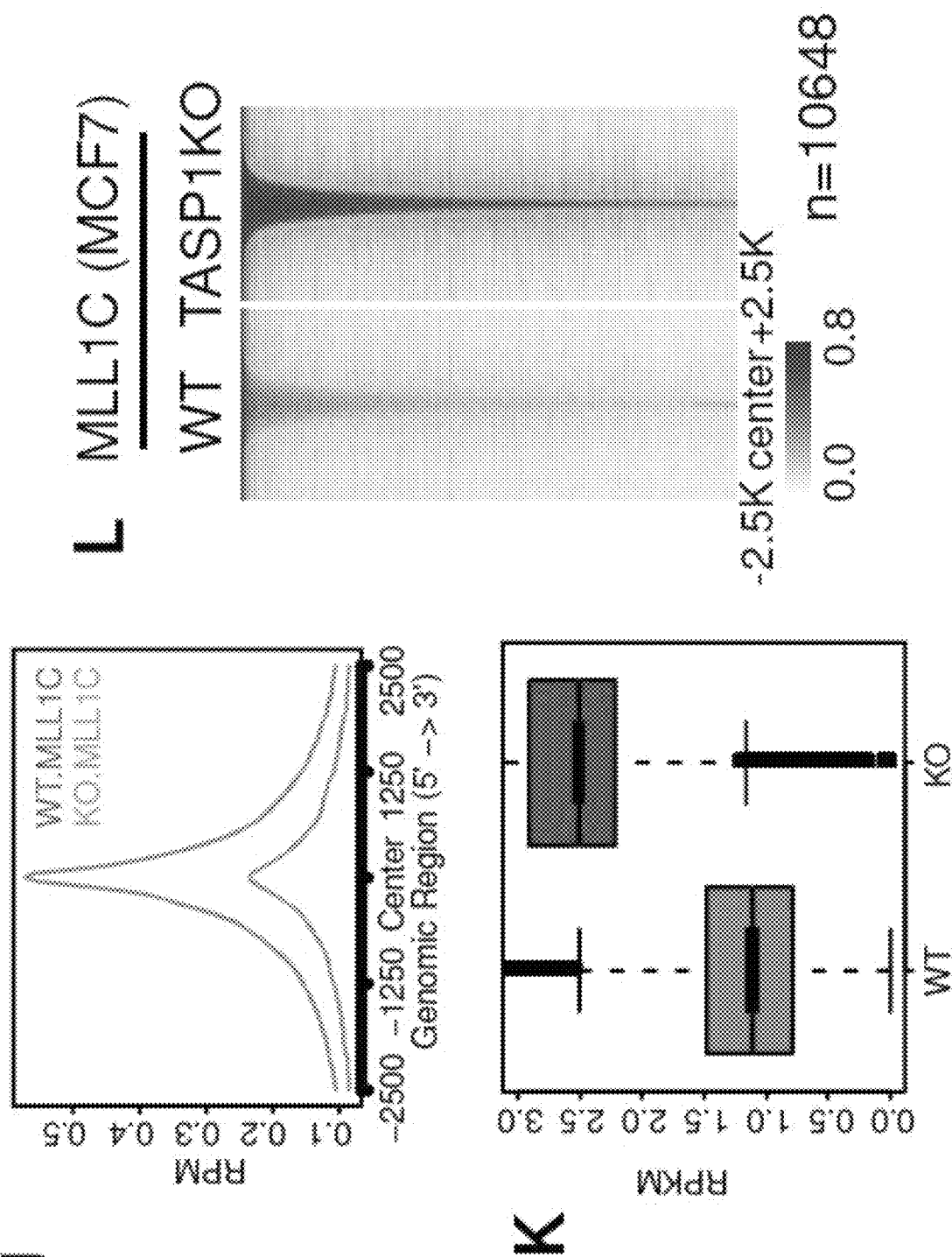
Figure 3:
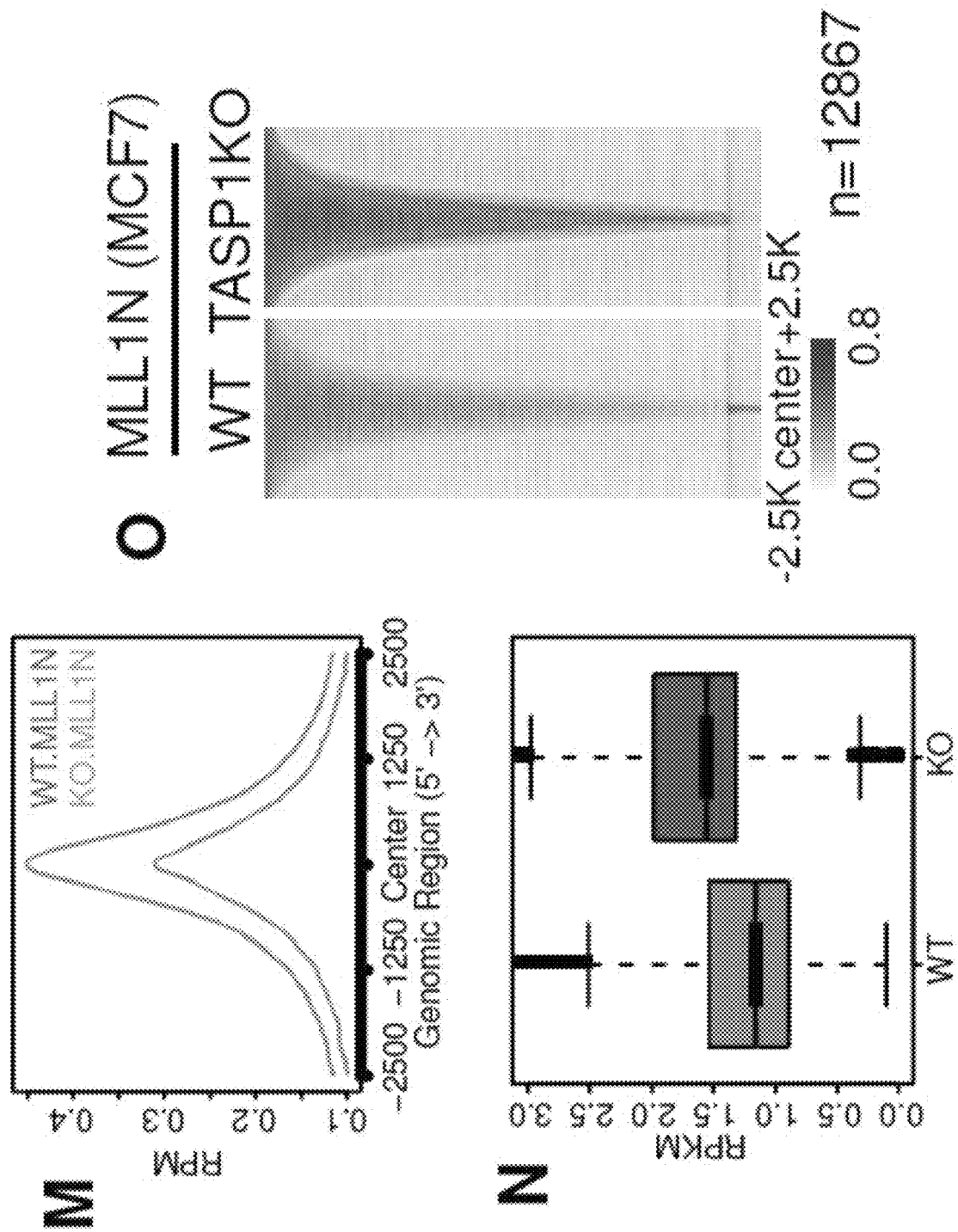

Increased chromatin association of stabilized full-length MLL1 in taspase1 KO cells. To differentiate the functional outcome between the cleaved MLL1 and its un-cleaved version in taspase1 KO cells, we performed chromatin immunoprecipitation followed by the sequencing (ChIP-seq) using MLL1 N-terminal and C-terminal antibodies as well as MLL2 C-terminal antibody (FIG. 3, FIG. 10, and data not shown). We first confirmed the specificity of MLL1N and MLL1C antibodies for ChIP-seq by knocking down MLL1 in 293T cells (FIG. 10A) and track example of the complete chromosome 1 (Chr1) shows that the majority of MLL1 peaks are lost as the result of MLL1 KO (data not shown). To quantitatively measure the binding affinity of MLL1 on the chromatin in taspase1 WT and KO cells, the occupancy of cleaved and un-cleaved MLL1 were compared (FIG. 3 and data not shown). Both MLL1C and MLL1N intensities were increased in taspase1 KO cells (FIG. 3A-3F), while MLL2 chromatin association was not altered in taspase1 KO cells (FIG. 3G-3I), suggesting that the loss taspase1 resulted in an increased MLL1 chromatin association. Similarly, we observed the increase in MLL1 chromatin occupancy in MCF7 taspase1 KO cells (FIG. 3J-3O), which generalized the common mechanism that leads to the MLL1 chromatin interaction as the result of taspase1 KO. Track examples of ZMYND11, NEK1, CLCN3 and CASCS genes demonstrate the increase in MLL1 peak height in taspase1 KO cells (data not shown). Together, these data suggest that there is less MLL1 protein turnover on chromatin in the absence of taspase1.

Figure 11:
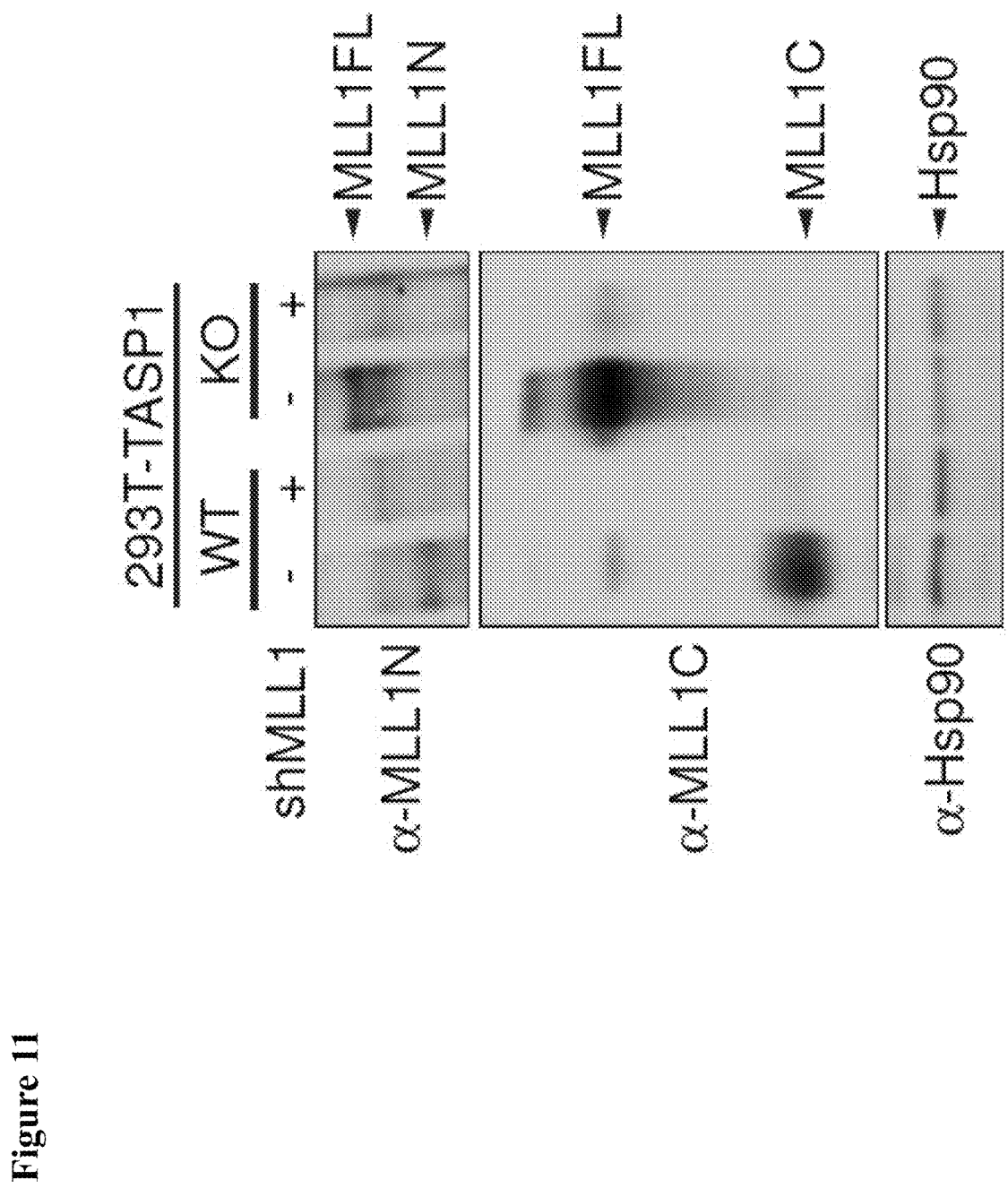
FIG. 11. MLL1 is knocked down in 293T taspase1 WT and KO cells. Western blot shows the knockdown efficiency by blotting against MLL1C and MLL1N antibodies.

Stabilize MLL1 in taspase1 null cells displaces MLL-chimera on chromatin. To directly dissect the gene expression signature controlled by taspase1 and by cleaved MLL1 and full-length MLL1 in taspase1 WT and KO cells, we performed RNA-seq studies in taspase1 WT and KO with MLL1 knockdown (FIG. 11 and data not shown). When taspase1 was lost in 293T cells, the expression of 457 genes was upregulated and 366 genes were downregulated (data not shown). Among the downregulated genes, the gene ontology analyses demonstrated the enrichment in ncRNA processing, cellular response to stress, DNA damage and chromatin assembly pathways (data not shown). Conversely, the genes that were upregulated with taspase1 loss were involved in cellular component movement, extracellular matrix organization and regulation of cell adhesion (data not shown). When we analyzed the MLL1 target gene expression changes in taspase1 WT and KO cells (FIG. 11), the genome-wide analysis revealed subtle difference in the gene expression signature shown in the MA plot (data not shown), suggesting that the uncleaved MLL1 in taspase1 KO cells retained the functionality and activity in terms of the global gene expression pattern. MLL1 has been shown to be involved in histone H3K4 methylation (Wang et al. 2009; Piunti and Shilatifard 2016; Rickels et al. 2016). Therefore, it would be interesting to determine whether the uncleaved MLL1 alters the H3K4 methylation pattern and the nearby gene expression. However, we noticed that histone H3K4 methylation levels were not significantly changed at the regions where MLL1 binding was increased (data not shown). The data was consistent with our recently published study where we showed that the increased association of MLL1 on chromatin by pharmacologically inhibiting IRAK4 did not alter the H3K4 methylation levels occupied by MLL1 at the same regions (Liang et al. 2017).

MLL fusion proteins exert oncogenic functions in leukemia cells through the involvement of the Super Elongation Complex (SEC) to induce the rapid transcription of oncogenes driving leukemogenesis (Smith et al. 2011; Luo et al. 2012). We postulated that the increased association of wild type MLL1 (uncleaved form) in the absence of taspase1 cleavage might prevent the recruitment of SEC by MLL-chimeras. To answer this question, taspase1 WT and KO 293T cells were transfected with MLL-AF4 fusion proteins. Eleven-nineteen lysine-rich leukemia (ELL) proteins ELL2 is a subunit of SEC (Shilatifard et al. 1997; Smith et al. 2011; Luo et al. 2012), and its occupancy in taspase1 WT and KO 293T cells was examined by ChIP-seq experiments. About 867 genomic regions demonstrated significant decrease in binding of ELL2 subunit of SEC in taspase1 KO cells compared to that in the WT cells (FIG. 4A). As postulated, these regions were bound by elevated levels of uncleaved MLL1 proteins (FIG. 4B). Track examples of the promoter regions of C6orf211, KBTBD4, NDUFS3, ELF2 and PDE7A genes clearly demonstrated that the exclusion of ELL2 in the presence of MLL-AF4 fusion proteins was due to the preferential binding of non-cleavable MLL1 at the same region (data not shown). As our internal control, Flag-MLLAF4 transfected equally as shown by the peak intensities in different samples (data not shown). Collectively, our data suggest that uncleaved MLL1 in the absence of taspase1 can displace MLL-chimera occupancy suggesting this pathway as a possible new therapeutic approach for the treatment of MLL1 translocation based childhood leukemia.

Figure 12:
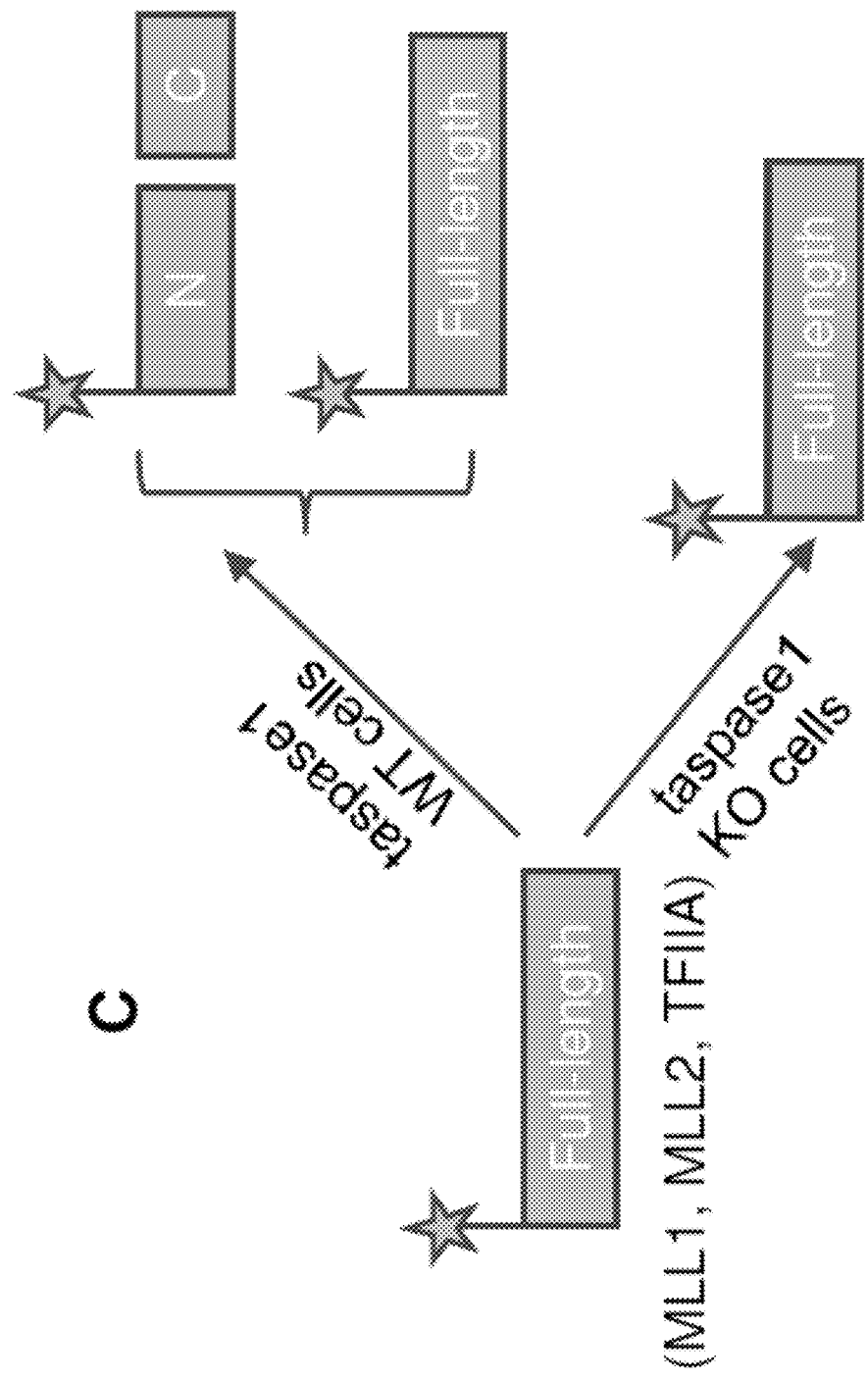
FIG. 12. Generation of reporter constructs harboring taspase1 cleavage sites. (A) Taspase1 was knocked down in MCF7 cells with shRNA. Full-length and cleaved MLL1 and MLL2 protein levels were shown by western blot. (B) mRNA level of taspase1 was measured by QPCR. (C) Flag-tagged reporter constructs overexpression in taspase1 WT and KO cells, which resulted in either cleavage or non-cleavage. (D) 3× Flag-MLL1-p75, (E) 3× Flag-MLL2-p69, and (F) 3× Flag-TFIIA reporter constructs harboring taspase1 cleavage sites were cloned and expressed in taspase1 WT and KO cells to test the cleavage efficiency.
Figure 12:
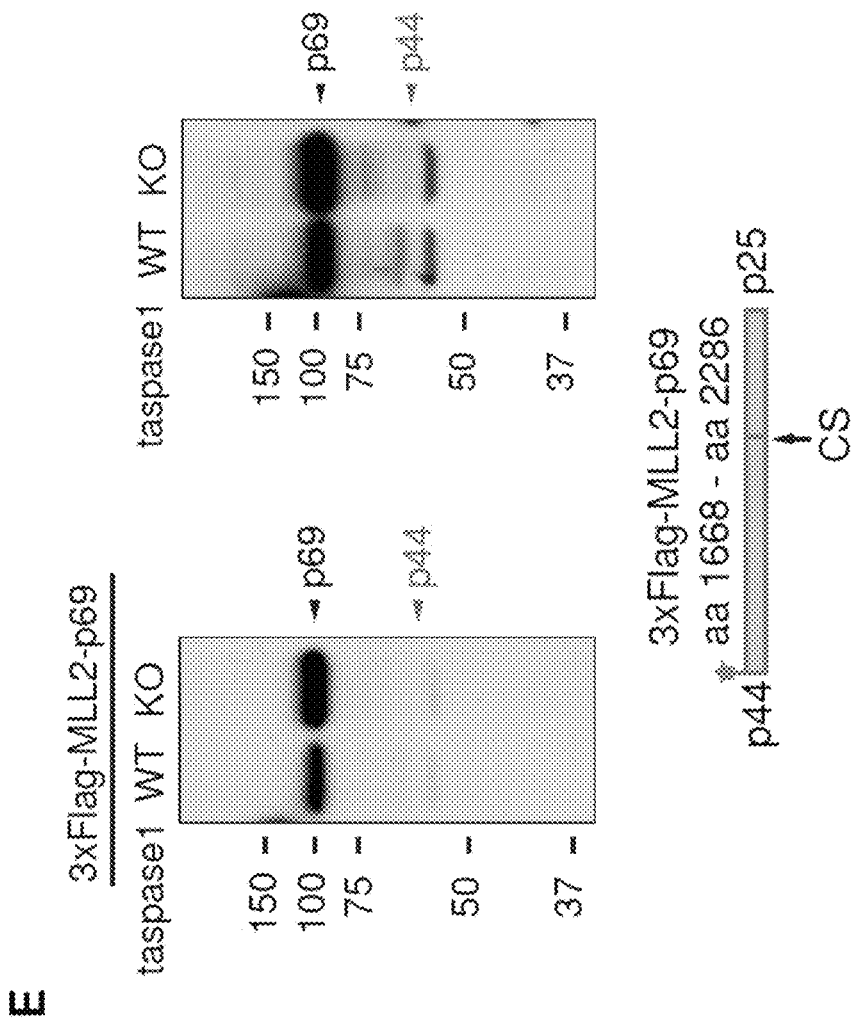
Figure 12:
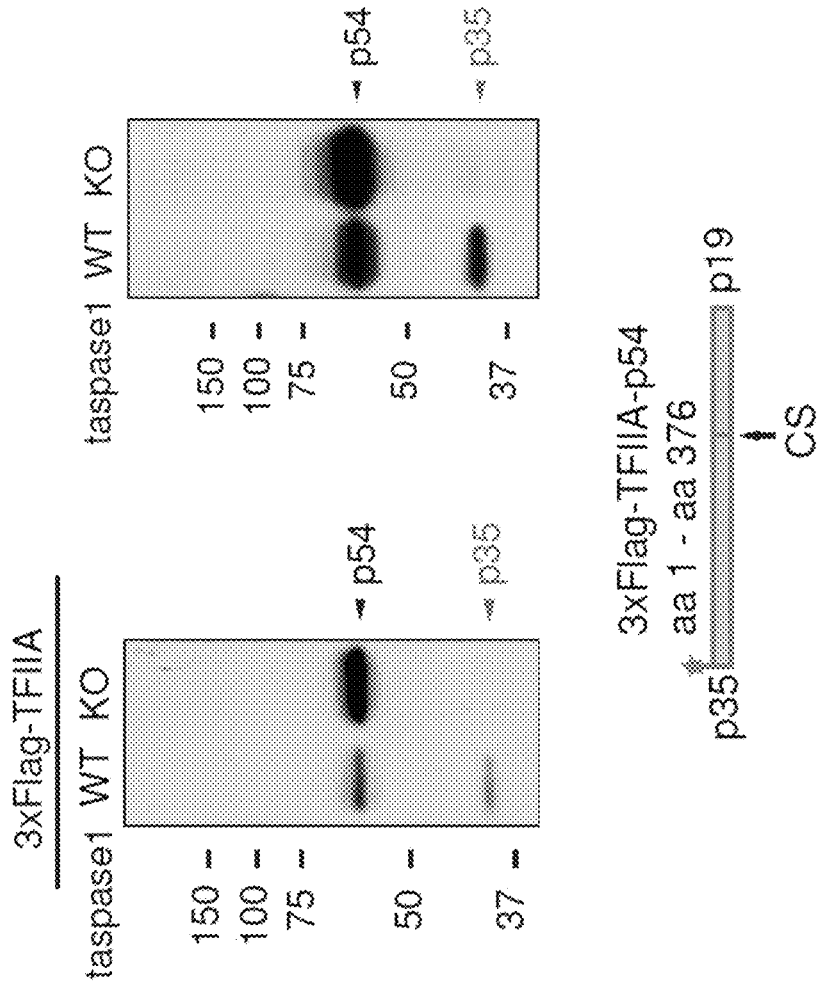

Phosphorylation of MLL1 in a CKII-dependent manner selectively increase full-length MLL1 protein levels. We envisioned two independent approaches to interfere with MLL1 cleavage by taspase1: 1) pharmacological inhibition of taspase1, resulting in the inactivation of taspase1 and non-cleavage of its substrates (MLL1, MLL2 and TFIIA etc.); 2) modulation of the cleavage efficiency by targeting MLL1 itself without affecting the activity of taspase1 and other substrates. With the availability of the crystal structure of taspase1 (Khan et al. 2005) and our taspase1 knockout cells, we took the advantages in identifying small molecule inhibitors against taspase1 to treat cancer patients with taspase1 overexpression. Therefore, we launched a virtual screening for taspase1 small molecule inhibitors using the crystal structure of taspase1 (Khan et al. 2005). Unfortunately, out of the initial 26 lead compounds, no single compound could block the taspase1 activity in vitro or in vivo (data not shown). Previous efforts in identifying specific taspase1 inhibitors demonstrated limited success as well. First, the proteolytic activity of taspase1 could not be diminished by the common protease inhibitors (Hsieh et al. 2003a; Hsieh et al. 2003b). Second, cell-based taspase1 translocation assays have been established by different groups (Bier et al. 2011b; Chen et al. 2012), but compounds with potent in vivo inhibition efficacy have not been identified so far (Stauber et al. 2012; Wunsch et al. 2012; Wunsch et al. 2016). Our results agreed with previous studies in screening taspase1 inhibitors but with no success, probably due to the unique structure and the extreme potency of this particular protease. Indeed, we noticed that knocking down taspase1 by 70% was not sufficient to rescue the cleavage of MLL1 and MLL2 in MCF7 cells (FIGS. 12A and 12B) suggesting that taspase1 inhibition perhaps is not a good approach for regulating MLL1 cleavage.

Figure 13:
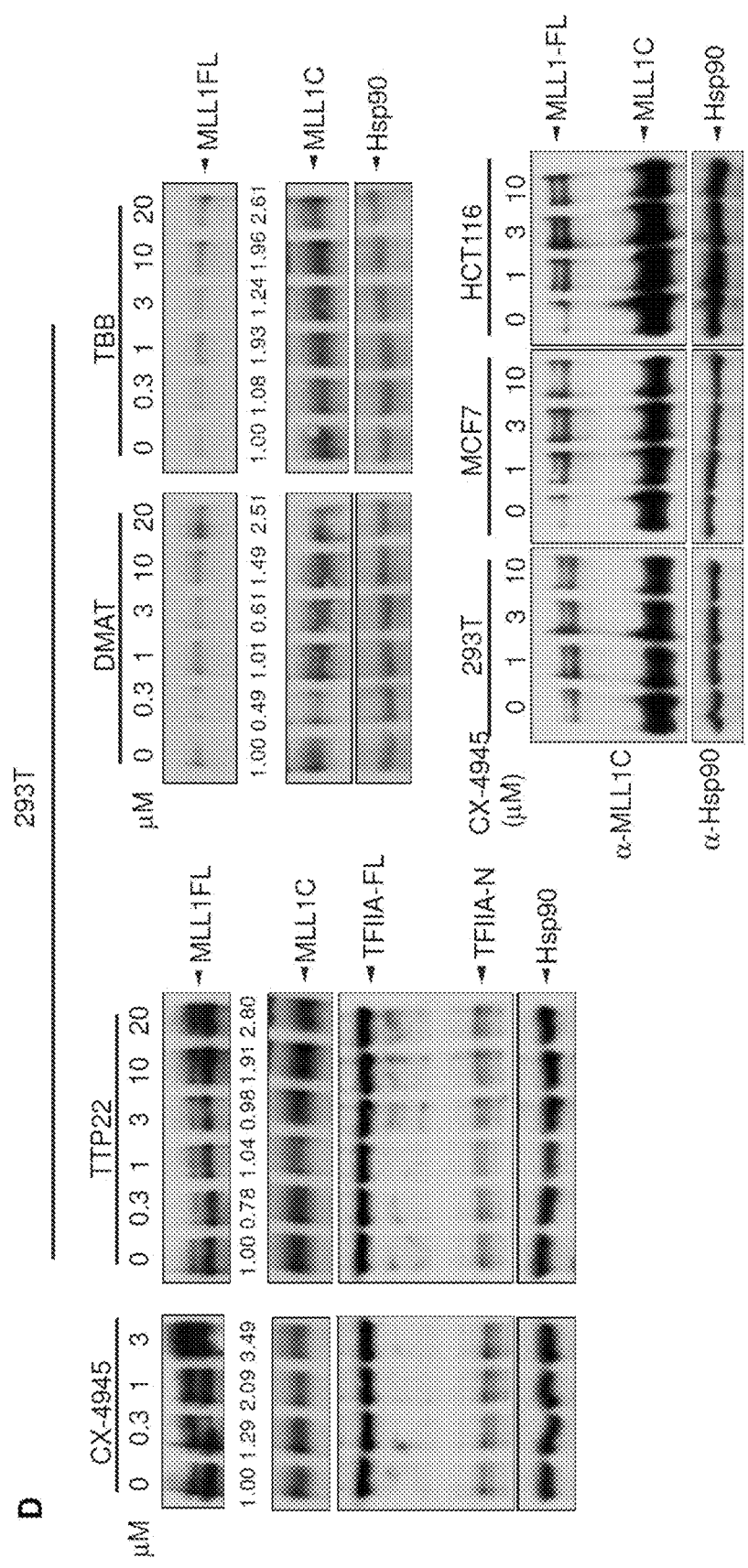
FIG. 13. CKII inhibitors increase full-length MLL1 protein levels. (A) Prediction of kinases that phosphorylate MLL1 near the taspase1 cleavage site. (B) Structure of the CKII inhibitors CX-4945, TTP22, DMAT and TTB. (C) Comparison of the $IC_{50}$ and molecular weight of the four CKII inhibitors. (D) CKII inhibitors (0-20 µM) were used to treat 293T, MCF7 and HCT116 cells and dose-dependent increase of full-length MLL1 protein levels was revealed by Western Blot using MLL1C antibody. Quantification of the band intensities was performed by ImageJ software. (E) and (F) in vitro taspase1 cleavage assay. Taspase1 KO cell lysates were incubated with recombinant his-tagged taspase1 (0, 1, 10, 100 or 1000 ng) and subject to in vitro taspase1 cleavage assay. Cleavage efficiency was shown as the blotting for MLL1 and TFIIA using Hsp90 as the loading control.
Figure 13:
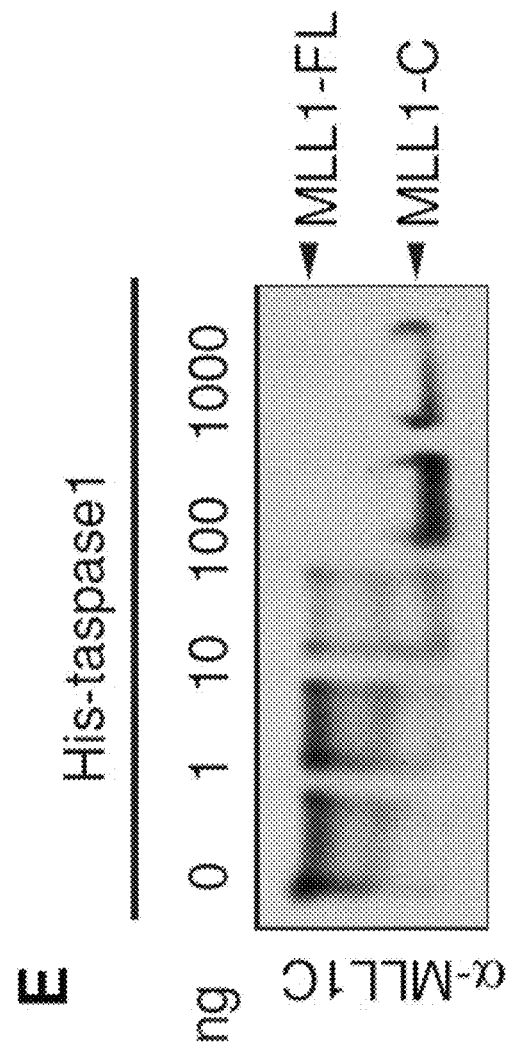
Figure 13:
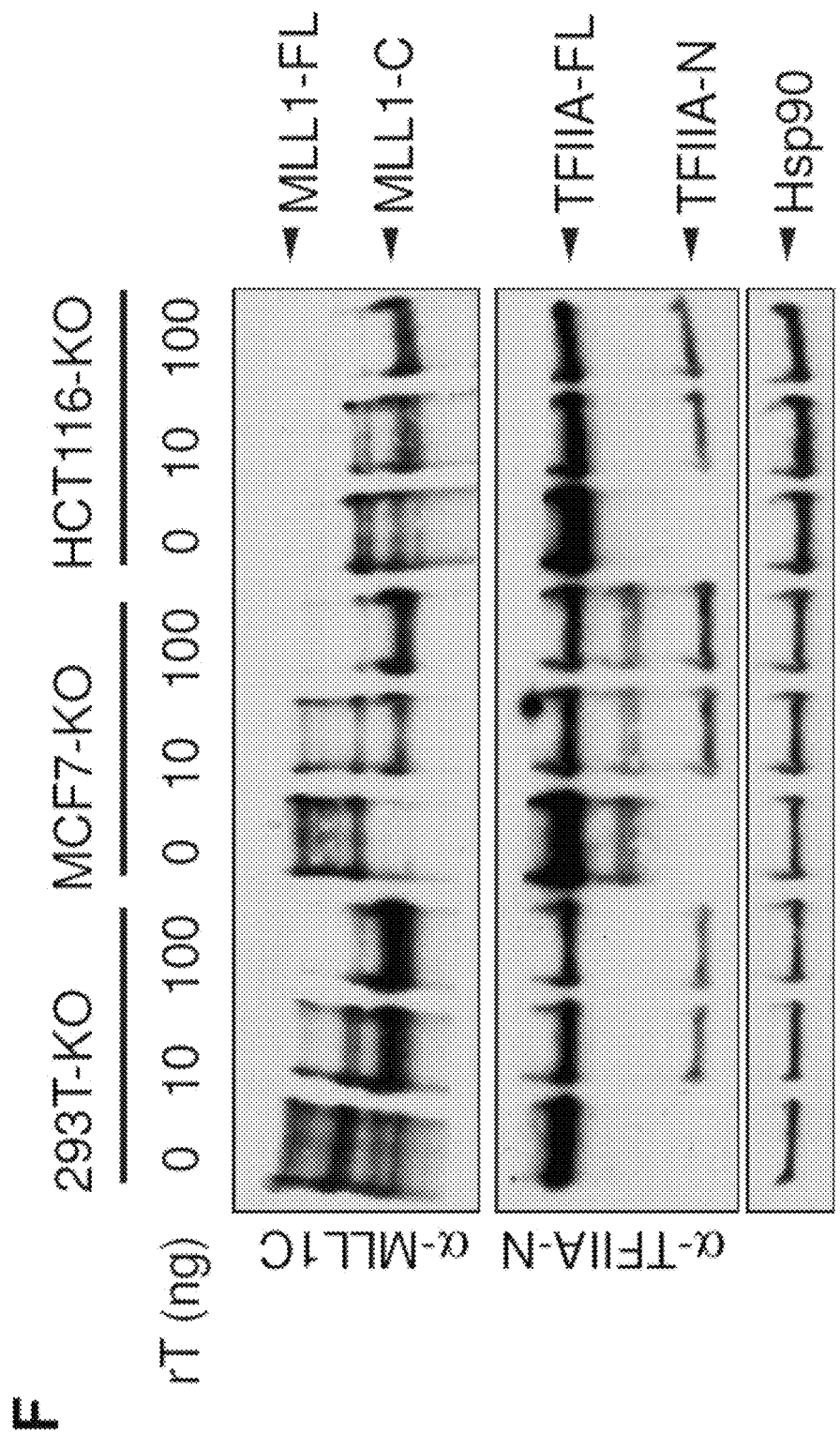

This leads us to our second approach of targeting the downstream protease substrate rather than taspase1 itself. For this purpose, we generated several reporters including 3× Flag tagged MLL1-p75, MLL2-p69 and full-length TFIIA harboring the taspase1 cleavage sites, and expressed them in taspase1 WT and KO cells in order to test the cleavage efficiency (FIG. 12C-F). Interestingly, we found several serine and threonine residues near the taspase1 cleavage sites were phosphorylated based on the PhosphoSitePlus database (Hornbeck et al. 2015) (FIG. 5A). When the phosphorylation sites on the reporter constructs were mutated to alanine (AA), cleavage efficiency was dramatically diminished, while the phosphor-mimetic mutation to aspartate (DD) was comparably cleaved as the WT reporters for both MLL1 and TFIIA (FIGS. 5B and 5C). Further, when the WT or AA reporters were co-expressed with HA tagged taspase1, the AA reporter was relatively more resistant to the cleavage as shown by the MLL1-p75 and TFIIA-p54 bands (FIGS. 5D and 5E). To predict what kinases may phosphorylate MLL1 on the serine and threonine near the cleavage sites, we used the NetPhosK 1.0 Server and the top one predicted kinase was CKII based on the score of the prediction confidence and the similarity to one or more of the phosphorylation sites used in training the method (Blom et al. 2004) (FIG. 13A). The general consensus recognition motif for phosphorylation by CKII is pSXXE/D, pSXE/D, pSE/D, pS/pTD/EXD/E, and variations of these sequences (Meggio et al. 1994; Sarno et al. 1996; Rush et al. 2005). T2724 and S2726 of MLL1 fall within the consensus sequence recognized CKII (FIG. 5B). Therefore, we first knocked down the catalytic subunits of CKII and examined the MLL1 cleavage in 293T cells. We observed a consistent increase of MLL1 full-length protein levels with either CKIIα or CKIIα' knockdown (FIG. 5F). Next, we tested four CKII inhibitors including CX-4945, TTP22, DMAT and TTB with differential $IC_{50}$ values (FIGS. 13B and 13C). Treatment of CX-4945 and TTP22 demonstrated dose-dependent increase of MLL1 full-length protein levels in our cell-based assays (FIG. 13D) and were selected for further validation. We also established the in vitro taspase1 cleavage assay using taspase1 KO cell lysates and his-tagged taspase1 recombinant proteins (FIGS. 13E and 13F). CX-4945 treatment increased the conversion from cleaved MLL1 to full-length MLL1 without affecting the cleavage of MLL2 or TFIIA in vivo (FIG. 5G). Finally, when taspase1 KO cells were pretreated with CX-4945 or TTP22 and lysed for in vitro taspase1 cleavage assay, cleavage efficiency was significantly diminished compared with DMSO control by the recombinant taspase1 protein (FIG. 5H-I). Overall, our data revealed that CKII inhibition selectively increased the full-length MLL1 protein levels by decreasing the phosphorylation of MLL1 near its taspase1 cleavage site.

CKII inhibition increases genome-wide MLL1 occupancy and displaces MLL-chimera from chromatin. Similar to taspase1 loss, CKII inhibitors CX-4945 and TTP22 treatment resulted in the global increase of MLL1 occupancy in 293T cells (FIG. 6A-D). Since MLL-chimeras association with chromatin drives leukemogenesis, we treated a panel of leukemic cell lines (with or without MLL fusion protein expression) with increasing concentrations of CX-4945. MLL leukemia cells were generally more sensitive than non-MLL leukemic cells, suggesting a preferential killing by CX-4945 through increasing the MLL full length protein stability (FIG. 6D). When we treated SEM leukemia cells (bearing MLL-AFF1/AF4 fusion) with CX-4945, MLL1-FL protein levels also increased without altering MLL-AF4 protein levels (FIG. 6E). The genome-wide binding of MLL-AFF1, AFF4 and ELL2 recruitment were decrease upon treatment with CX-4945 (FIG. 6F), suggesting that CKII inhibition resulted in the increase of genome-wide MLL1 occupancy and displacement of MLL-chimera from chromatin in the leukemic cells, as tested by SEC subunits ChIP-seq. The decrease of MLL1-AFF1, AFF4 and ELL2 binding at the promoter regions of JUP and SLC43A2 genes (FIG. 6G-H) were also accompanied by the decrease of mRNA levels of these genes (FIG. 6I-J).

Figure 14:
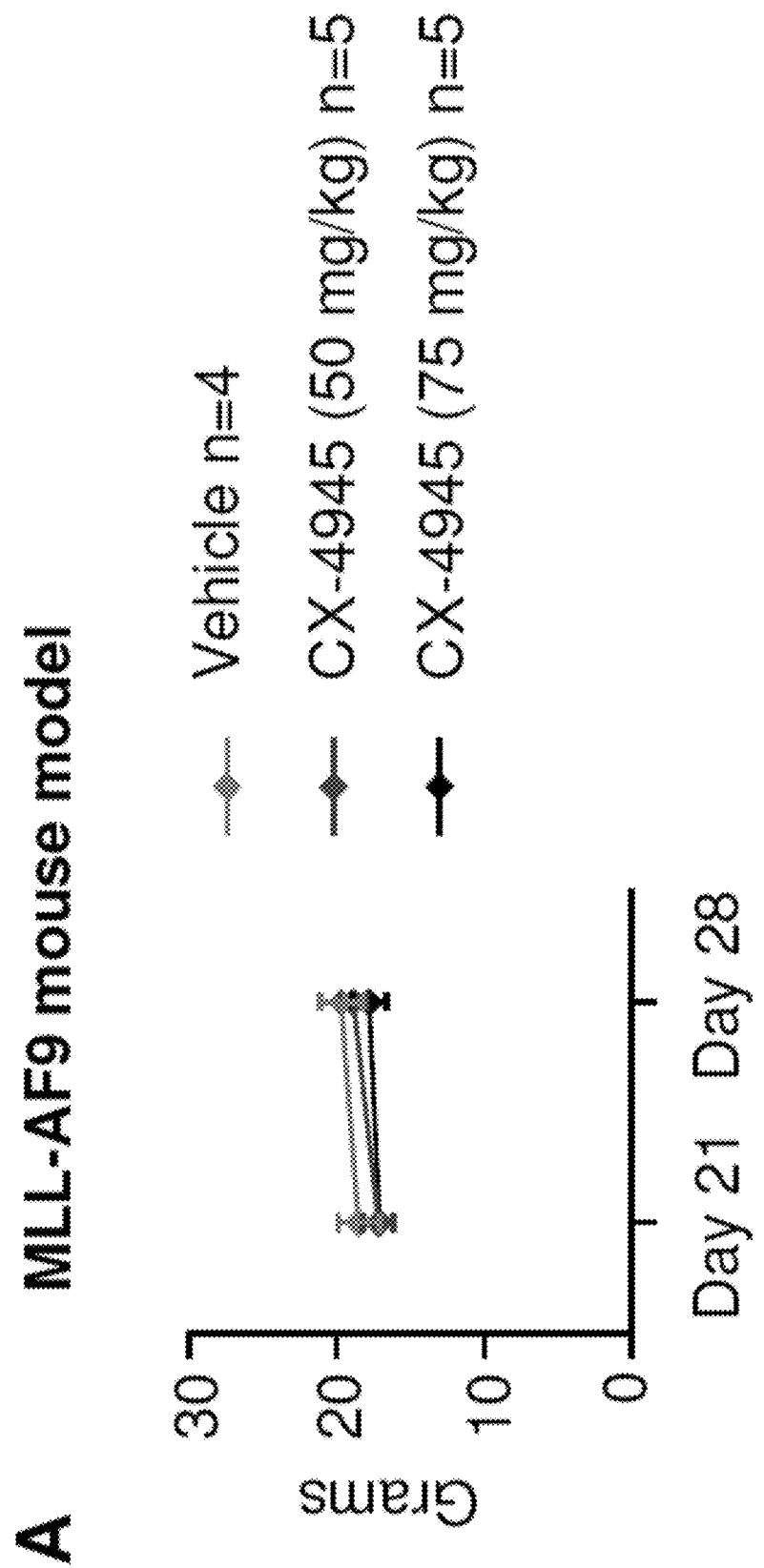
FIG. 14. CX-4945 treatment did not affect the weight of the mice. The weight of the mice is shown in (A) MLL-AF9 syngeneic mouse model, (B) MOLM13 human leukemia xenograft mouse model.
Figure 14:
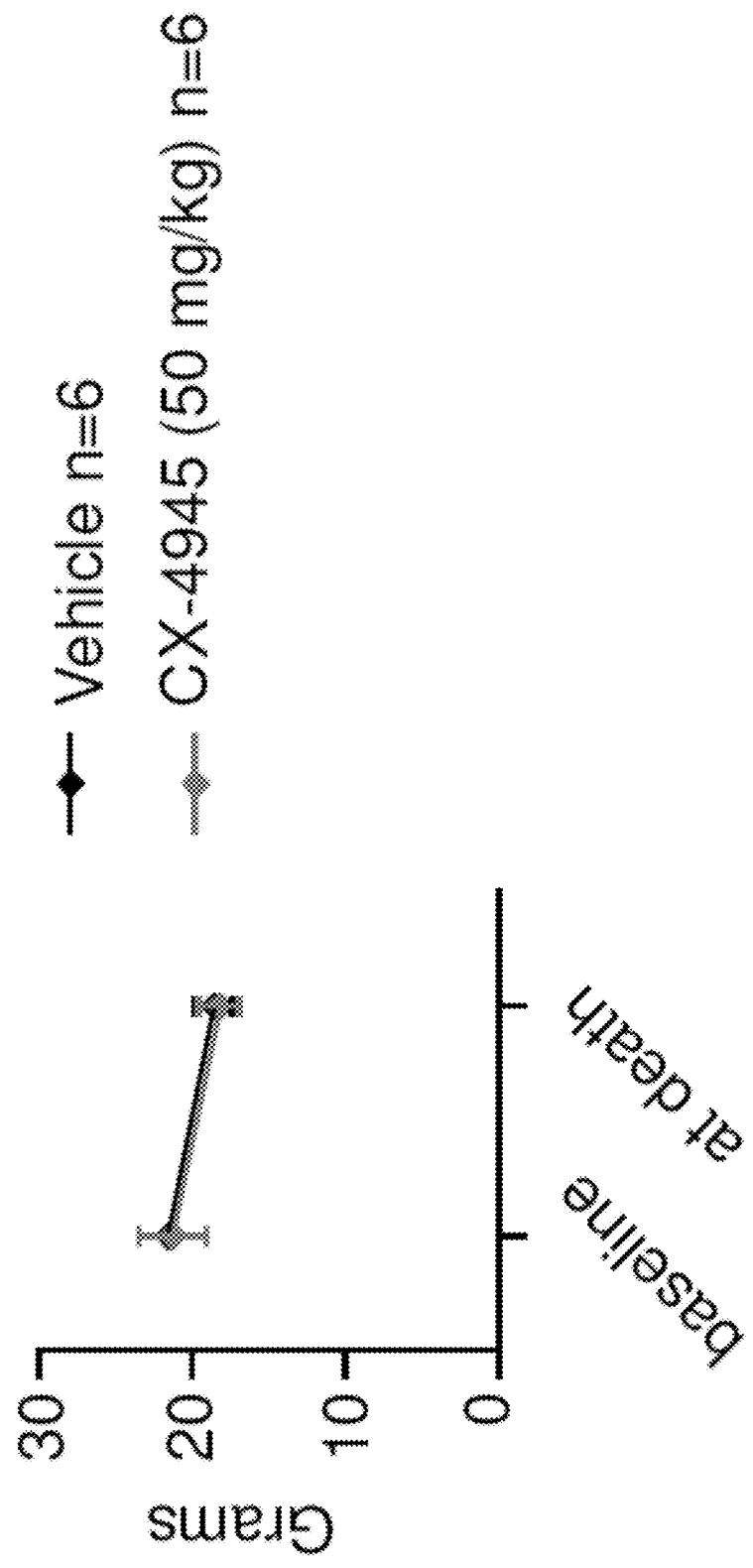

CKII inhibition delays the leukemia progression and improves survival of MLL-AF9 mice and NSGS mice transplanted with MOLM13 leukemia cells. To further examine the effect of CKII inhibition on leukemia progression in vivo, we studied the efficacy of CX-4945 in two independent mouse models—MLL-AF9 syngeneic mouse model and MOLM13 human leukemia xenograft mouse model. First, we treated MLL-AF9 mice with CX-4945 via oral gavage for ten days and monitored the survival of these mice (FIG. 7A). CKII inhibition by CX-4945 significantly delayed the leukemia progression and improved the survival of MLL-AF9 mice (FIG. 7B). In the second model, NSGS mice were transplanted with human MOLM13 cells for five days before CX-4945 delivery via oral gavage for ten days (FIG. 7C). Development of the leukemia was monitored by flow cytometry, H&E staining and histological analysis. Leukemia free survival of the mice treated with CX-4945 was also significantly lengthened (FIG. 7D). In both models, CX-4945 treatment did not affect the weight of the mice compared with the vehicle control group (FIG. 14). Therefore, our data suggest that MLL1 cleavage by taspase1 primed the protein to degradation pathway. In the absence of taspase1 cleavage, MLL1 protein is relatively more stable and preferentially associated with chromatin. CKII phosphorylation on MLL1 near the cleavage sites facilitates the cleavage event. Stabilization of the full-length MLL1 is achieved by pharmacological inhibition of CKII phosphorylation on MLL1. The stabilized MLL1 protein excludes the MLL translocation partners and SEC involvement in aggressive leukemic cells, suggesting a new therapeutic approach for the treatment of MLL-translocation based leukemia (FIG. 7E).

Discussion

Figure 6:
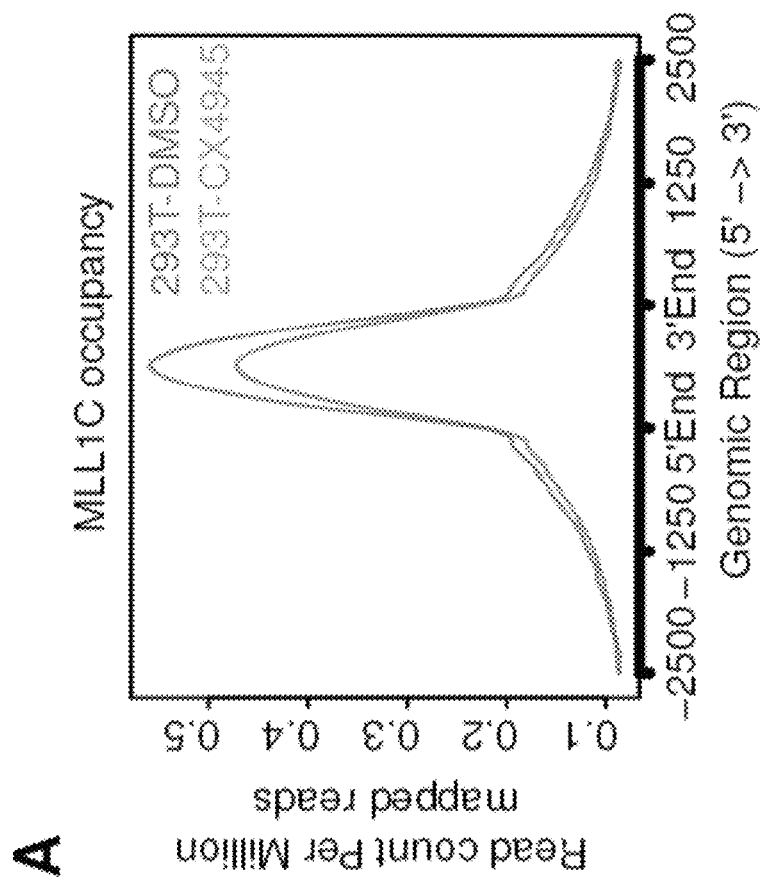
FIG. 6. CKII inhibition increases genome-wide MLL occupancy and excludes SEC recruitment in MLL leukemia cells. (A) and (B) MLL1C occupancy in CX-4945 or TTP22 treated cells were shown relative to DMSO control. A region within 2.5 kb around the center of MLL1C is displayed. (C) Track examples of the MLL1 occupancy at the promoter regions of ELF2 and C6orf211. (D) CX-4945 inhibition of leukemia cell proliferation. Multiple MLL leukemia (orange lines) and non-MLL leukemia (blue lines) were cultured with different doses of CX-4945 for 3 days. Cell number was determined by cell counter and normalized to DMSO control. (E) SEM cells were treated with 0, 5 or 10 µM of CX-4945 for 30 hours and western blot was performed to determine the MLL1 full-length protein levels and MLL-AF4 fusion protein levels. (F) MLL-AFF1, AFF4 and ELL2 occupancies were decreased by CX-4945 treatment in SEM cells. A region within 2.5 kb around the center of MLL-AFF1, AFF4 and ELL2 is displayed.
Figure 6:
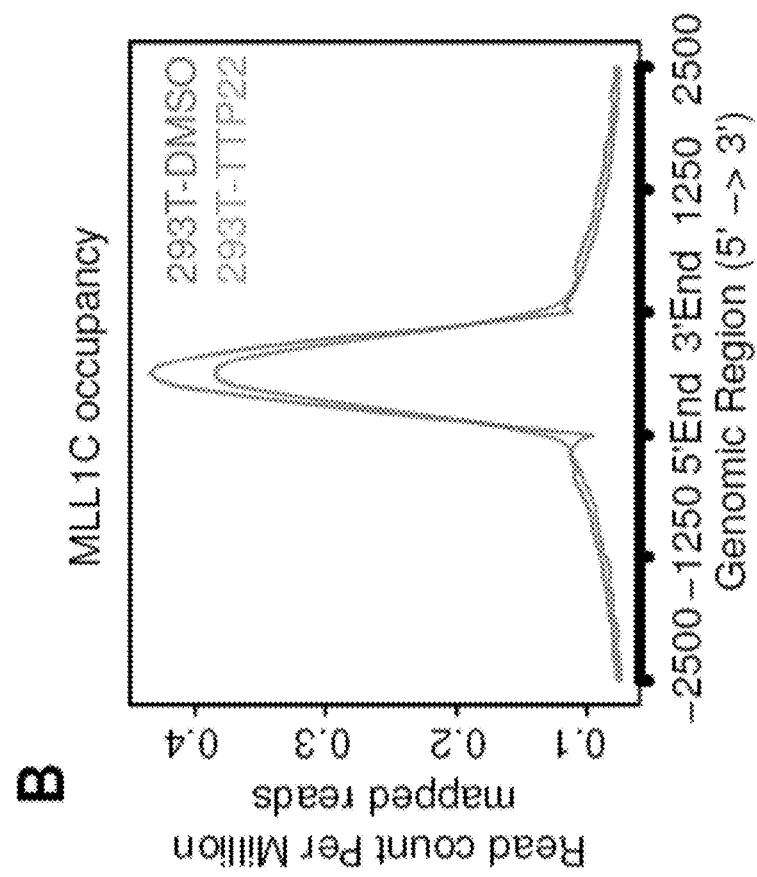
Figure 6:
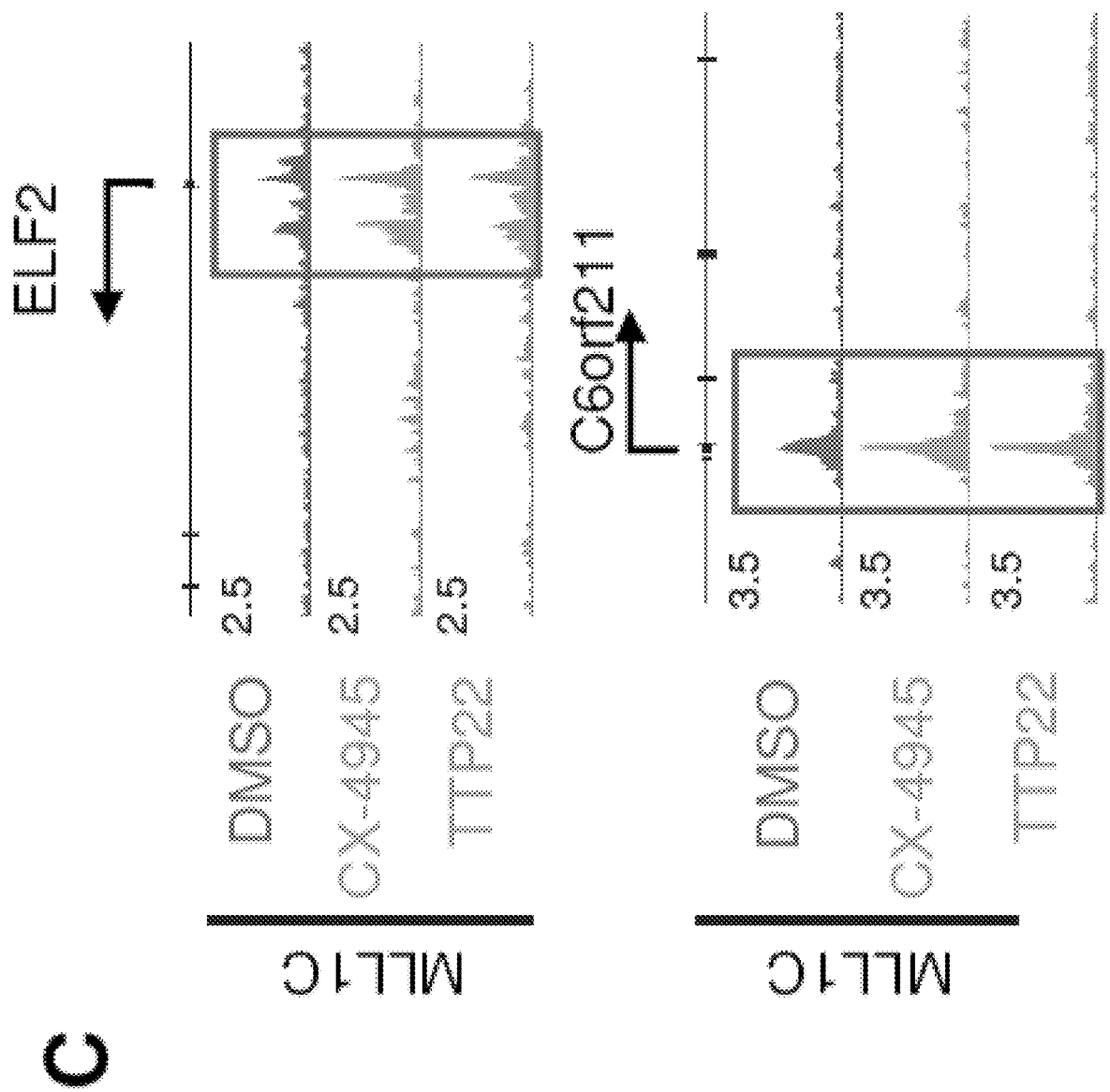
Figure 6:
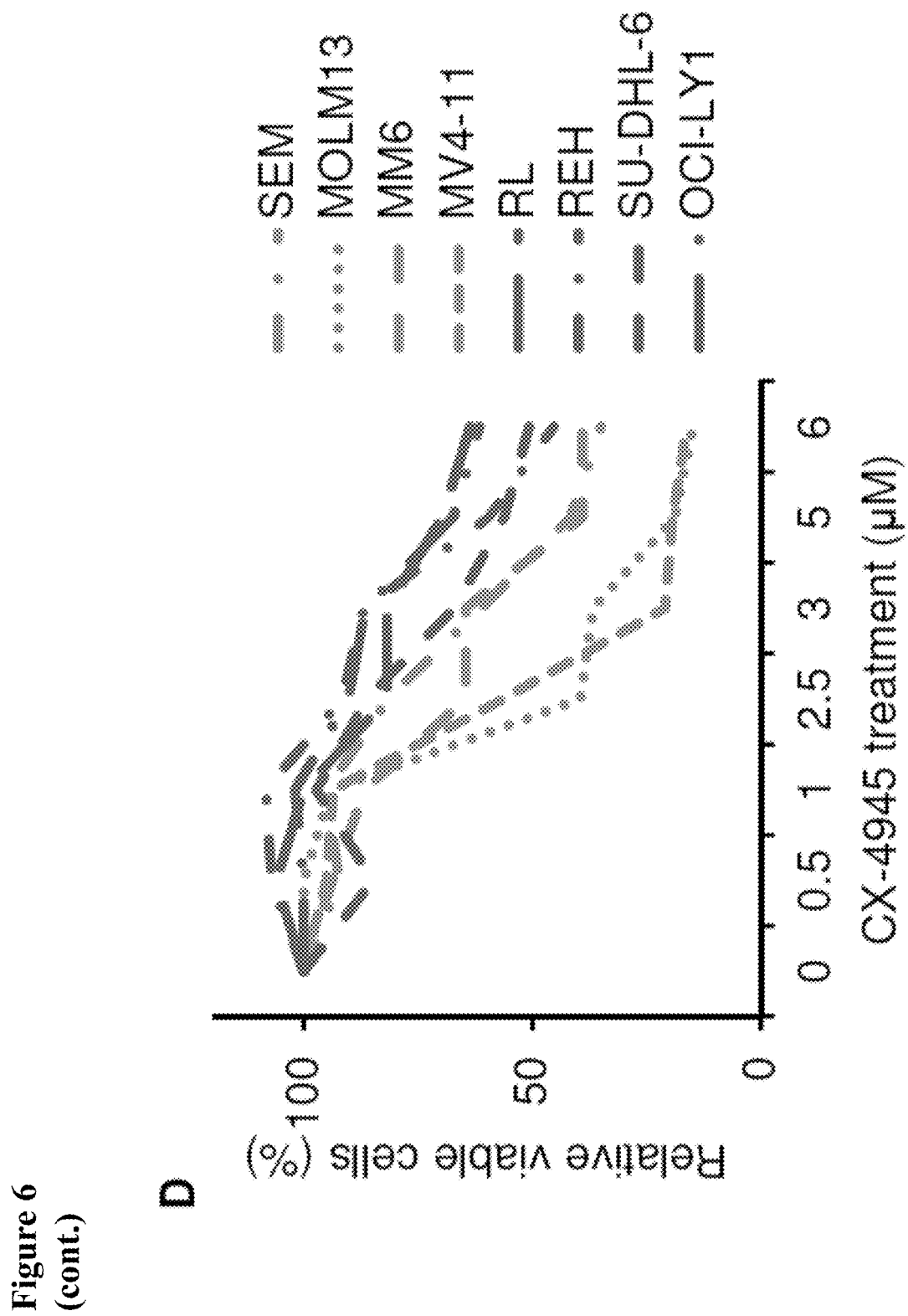
Figure 6:
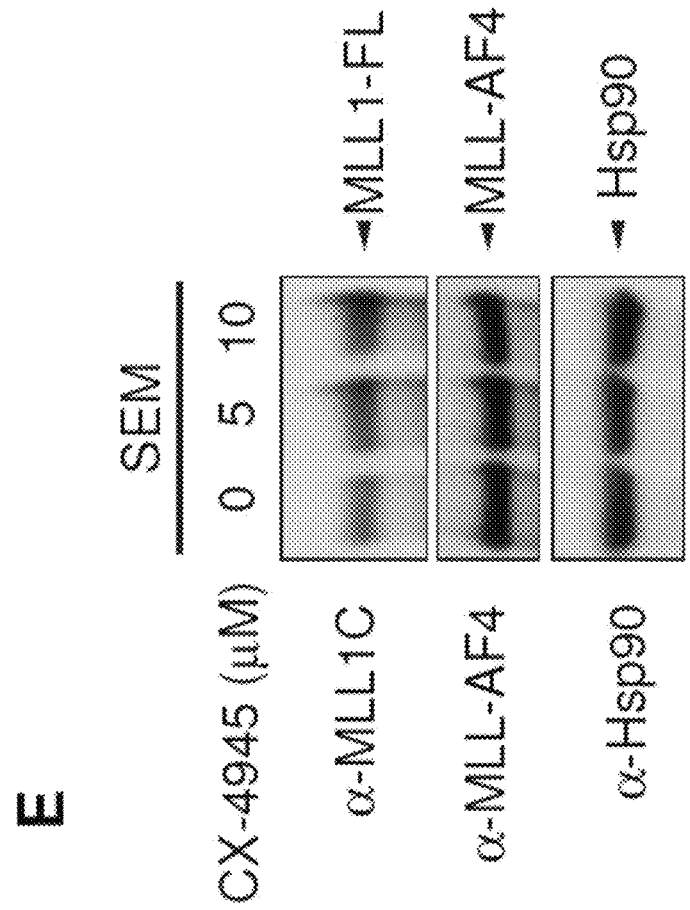
Figure 6:
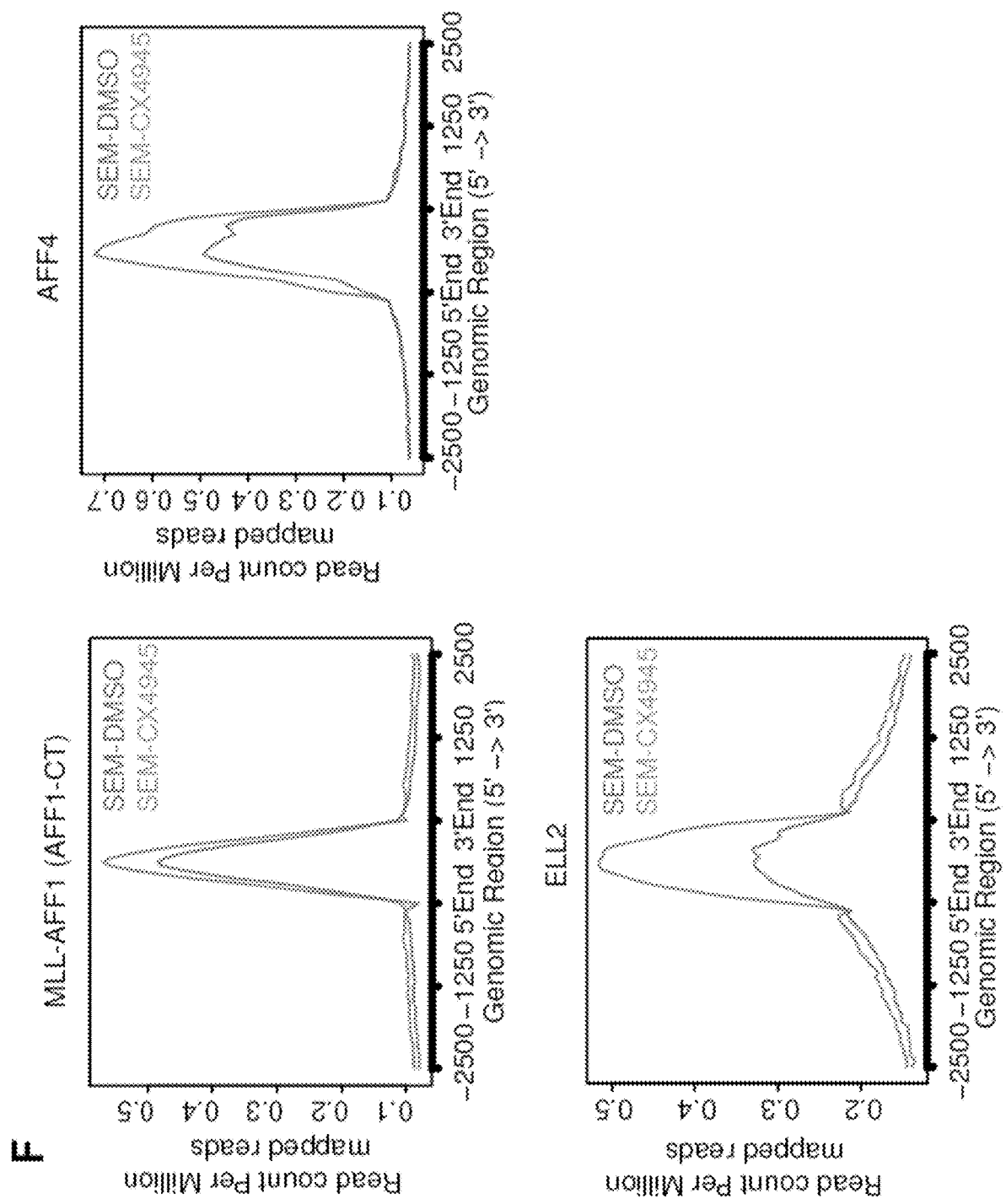
Figure 7:
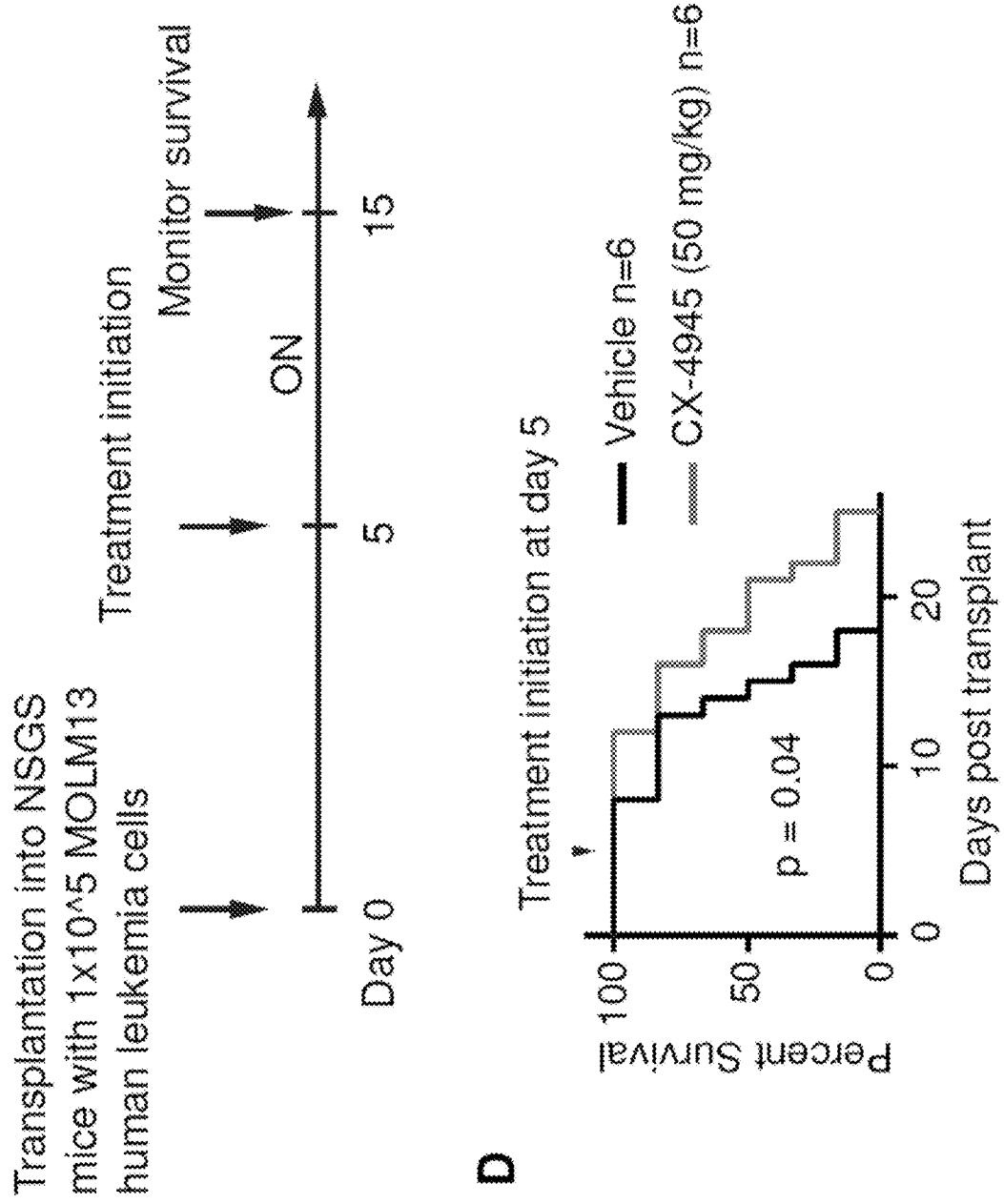
FIG. 7. CKII inhibition delays the leukemia progression and improves survival of MLL-AF9 mice and MOLM13 human leukemia mice. (A) Timeline of the MLL-AF9 leukemia mouse model and CKII inhibitor treatment. Drug treatments were started at day 10 after transplantation. (B) Kaplan-Meier survival curves of secondary transplanted C57BL/6 mice after vehicle and CX-4945 treatment at day 10. Vehicle or CX-4945 (50 mg/kg or 75 mg/kg) were administered twice daily by oral gavage for a total of twenty treatments. Leukemia was confirmed at the endpoint for each transplant mouse. The number (n) indicates the number of mice in each group. The p values were calculated using the log rank test. (C) Timeline of the MOLM13 human leukemia xenograft mice. Drug treatments were started at day 5 after transplantation. (D) Kaplan-Meier survival curves of NSGS mice after vehicle and CX-4945 treatment. Vehicle or CX-4945 (50 mg/kg) were administered twice daily by oral gavage for a total of twenty treatments. Leukemia was confirmed at the endpoint for each transplant mouse by flow cytometry, H&E staining and histology analysis. The number (n) indicates the number of mice in each group. The p value was calculated using the log rank test. (E) Taspase1 cleavage regulation of MLL1 mediated by CKII phosphorylation. MLL1 cleavage by taspase1 primed the protein to degradation pathway. In the absence of taspase1 cleavage, MLL1 protein is relatively more stable and preferentially associated with chromatin. CKII phosphorylation on MLL1 near the cleavage sites facilitate the cleavage event. Stabilization of the full-length MLL1 could be achieved by pharmacological inhibition of CKII phosphorylation on MLL1. The stabilized MLL1 protein expels the MLL translocation partners and SEC involvement in leukemogenesis.
Figure 7:
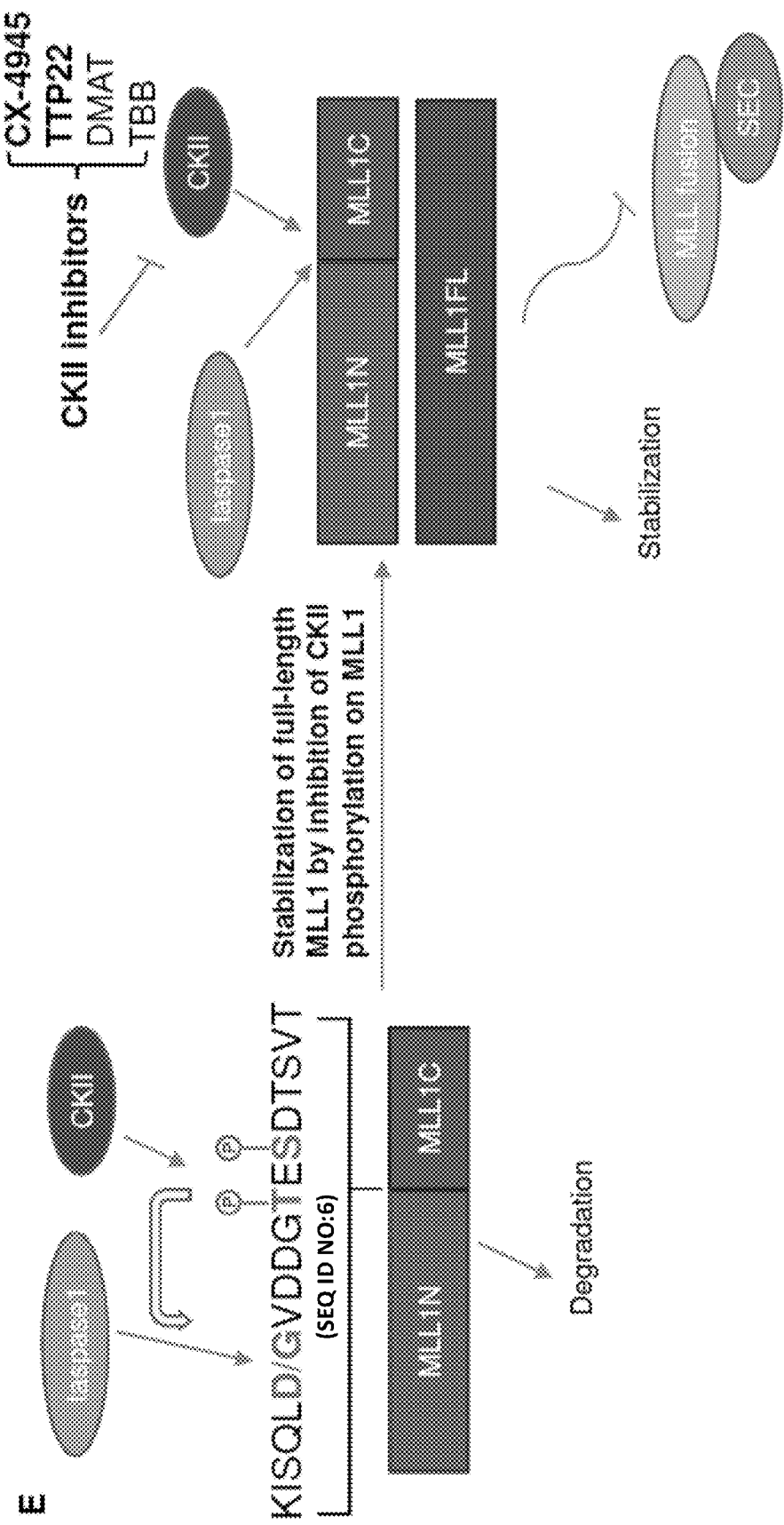
Figure 8:
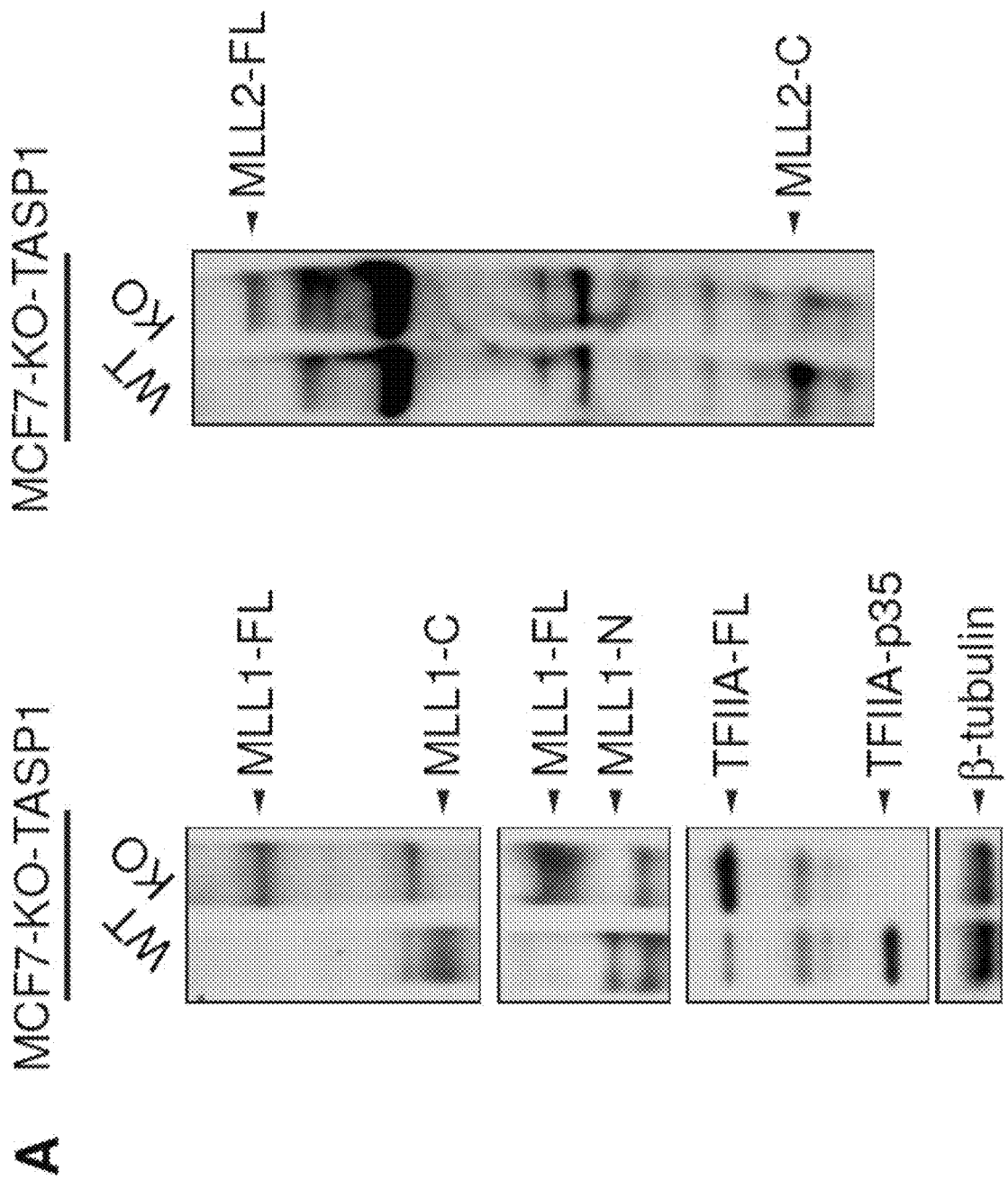
FIG. 8. Loss of taspase1 does not affect global H3K4 methylation and the cellular localization of MLL1 and MLL2. (A) Validation of taspase1 KO in MCF7 cells by immunoblotting with MLL1, MLL2 and TFIIA. (B) Validation of taspase1 KO in HCT116 cells by immunoblotting with MLL1 and TFIIA. (C) H3K4 methylation is not altered in HCT116 cells with loss of taspase1. (D) MLL1 C-terminal, and (E) MLL2 C-terminal antibodies are used in the immunofluorescence showing the nuclear localization of MLL1 and MLL2 proteins. (F) Taspase1 WT and KO cell lysates were immunoprecipitated against IgG or RbBP5 and blotted with MLL1 C-terminal antibody. (G) Gel filtration experiment showing the MLL1/COMPASS complex was not disrupted without the cleavage of MLL1 by taspase1.
Figure 8:
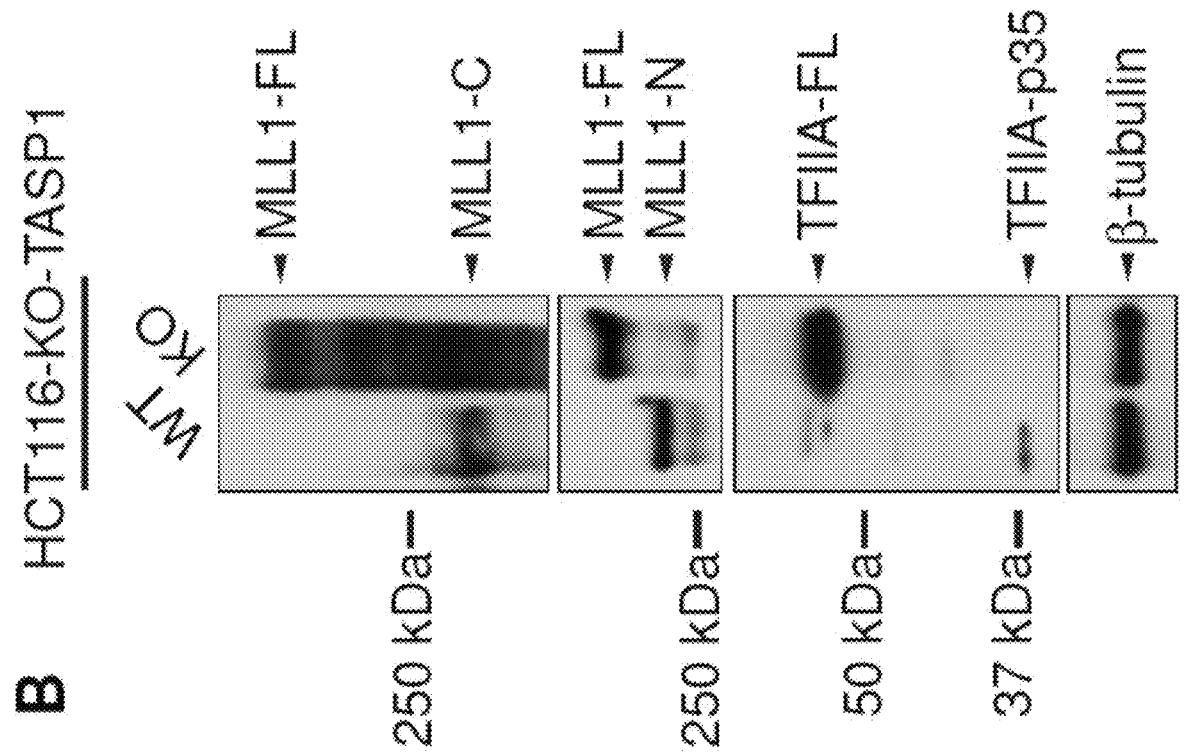
Figure 8:
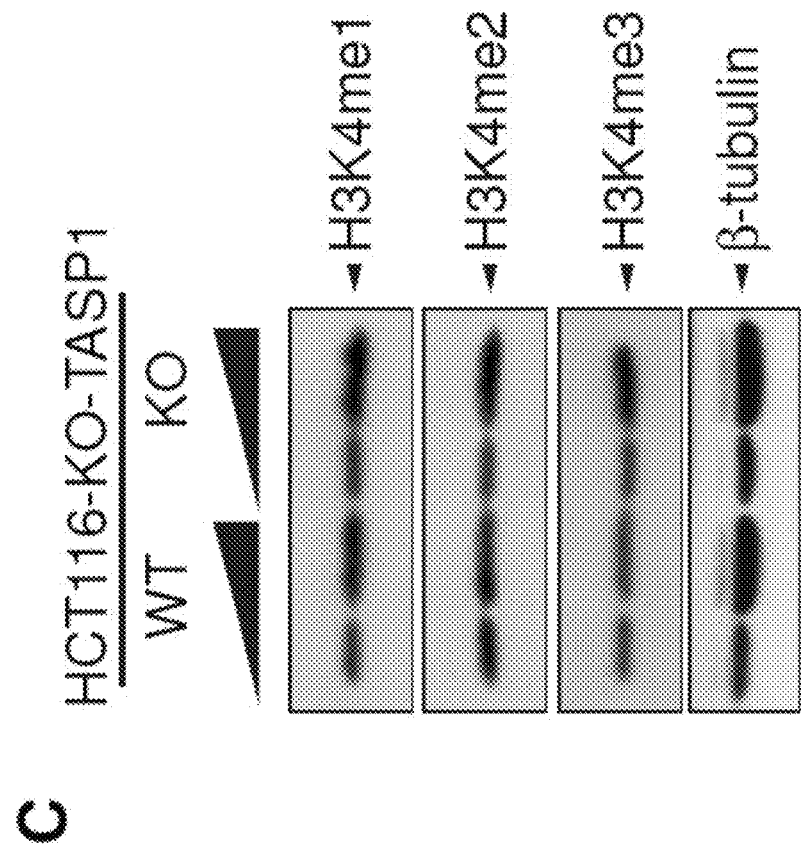
Figure 8:
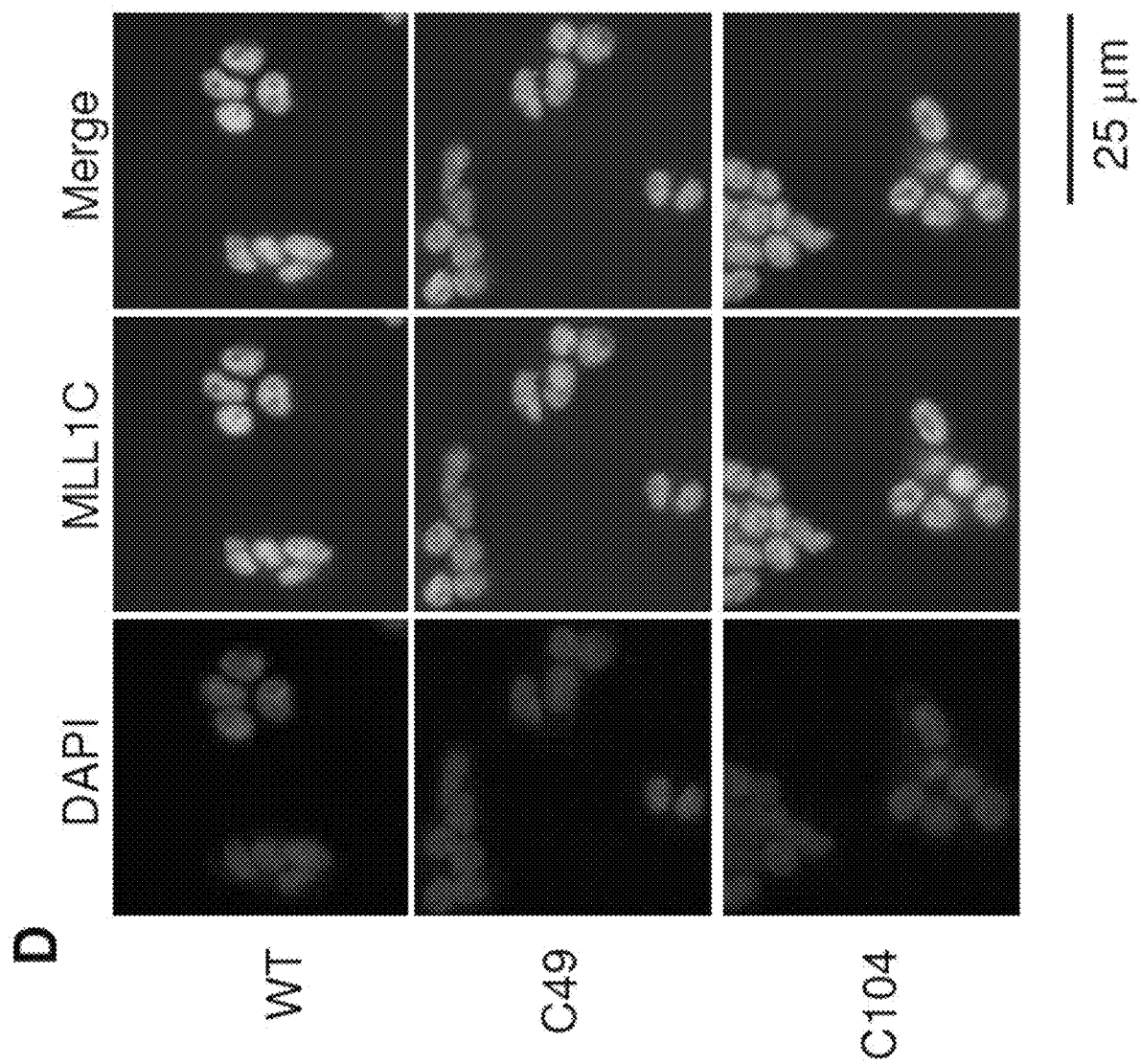
Figure 8:
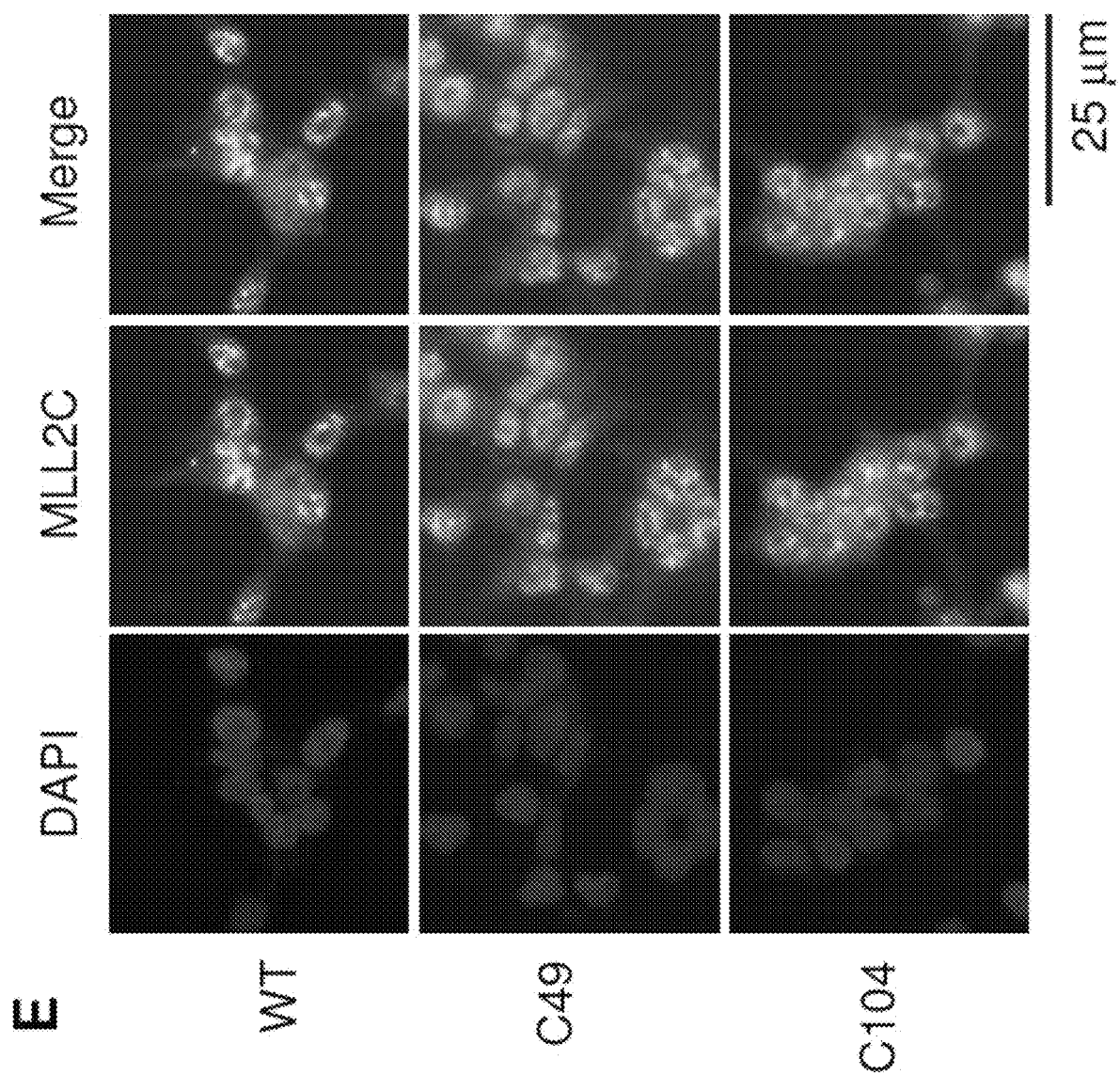
Figure 8:
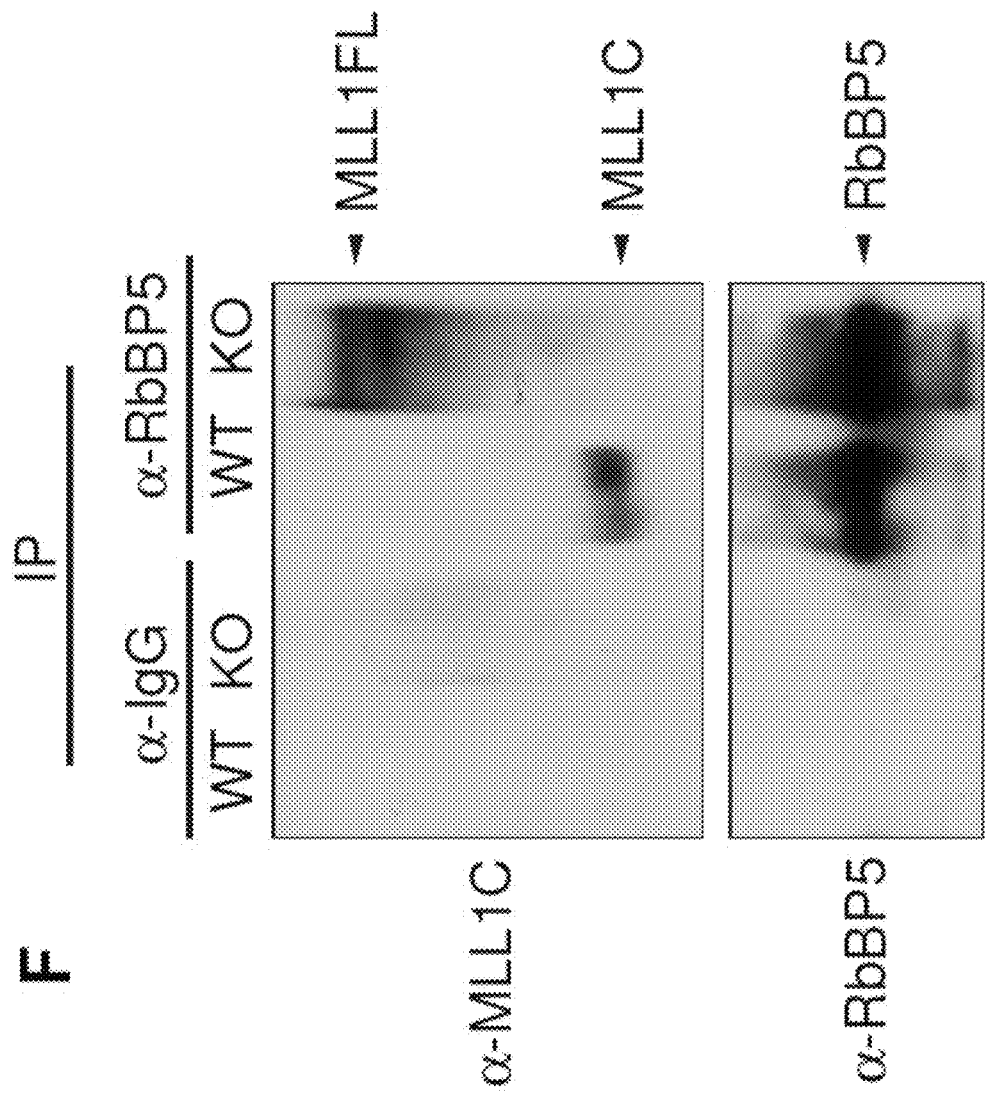
Figure 8:
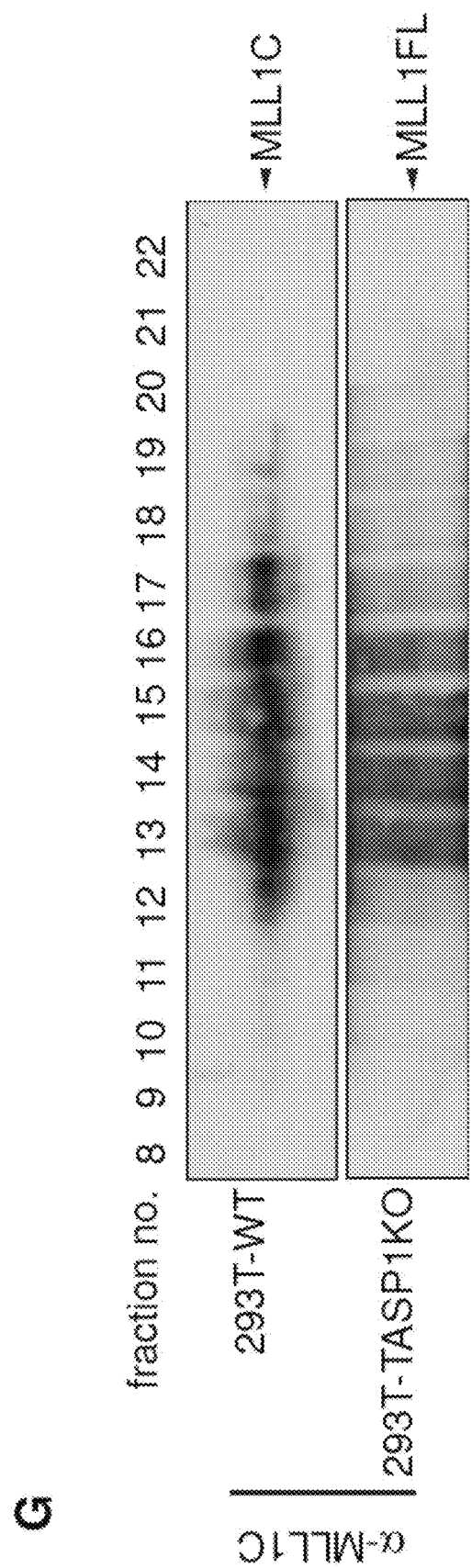

Here, we report our identification of taspase1 as an important MLL1 stability regulator. Specifically, we demonstrated that (1) Loss of taspase1 inhibited cell proliferation and colony formation ability of the cells in vitro by successfully establishing taspase1 knockout cells with CRISPR/Cas9 (FIG. 1 and FIG. 8); (2) Cleavage of MLL1 by taspase1 did not affect its cellular localization and binding to other COMPASS complex subunits (FIG. 8), but affected the stability (FIG. 2) and turnover of MLL1 subunits on the chromatin (FIG. 3), (3) CKII inhibition increases the genome-wide MLL occupancy and excludes SEC recruitment through de-phosphorylation of MLL1 near the taspase1 cleavage sites (FIGS. 5 and 6), and (4) CKII inhibition via MLL1 stabilizing significantly delayed the leukemia progression in MLL-AF9 mice (FIG. 7).

MLL1 stability control is a precise process that determines its activity and occupancy at the target genes. The functions of MLL1 are substantially affected if the degradation machinery is altered. However, how MLL1 protein stability is controlled remains debated. During hematopoietic differentiation, it has been shown that the ubiquitination and degradation of MLL1 was mediated by $ECS^{ASB2}$, while the MLL-AF9 fusion protein was resistant to ASB2-mediated degradation (Wang et al. 2012a). Interestingly, they found that ASB2-induced MLL1 degradation reduced its transactivation ability (Wang et al. 2012a). We recently showed that MLL1 stability could be regulated by IL1/IRAK4 pathway through UBE2O (Liang et al. 2017). We believe that the cleavage of MLL1 by taspase1 may cause a conformational alteration and exposes MLL1 to certain E3 ligases or MLL1 PHD2 itself to undergo degradation process (Wang et al. 2012b; Liang et al. 2017). Studies have also been shown that the N- and C-terminal of MLL1 undergo distinct degradation processes where MLL1 N-terminus undergo FYRN-targeted degradation in the nucleus while MLL1 C-terminus is dependent on the proteasome-mediated degradation in the cytoplasm (Yokoyama et al. 2011). As shown by our biochemical analysis, the proteolytic cleavage of MLL1 by taspase1 is coupled with the degradation process, thus controlled the turnover of MLL1 protein on chromatin. Our study further proves that MLL1 requires the proteolytic-processed dissociation by taspase1 to direct each subunit to the distinct degradation mechanisms. More insights should be gained biochemical and structural analyses of the non-cleavable MLL1.

In the majority of cases, the leukemogenic fusion proteins contain the N-terminal MLL1 fused in frame to the C-terminal translocation partner, with the loss of taspase1 cleavage sites (Hess 2004). This renders the fusion proteins resistant to ubiquitin-proteasome mediated degradation (Wang et al. 2012a; Liang et al. 2017). Nevertheless, AF4-MLL oncoprotein is one of the exceptions containing the N-terminus of AF4 and C-terminal MLL1, which preserves the taspase1 cleavage site in the fusion protein, and is capable of inducing acute lymphoblastic leukemia (ALL) in mice (Kowarz et al. 2007; Bursen et al. 2010). Similar to the functionality of MLL through intra-molecular interaction between FYRN and FYRC domains (Yokoyama et al. 2013), the interaction is also important for oncogenic activation of AF4-MLL (Pless et al. 2011). Although studies have shown that expression of the dominant negative taspase1 resulted in the growth inhibition of SEM leukemic cells with AF4-MLL translocation, whether this is due to the proteasomal degradation of the fusion protein needs to be further carefully evaluated (Sabiani et al. 2015).

Proteolysis of nuclear proteins is a common mechanism essential for the proper activation of their downstream target gene expression (von Mikecz 2006). The nuclear ubiquitin-proteasome system is also required to regulate chromatin structure (von Mikecz 2006). Here, we discovered the proteolysis of MLL1 is also required for the release of MLL1 from the chromatin to fine tune the transcription regulation, adding a new layer of epigenetic regulation of the crosstalk between H3K4 methylation and degradation apparatus of the methyltransferase. Overall, taspase1 regulates MLL1 cleavage and degradation to control the levels of MLL1 for accurate transcription processes resemblant that of TFIIA (Hoiby et al. 2004; Zhou et al. 2006), with distinct ubiquitin-proteasome pathways. It remains to be identified the exact E3 ubiquitin ligases utilized in concert with taspase1 to control MLL1 turnover in the nucleus. Taspase1 localizes in the nucleus and cytoplasm depending on the substrate cleavage (Nataraj an et al. 2010; Bier et al. 2011a). Whether there are additional substrates or any ubiquitin-proteasome pathway proteins tethered to taspase1 remains to be revealed in order to fully understand the roles of taspase1 in normal development and disease settings. Our taspase1 knockout cells represent valuable tools for us to investigate the functions of taspase1, the only protease in the type 2 asparaginase family (Hsieh et al. 2003a).

Loss of taspase1 impedes cancer cell proliferation and tumor progression as shown in our study (FIG. 1D) and previous studies in breast cancer (Chen et al. 2010; Chen et al. 2012; Dong et al. 2014). Surprisingly, numerous membrane proteins are affected with the loss of taspase1 and this resulted in the altered extracellular matrix organization and regulation of cell adhesion (FIG. 11B). This consequence of taspase1 loss leads to the possibility that taspase1 expression may be important for the tumor progression in the tumor microenvironment, where the membrane receptor proteins directly contact with the immune cells to conduct the crosstalk. Therefore, it will be interesting to observe the effect of taspase1 KO in the in vivo system and tumor progression.

Figure 5:
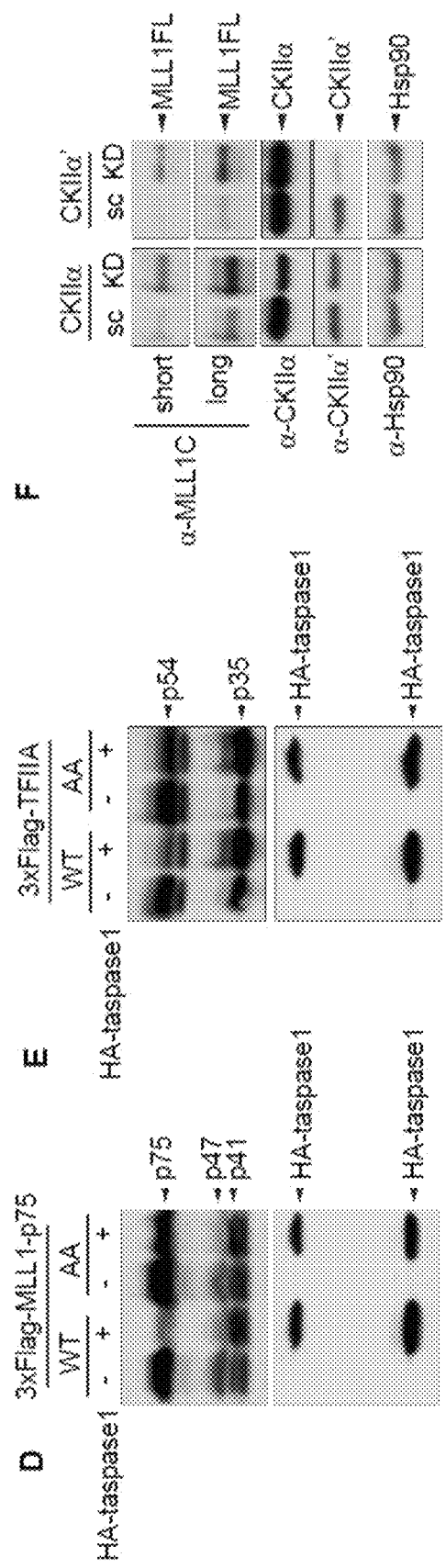
FIG. 5. CKII inhibitors selectively increase full-length MLL1 protein levels by decreasing the phosphorylation of MLL1 near the cleavage sites. (A) Conservation of the sequences flanking MLL1-CS2, MLL2 and TFIIA cleavage sites and phosphorylated serine and threonine residues after the cleavage sites (highlighted in red). (B) and (C) 293T cells were transfected with vector control (VT), WT, AA or DD reporter constructs of MLL1-p75 or TFIIA. Western blot was performed with anti-Flag antibody for MLL1 (p75: FL, p47: cleaved) or TFIIA (p54: FL, p47: cleaved). (D) and (E) 293T cells were transfected with WT or AA reporter constructs of MLL1-p75 or TFIIA in the presence or absence of HA-taspase1. Western blot was performed with anti-Flag antibody for MLL1 or TFIIA, or anti-HA antibody for taspase1. (F) 293T cells were infected with shRNAs against CKIIα or CKIIα'. Western blot was performed with anti-MLL1C antibody for MLL1 full-length protein levels, and CKIIα or CKIIα' for knockdown efficiency. (G) 293T cells were treated with DMSO or 10 µM CX-4945 for 30 hours. Cells were harvested and lysed for Western blot against MLL1, MLL2 or TFIIA using β-tubulin as the loading control. (H) and (I) 293T taspase1 KO cells were pre-treated with CX-4945 (3 µM) or TTP22 (10 µM) for 30 hours. Whole cell lysates from the two conditions were incubated with increasing concentrations of his-taspase1 and subject to in vitro taspase1 assay.
Figure 5:
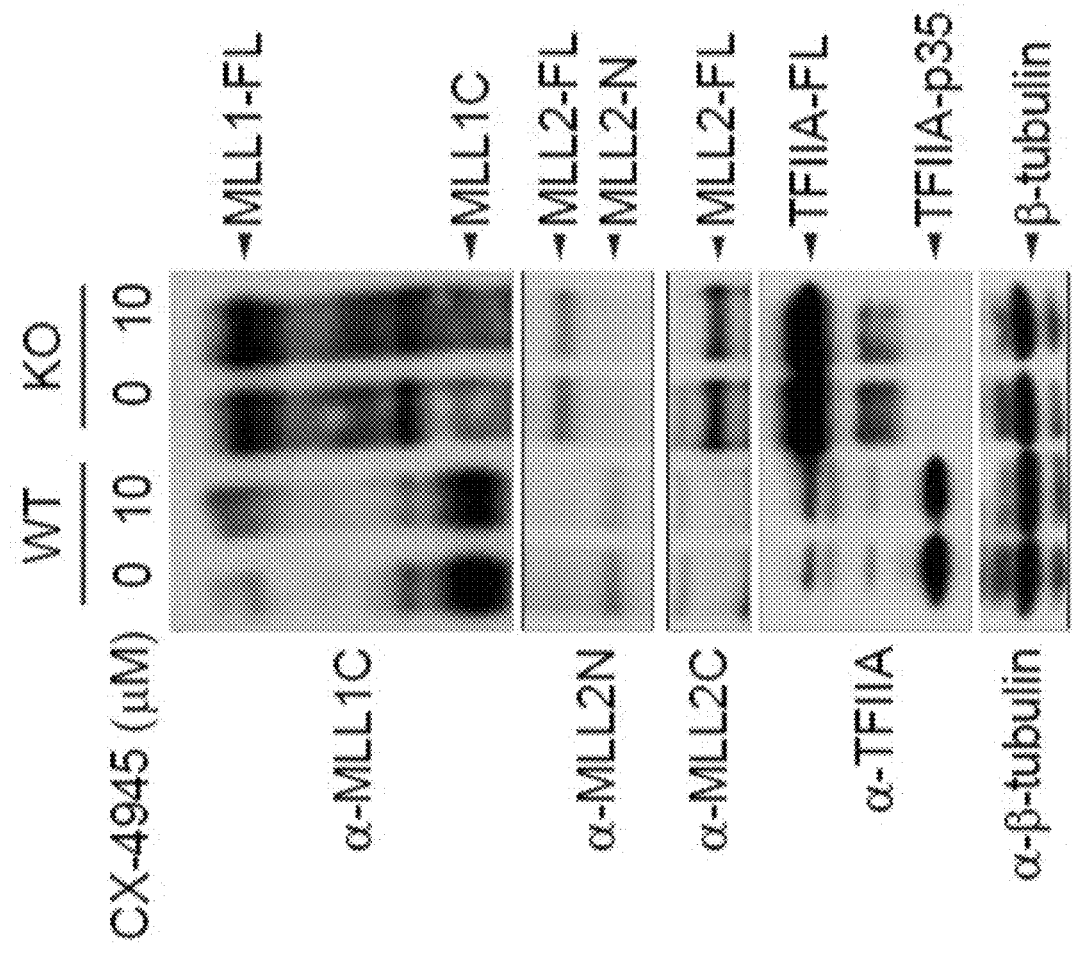
Figure 5:
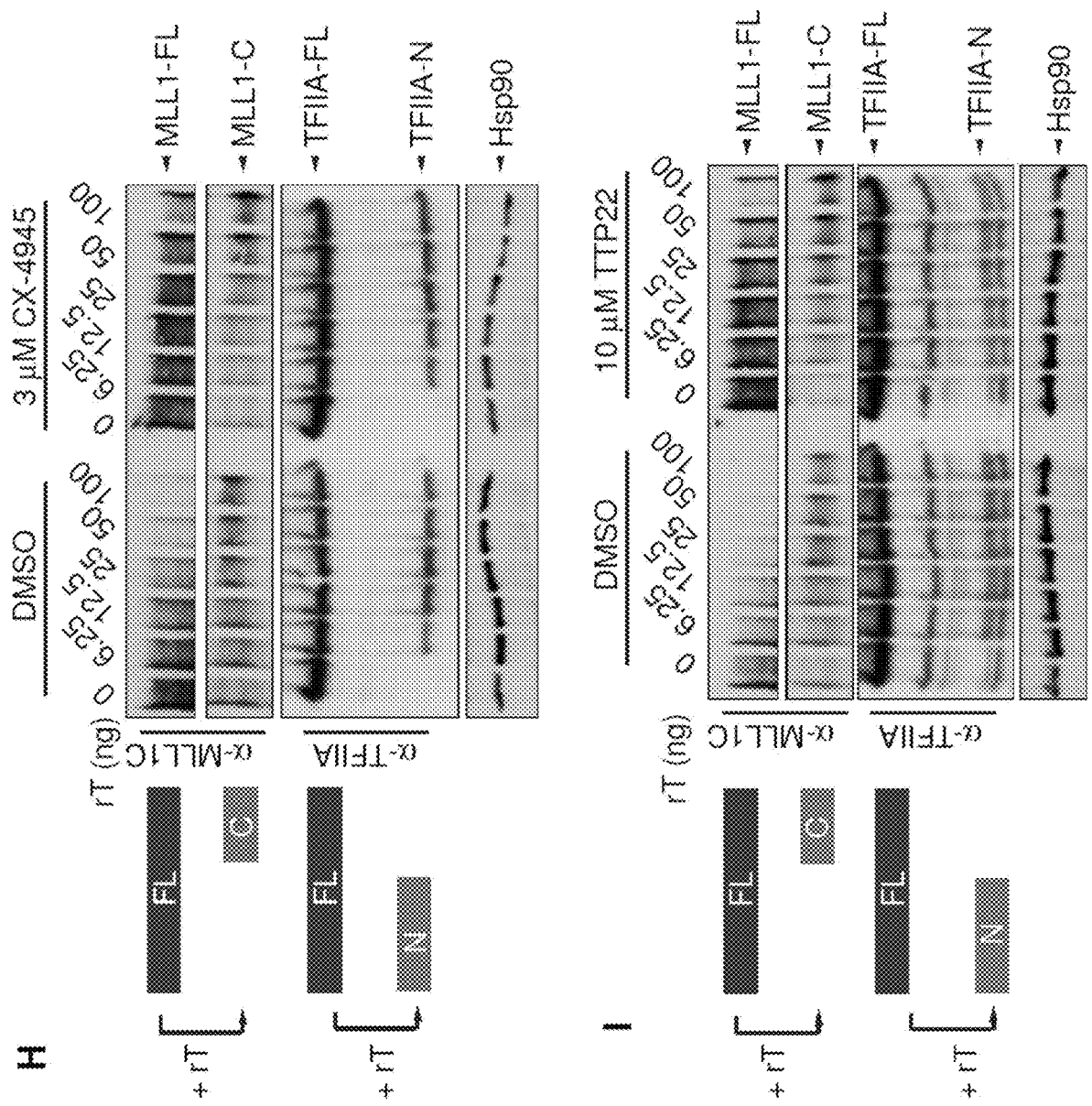

Taspase1 represents a superior therapeutic target for a variety of cancers treatment due to its overexpression in solid and liquid malignancies (Takeda et al. 2006; Chen et al. 2010; Bier et al. 2011b; Bier et al. 2012; Chen et al. 2012; Wunsch et al. 2016). However, due to its unique structure and function, it remains to be a hard-to-target candidate for leukemia and other solid tumors. Alternatively, we identified a new pathway regulating the substrate cleavage by taspase1, particularly, MLL1 by CKII phosphorylation (FIGS. 5 and 6). Stabilization of MLL through cleavage inhibition provides us with a paradigm in the development of therapies for MLL leukemia and other cancers caused by translocations or taspase1 overexpression.

Materials and Methods

Cell culture. All of the cell lines were purchased from the American Type Culture Collection (Rockville, Md.). 293T, MCF7 and HCT116 cell lines were maintained in Dulbecco's modified Eagle's medium (DMEM) (Gibco, Gaithersburg, Md.) supplemented with 10% fetal bovine serum (FBS) (Gibco) at 37° with 5% $CO_2$. SEM was maintained in IMDM with 10% FBS. MM6 was maintained in RPMI1640 supplemented with 10% FBS and non-essential amino acids. MOLM13, RS4:11, MV4-11, RL, REH, U937m SU-DHL-6 and OCI-LY1 were maintained in RPMI1640 supplemented with 10% FBS. For the cycloheximide (CHX) chase experiment, indicated concentrations of CHX (Sigma, St. Louis, Mo.) was added to the culture media for indicated time points before harvesting the cells. For CKII inhibitor treatment, indicated concentrations were added to the cell culture for 30 hours before harvesting the cells for western blot or in vitro taspase1 assay. CX-4945, TTP22, DMAT and TTB were purchased from ApexBio (Houston, Tex.).

Knockout taspase1 by CRISPR/Cas9 targeted genome editing. Cells were co-transfected with gRNA and pX330-U6-Chimeric_BB-CBh-hSpCas9 (Cong and Zhang 2015) and another vector with puromycin resistance using Lipofectamine 2000 (ThermoFisher Scientific, Waltham, Mass.) and selected with puromycin (ThermoFisher Scientific) at 2 ug/ml for 3 days. Cells were seeded in 96-well plates and selected for single clones after 2-3 weeks. Genomic DNA was isolated using genomic lysis buffer (10 mM Tris-HCl pH 7.5, 10 mM EDTA, 10 mM NaCl and 0.5% sarcosyl) at 60° C. for 2 hours and precipitation buffer (150 mM NaCl in 100% EtOH) at room temperature for 30 minutes. PCR screening was performed using the primers listed in Table I and further confirmed by western blot and RNA-seq. pX330-U6-Chimeric_BB-CBh-hSpCas9 was a gift from Feng Zhang (Addgene plasmid #42230).

Virus packaging, infection and stable cell line generation. Lentiviruses for knocking down MLL1, taspase1, CKIIα and CKIIα' were packaged as previously described (Zhao et al. 2014). The shRNA sequences used were listed in Table I. Cells were selected with 2 μg/ml puromycin for three days before western blot and ChIP-seq experiments, Immunofluorescence Immunofluorescence was performed as previously described (Wang et al. 2014; Wang et al. 2017). Anti-MLL1N (D2M7U) and MLL1C (D6G8N) antibodies were purchased from Cell Signaling Technology (Denvers, Mass.). Anti-MLL2C antibody was validated in our previous studies (Hu et al. 2013).

Immunoprecipitation. 293T cells were lysed in Triton X-100 lysis buffer (50 mM Tris pH 8.0, 150 mM NaCl, 0.5% Triton X-100, 10% glycerol, 1 mM DTT, protease inhibitors and benzonase). After centrifugation at 13,000 g for 10 min, the supernatants (1 mg total protein) were collected and incubated with anti-Flag M2 affinity gel at 4° C. for 2 h with rotation. Samples were washed with lysis buffer four times, and competed with 3× Flag peptides for 15 min with vigorous agitation. Proteins were resuspended in 5× SDS sample loading buffer, heated to 95° C. for 5 min, and subjected to SDS-PAGE.

Western blot analysis. Western blot analysis was performed as previously described (Zhao et al. 2013). Anti-TFIIA and anti-RbBP5 antibodies were purchased from Bethyl Laboratories (Montgomery, Tex.). Anti-taspase1 Thermo Fisher Scientific (Waltham, Mass.). Anti-MLL2N and MLL2C antibodies and anti-histone H3K4me1, H3K4me2 and H3K4me3 antibodies were homemade and validated in our previous studies (Hu et al. 2013; Rickels et al. 2016). Anti-Hsp90 antibodies were purchased from Santa Cruz Biotechnology (Santa Cruz, Calif.).

Cell Proliferation Assay. Cell proliferation was measured by cell counting using the Vi-CELL™ Cell Counter (Beckman Coulter Life Sciences, Indianapolis, Ind.). Culture media were changed freshly every two days.

2-D Colony formation assay. Colony formation assay was performed as previously described (Noetzel et al. 2012). 293T cells were seeded 200 cells/well in the 6-well plates and culture medium was replaced every four days for two weeks. Cells were then fixed with 3.7% paraformaldehyde and stained with 0.05% crystal violet.

in vitro taspase1 cleavage assay. Taspase1 KO whole cell lysates (~25 μg) were incubated with various amount of his-taspase1 purified from BL21 E. coli for 1 hour at 30° C. in the cleavage buffer (100 mM HEPES pH7.9, 5 mM MgCl2, 20 mM KCl, 10% sucrose, 5 mM DTT). Cleavage efficiency was detected by western blot against MLL1C and TFIIA using Hsp90 as the loading control.

NGS Data Processing. RNA-seq and ChIP-seq samples were sequenced with the Illumina NextSeq technology, and output data were processed with the bcl2fastq software tool. Sequence quality was assessed using FastQC v 0.11.2 (Andrew 2010), and quality trimming was done using the FASTX toolkit. RNA-seq and ChIP-seq reads were aligned to the hg19 genome using TopHat v2.0.9 (Kim et al. 2013) and Bowtie v0.12.9 (Langmead et al. 2009), and only uniquely mapped reads with a two-mismatch threshold were considered for downstream analysis. Gene annotations from Ensembl 72 were used. Output bam files were converted into bigwig track files to display coverage throughout the genome (in RPM) using the GenomicRanges package (Lawrence et al. 2013) as well as other standard Bioconductor R packages.

RNA-seq Analysis. Gene count tables were constructed using HTseq (Anders et al. 2015) with Ensembl gene annotations and used as input for edgeR 3.0.8 (Robinson et al. 2010). Genes with Benjamini-Hochburg adjusted p-values less than 0.01 were considered to be differentially expressed. GO enrichment analysis was evaluated by the MetaScape online software suite (Tripathi et al. 2015).

ChIP-seq Analysis. $5 \times 10^7$ cells were used for each ChIP assay, as performed as previously described (Chen et al. 2015). Peaks were called with MACS v1.4.2 (Zhang et al. 2008) using default parameters and were annotated by the HOMER software (Heinz et al. 2010). Metaplots were generated using ngsplot (Shen et al. 2014). For FIGS. 5 and 7, MLL1 and MLL2 peaks from wildtype and knockout/knockdown samples were merged, and bedtools was used to determine the raw counts at these merged peaks (Quinlan and Hall 2010). Using in-house perl scripts, raw counts at each peak were converted to RPKM values with total library counts, and log fold change values between conditions were then computed with these normalized values. Differential occupancy of MLL1 was evaluated by edgeR, and peaks with Benjamini-Hochburg adjusted p-values less than 0.05 were considered to be differentially occupied. For FIG. 7, nearest genes were identified using in-house perl scripts based on distances between peak centers and TSSs.

MLL-AF9 Leukemia Cell Generation. HSPCs from C57BL/6 mice were isolated as described above and spinoculated with MIGR1-MLL-AF9-IRES-Neo retrovirus at 2500 RPM for 90 minutes at 32C. Two days following spinoculation, HSPCs were treated with G418 at a 1:125 concentration (Sigma). Once all non-transduced cells were eliminated, the remaining cells were transferred to leukemic cell (LC) media consisting of RPMI-1640 supplemented with 10% FBS, penicillin/streptomycin, L-glutamine, 100 ng/mL recombinant mSCF, 50 ng/mL recombinant mIL6, and 20 ng/mL recombinant mIL3 to expand. $2 \times 10^6$ MLL-AF9 pre-leukemic cells were transplanted into irradiated recipient mice via the tail vein along with $2 \times 10^5$ bone marrow support cells. Mice developed disease after 2-3 months, and spleens were harvested. Mononuclear cells from spleens of diseased mice were dissociated and cultured in LC media with G418 for an additional five days to eliminate non-LCs from culture. These cells were used for all MLL-AF9 leukemic cell studies.

Leukemic Cell Transplantation and Treatment. 8-10-week-old C57BL/6 female recipient mice were exposed to 9 Gy of ionizing radiation in a Gammacell 40 irradiator Immediately prior to irradiation and 14 days afterwards, mice were fed bactrim-supplemented water. Each mouse was injected with $5 \times 10^4$ MLL-AF9 leukemic cells as well as $2 \times 10^5$ wild-type bone marrow support cells by the tail vein following irradiation. After 10 days of recovery, mice were treated twice-daily for two weeks (5 days on, 2 days off, 5 days on) with either vehicle or CX-4945 at indicated doses by oral gavage. All mice were housed at Northwestern University and all studies were performed with prior IACUC approval. CX-4945 compound was purchased from APExBIO and synthesized in-house according to the previously published procedure (Pierre et al. 2011).

MLL Murine Xenograft Transplantation and Treatment. All animal studies were conducted in accordance with the guidelines of Northwestern University's Institutional Animal Care and Use Committee and housed in Northwestern University's vivarium. Six week old, NSGS mice (NOD-scid IL2Rgnull-3/GM/SF or NSG-SGM3, Jackson Laboratory) were transplanted via tail vein intravenous injection with $1 \times 10^5$ MOLM13 cells (DSMZ ACC-554), a human, MLL-rearranged, AML cell line. Transplanted mice were randomly assigned to groups for treatment with either vehicle (n=6) or CX-4945 at 50 mg/kg (n=6) via oral gavage twice daily for 10 consecutive days. Mice were monitored for illness including signs of lethargy, ruffled coat, and/or hind limb paralysis at which time mice were sacrificed for analysis. Burden efficacy, treatment efficacy, and treatment efficacy were assessed via peripheral blood and bone marrow analysis with CBC (Hemavet 950, Drew Scientific), flow cytometry (briefly, RBCs were lysed in Gibco's ACK lysis buffer, blocked with human BD Fc Block, stained with BioLegends anti-hCD45, anti-hCD33, and anti-mCD45 antibodies, and cells quantified using BD Biosciences FACSAria), and histology of paraffin-embedded tissue (murine livers, spleens, and decalcified sternums and femurs were processed, sectioned, stained, and slide images digitized by Northwestern University's Mouse Histology and phenotyping Laboratory and Pathology Core Facility using H&E stain and immunohistochemistry with anti-hCD45, Dako M0701).

REFERENCES

Andrews S. 2010. FastQC: a quality control tool for high throughput sequence data. Available online at the following website: http://www.bioinformatics.babraham.ac.uk/projects/fastqc.

Anders S, Pyl P T, Huber W. 2015. HTSeq—a Python framework to work with high-throughput sequencing data. Bioinformatics 31: 166-169.

Armstrong S A, Staunton J E, Silverman L B, Pieters R, den Boer M L, Minden M D, Sallan S E, Lander E S, Golub T R, Korsmeyer S J. 2002. MLL translocations specify a distinct gene expression profile that distinguishes a unique leukemia. Nat Genet 30: 41-47.

Ayton P M, Cleary M L. 2003. Transformation of myeloid progenitors by MLL oncoproteins is dependent on Hoxa7 and Hoxa9. Genes & development 17: 2298-2307.

Bier C, Hecht R, Kunst L, Scheiding S, Wunsch D, Goesswein D, Schneider G, Kramer O H, Knauer S K, Stauber R H. 2012. Overexpression of the catalytically impaired Taspase1 T234V or Taspase1 D233A variants does not have a dominant negative effect in T(4;11) leukemia cells. PloS one 7: e34142.

Bier C, Knauer S K, Docter D, Schneider G, Kramer O H, Stauber R H. 2011a. The importin-alpha/nucleophosmin switch controls taspase1 protease function. Traffic 12: 703-714.

Bier C, Knauer S K, Klapthor A, Schweitzer A, Rekik A, Kramer O H, Marschalek R, Stauber R H. 2011b. Cell-based analysis of structure-function activity of threonine aspartase 1. The Journal of biological chemistry 286: 3007-3017.

Blom N, Sicheritz-Ponten T, Gupta R, Gammeltoft S, Brunak S. 2004. Prediction of post-translational glycosylation and phosphorylation of proteins from the amino acid sequence. Proteomics 4: 1633-1649.

Bursen A, Schwabe K, Ruster B, Henschler R, Ruthardt M, Dingermann T, Marschalek R. 2010. The AF4.MLL fusion protein is capable of inducing ALL in mice without requirement of MLL.AF4. Blood 115: 3570-3579, Capotosti F, Guernier S, Lammers F, Waridel P, Cai Y, Jin J, Conaway J W, Conaway R C, Herr W. 2011. O-GlcNAc transferase catalyzes site-specific proteolysis of HCF-1. Cell 144: 376-388.

Capotosti F, Hsieh J J, Herr W. 2007. Species selectivity of mixed-lineage leukemia/trithorax and HCF proteolytic maturation pathways. Mol Cell Biol 27: 7063-7072.

Chen D Y, Lee Y, Van Tine B A, Searleman A C, Westergard T D, Liu H, Tu H C, Takeda S, Dong Y, Piwnica-Worms D R et al. 2012. A pharmacologic inhibitor of the protease Taspase1 effectively inhibits breast and brain tumor growth. Cancer research 72: 736-746.

Chen D Y, Liu H, Takeda S, Tu H C, Sasagawa S, Van Tine B A, Lu D, Cheng E H, Hsieh J J. 2010. Taspase1 functions as a non-oncogene addiction protease that coordinates cancer cell proliferation and apoptosis. Cancer research 70: 5358-5367.

Chen F X, Woodfin A R, Gardini A, Rickels R A, Marshall S A, Smith E R, Shiekhattar R, Shilatifard A. 2015. PAF1, a Molecular Regulator of Promoter-Proximal Pausing by RNA Polymerase II. Cell 162: 1003-1015.

Cong L, Zhang F. 2015. Genome Engineering Using CRISPR-Cas9 System. Methods Mol Biol 1239: 197-217.

Daou S, Mashtalir N, Hammond-Martel I, Pak H, Yu H, Sui G, Vogel J L, Kristie T M, Affar el B. 2011. Crosstalk between O-GlcNAcylation and proteolytic cleavage regulates the host cell factor-1 maturation pathway. Proc Natl Acad Sci USA 108: 2747-2752.

Dong Y, Van Tine B A, Oyama T, Wang P I, Cheng E H, Hsieh J J. 2014. Taspase1 cleaves MLL1 to activate cyclin E for HER2/neu breast tumorigenesis. Cell research 24: 1354-1366.

Fair K, Anderson M, Bulanova E, Mi H, Tropschug M, Diaz M O. 2001. Protein interactions of the MLL PHD fingers modulate MLL target gene regulation in human cells. Mol Cell Biol 21: 3589-3597.

Heinz S, Benner C, Spann N, Bertolino E, Lin Y C, Laslo P, Cheng J X, Murre C, Singh H, Glass C K. 2010. Simple combinations of lineage-determining transcription factors prime cis-regulatory elements required for macrophage and B cell identities. Mol Cell 38: 576-589.

Hess J L. 2004. Mechanisms of transformation by MLL. Crit Rev Eukaryot Gene Expr 14: 235-254.

Hoiby T, Mitsiou D J, Zhou H Q, Erdjument-Bromage H, Tempst P, Stunnenberg H G. 2004. Cleavage and proteasome-mediated degradation of the basal transcription factor TFIIA. Embo J 23: 3083-3091.

Hornbeck P V, Zhang B, Murray B, Kornhauser J M, Latham V, Skrzypek E. 2015. PhosphoSitePlus, 2014: mutations, PTMs and recalibrations. Nucleic acids research 43: D512-520.

Hsieh J J, Cheng E H, Korsmeyer S J. 2003a. Taspase1: a threonine aspartase required for cleavage of MLL and proper HOX gene expression. Cell 115: 293-303.

Hsieh J J, Ernst P, Erdjument-Bromage H, Tempst P, Korsmeyer S J. 2003b. Proteolytic cleavage of MLL generates a complex of N- and C-terminal fragments that confers protein stability and subnuclear localization. Mol Cell Biol 23: 186-194.

Hu D, Garruss A S, Gao X, Morgan M A, Cook M, Smith E R, Shilatifard A. 2013. The Mll2 branch of the COMPASS family regulates bivalent promoters in mouse embryonic stem cells. Nature structural & molecular biology 20: 1093-1097.

Khan J A, Dunn B M, Tong L. 2005. Crystal structure of human Taspase1, a crucial protease regulating the function of MLL. Structure 13: 1443-1452.

Kim D, Pertea G, Trapnell C, Pimentel H, Kelley R, Salzberg S L. 2013. TopHat2: accurate alignment of transcriptomes in the presence of insertions, deletions and gene fusions. Genome biology 14: R36.

Kowarz E, Burmeister T, Lo Nigro L, Jansen M W, Delabesse E, Klingebiel T, Dingermann T, Meyer C, Marschalek R. 2007. Complex MLL rearrangements in t(4;11) leukemia patients with absent AF4.MLL fusion allele. Leukemia 21: 1232-1238.

Langmead B, Trapnell C, Pop M, Salzberg S L. 2009. Ultrafast and memory-efficient alignment of short DNA sequences to the human genome. Genome biology 10: R25.

Lawrence M, Huber W, Pages H, Aboyoun P, Carlson M, Gentleman R, Morgan M T, Carey V J. 2013. Software for computing and annotating genomic ranges. PLoS computational biology 9: e1003118.

Liang K, Volk A G, Haug J S, Marshall S A, Woodfin A R, Bartom E T, Gilmore J M, Florens L, Washburn M P, Sullivan K D et al. 2017. Therapeutic Targeting of MLL Degradation Pathways in MLL-Rearranged Leukemia. Cell 168: 59-72 e13.

Luo Z, Lin C, Shilatifard A. 2012. The super elongation complex (SEC) family in transcriptional control. Nat Rev Mol Cell Biol 13: 543-547.

Meggio F, Marin O, Pinna L A. 1994. Substrate specificity of protein kinase CK2. Cellular & molecular biology research 40: 401-409.

Miller T, Krogan N J, Dover J, Erdjument-Bromage H, Tempst P, Johnston M, Greenblatt J F, Shilatifard A. 2001. COMPASS: a complex of proteins associated with a trithorax-related SET domain protein. Proc Natl Acad Sci USA 98: 12902-12907.

Milne T A, Briggs S D, Brock H W, Martin M E, Gibbs D, Allis C D, Hess J L. 2002. MLL targets SET domain methyltransferase activity to Hox gene promoters. Mol Cell 10: 1107-1117.

Nakamura T, Mori T, Tada S, Krajewski W, Rozovskaia T, Wassell R, Dubois G, Mazo A, Croce C M, Canaani E. 2002. ALL-1 is a histone methyltransferase that assembles a supercomplex of proteins involved in transcriptional regulation. Mol Cell 10: 1119-1128.

Natarajan T G, Kallakury B V, Sheehan C E, Bartlett M B, Ganesan N, Preet A, Ross J S, Fitzgerald K T. 2010. Epigenetic regulator MLL2 shows altered expression in cancer cell lines and tumors from human breast and colon. Cancer cell international 10: 13.

Noetzel E, Rose M, Bornemann J, Gajewski M, Knuchel R, Dahl E. 2012. Nuclear transport receptor karyopherin-alpha2 promotes malignant breast cancer phenotypes in vitro. Oncogene 31: 2101-2114.

Pierre F, Chua P C, O'Brien S E, Siddiqui-Jain A, Bourbon P, Haddach M, Michaux J, Nagasawa J, Schwaebe M K, Stefan E et al. 2011. Discovery and SAR of 5-(3-chlorophenylamino)benzo[c][2,6]naphthyridine-8-carboxylic acid (CX-4945), the first clinical stage inhibitor of protein kinase CK2 for the treatment of cancer. Journal of medicinal chemistry 54: 635-654.

Piunti A, Shilatifard A. 2016. Epigenetic balance of gene expression by Polycomb and COMPASS families Science 352: aad9780.

Pless B, Oehm C, Knauer S, Stauber R H, Dingermann T, Marschalek R. 2011. The heterodimerization domains of MLL-FYRN and FYRC—are potential target structures in t(4;11) leukemia. Leukemia 25: 663-670.

Quinlan A R, Hall I M. 2010. BEDTools: a flexible suite of utilities for comparing genomic features. Bioinformatics 26: 841-842.

Rickels R, Hu D, Collings C K, Woodfin A R, Piunti A, Mohan M, Herz H M, Kvon E, Shilatifard A. 2016. An Evolutionary Conserved Epigenetic Mark of Polycomb Response Elements Implemented by Trx/MLL/COMPASS. Mol Cell 63: 318-328.

Robinson M D, McCarthy D J, Smyth G K. 2010. edgeR: a Bioconductor package for differential expression analysis of digital gene expression data. Bioinformatics 26: 139-140.

Rush J, Moritz A, Lee K A, Guo A, Goss V L, Spek E J, Zhang H, Zha X M, Polakiewicz R D, Comb M J. 2005 Immunoaffinity profiling of tyrosine phosphorylation in cancer cells. Nature biotechnology 23: 94-101.

Sabiani S, Geppert T, Engelbrecht C, Kowarz E, Schneider G, Marschalek R. 2015. Unraveling the Activation Mechanism of Taspase1 which Controls the Oncogenic AF4-MLL Fusion Protein. EBioMedicine 2: 386-395.

Sarno S, Vaglio P, Meggio F, Issinger O G, Pinna L A. 1996. Protein kinase CK2 mutants defective in substrate recognition. Purification and kinetic analysis. The Journal of biological chemistry 271: 10595-10601.

Schuettengruber B, Bourbon H M, Di Croce L, Cavalli G. 2017. Genome Regulation by Polycomb and Trithorax: 70 Years and Counting. Cell 171: 34-57.

Shen L, Shao N, Liu X, Nestler E. 2014. ngs.plot: Quick mining and visualization of next-generation sequencing data by integrating genomic databases. BMC genomics 15: 284.

Shilatifard A, Duan D R, Haque D, Florence C, Schubach W H, Conaway J W, Conaway R C. 1997. ELL2, a new member of an ELL family of RNA polymerase II elongation factors. Proc Natl Acad Sci USA 94: 3639-3643.

Smith E, Lin C, Shilatifard A. 2011. The super elongation complex (SEC) and MLL in development and disease. Genes & development 25: 661-672.

Stauber R H, Bier C, Knauer S K. 2012. Targeting Taspase1 for cancer therapy—letter. Cancer research 72: 2912; author reply 2913.

Takeda S, Chen D Y, Westergard T D, Fisher J K, Rubens J A, Sasagawa S, Kan J T, Korsmeyer S J, Cheng E H, Hsieh J J. 2006. Proteolysis of MLL family proteins is essential for taspase1-orchestrated cell cycle progression. Genes & development 20: 2397-2409.

Tripathi S, Pohl M O, Zhou Y, Rodriguez-Frandsen A, Wang G, Stein D A, Moulton H M, DeJesus P, Che J, Mulder L C et al. 2015. Meta- and Orthogonal Integration of Influenza "OMICs" Data Defines a Role for UBR4 in Virus Budding. Cell host & microbe 18: 723-735.

von Mikecz A. 2006. The nuclear ubiquitin-proteasome system. J Cell Sci 119: 1977-1984.

Wang J, Muntean A G, Hess J L. 2012a. ECSASB2 mediates MLL degradation during hematopoietic differentiation. Blood 119: 1151-1161.

Wang J, Muntean A G, Wu L, Hess J L. 2012b. A subset of mixed lineage leukemia proteins has plant homeodomain (PHD)-mediated E3 ligase activity. The Journal of biological chemistry 287: 43410-43416.

Wang L, Collings C K, Zhao Z, Cozzolino K A, Ma Q, Liang K, Marshall S A, Sze C C, Hashizume R, Savas J N et al. 2017. A cytoplasmic COMPASS is necessary for cell survival and triple-negative breast cancer pathogenesis by regulating metabolism. Genes & development 31: 2056-2066.

Wang L, Zhao Z, Meyer M B, Saha S, Yu M, Guo A, Wisinski K B, Huang W, Cai W, Pike J W et al. 2014. CARM1 methylates chromatin remodeling factor BAF155 to enhance tumor progression and metastasis. Cancer cell 25: 21-36.

Wang P, Lin C, Smith E R, Guo H, Sanderson B W, Wu M, Gogol M, Alexander T, Seidel C, Wiedemann L M et al. 2009. Global analysis of H3K4 methylation defines MLL family member targets and points to a role for MLL1-mediated H3K4 methylation in the regulation of transcriptional initiation by RNA polymerase II. Mol Cell Biol 29: 6074-6085.

Wang Q, Trevino L S, Wong R L, Medvedovic M, Chen J, Ho S M, Shen J, Foulds C E, Coarfa C, O'Malley B W et al. 2016. Reprogramming of the Epigenome by MLL1 Links Early-Life Environmental Exposures to Prostate Cancer Risk. Molecular endocrinology 30: 856-871.

Wong P, Iwasaki M, Somervaille T C, So C W, Cleary M L. 2007. Meis1 is an essential and rate-limiting regulator of MLL leukemia stem cell potential. Genes & development 21: 2762-2774.

Wunsch D, Fetz V, Heider D, Tenzer S, Bier C, Kunst L, Knauer S, Stauber R. 2012. Chemico-genetic strategies to inhibit the leukemic potential of threonine aspartase-1. Blood cancer journal 2: e77.

Wunsch D, Hahlbrock A, Heiselmayer C, Backer S, Heun P, Goesswein D, Stocker W, Schirmeister T, Schneider G, Kramer O H et al. 2015. Fly versus maw evolutionary impairment of nucleolar targeting affects the degradome of *Drosophila*'s Taspase1. FASEB journal: official publication of the Federation of American Societies for Experimental Biology 29: 1973-1985.

Wunsch D, Hahlbrock A, Jung S, Schirmeister T, van den Boom J, Schilling O, Knauer S K, Stauber R H. 2016. Taspase1: a 'misunderstood' protease with translational cancer relevance. Oncogene 35: 3351-3364.

Yokoyama A, Ficara F, Murphy M J, Meisel C, Hatanaka C, Kitabayashi I, Cleary M L. 2013. MLL becomes functional through intra-molecular interaction not by proteolytic processing. PloS one 8: e73649.

Yokoyama A, Ficara F, Murphy M J, Meisel C, Naresh A, Kitabayashi I, Cleary M L. 2011. Proteolytically cleaved MLL subunits are susceptible to distinct degradation pathways. J Cell Sci 124: 2208-2219.

Yokoyama A, Kitabayashi I, Ayton P M, Cleary M L, Ohki M. 2002. Leukemia proto-oncoprotein MLL is proteolytically processed into 2 fragments with opposite transcriptional properties. Blood 100: 3710-3718.

Zeleznik-Le N J, Harden A M, Rowley J D. 1994. 11q23 translocations split the "AT-hook" cruciform DNA-binding region and the transcriptional repression domain from the activation domain of the mixed-lineage leukemia (MLL) gene. Proc Natl Acad Sci USA 91: 10610-10614.

Zhang P, Bergamin E, Couture J F. 2013. The many facets of MLL1 regulation. Biopolymers 99: 136-145.

Zhang Y, Liu T, Meyer C A, Eeckhoute J, Johnson D S, Bernstein B E, Nusbaum C, Myers R M, Brown M, Li W et al. 2008. Model-based analysis of ChIP-Seq (MACS). Genome biology 9: R137.

Zhao Z, Wang L, Wen Z, Ayaz-Guner S, Wang Y, Ahlquist P, Xu W. 2013. Systematic analyses of the cytotoxic effects of compound 11a, a putative synthetic agonist of photoreceptor-specific nuclear receptor (PNR), in cancer cell lines. PloS one 8: e75198.

Zhao Z, Wang L, Xu W. 2014. IL-13Ralpha2 mediates PNR-induced migration and metastasis in ERalpha-negative breast cancer. Oncogene.

Zhou H Q, Spicuglia S, Hsieh J J D, Mitsiou D J, Hoiby T, Veenstra G J C, Korsmeyer S J, Stunnenberg H G. 2006. Uncleaved TFIIA is a substrate for taspase 1 and active in transcription. Mol Cell Biol 26: 2728-2735.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating mixed-lineage rearranged gene (MML-r) leukemia in a subject in need thereof, the method comprising administering to the subject a therapeutic amount of a compound of the following formula or a pharmaceutical salt thereof:

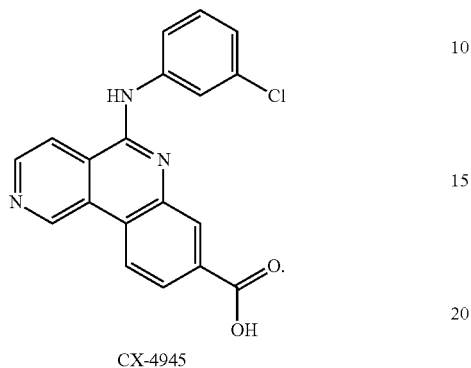

CX-4945

2. The method of claim 1, wherein the MML-r leukemia is Acute Lymphoblastic Leukemia (ALL) or Acute Myeloid Leukemia (AML).

* * * * *